US006740685B2

(12) United States Patent
Li et al.

(10) Patent No.: US 6,740,685 B2
(45) Date of Patent: May 25, 2004

(54) ORGANIC COMPOSITIONS

(75) Inventors: Bo Li, San Jose, CA (US); Paul G. Apen, San Jose, CA (US); Kreisler S. Lau, Sunnyvale, CA (US); Edward J. Sullivan, Campbell, CA (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/158,548

(22) Filed: May 30, 2002

(65) Prior Publication Data

US 2003/0114598 A1 Jun. 19, 2003

Related U.S. Application Data

(60) Provisional application No. 60/378,424, filed on May 7, 2002, provisional application No. 60/376,219, filed on Apr. 29, 2002, provisional application No. 60/353,011, filed on Jan. 30, 2002, provisional application No. 60/350,557, filed on Jan. 22, 2002, provisional application No. 60/350,187, filed on Jan. 15, 2002, and provisional application No. 60/294,864, filed on May 30, 2001.

(51) Int. Cl.$^7$ ................................................. C08J 9/02

(52) U.S. Cl. ......................................... 521/52; 521/77

(58) Field of Search ........................................... 521/52

(56) References Cited

U.S. PATENT DOCUMENTS

| | | | |
|---|---|---|---|
| 5,053,434 A | * 10/1991 | Chapman | |
| 5,347,063 A | 9/1994 | Shen et al. | 585/352 |
| 5,776,990 A | 7/1998 | Hedrick et al. | 521/77 |
| 5,895,263 A | 4/1999 | Carter et al. | 438/624 |
| 6,107,357 A | 8/2000 | Hawker et al. | 521/77 |
| 6,146,749 A | 11/2000 | Miyamoto et al. | 428/320.2 |
| 6,156,812 A | 12/2000 | Lau et al. | 521/77 |
| 6,171,687 B1 | 1/2001 | Leung et al. | 428/304.4 |
| 6,172,128 B1 | 1/2001 | Lau et al. | 521/77 |
| 6,214,746 B1 | 4/2001 | Leung et al. | 438/780 |
| 6,271,273 B1 | 8/2001 | You et al. | 521/61 |
| 6,342,454 B1 | 1/2002 | Hawker et al. | 438/780 |
| 6,359,091 B1 | 3/2002 | Godschalx et al. | 526/285 |
| 6,423,811 B1 | 7/2002 | Lau et al. | 528/125 |
| 6,451,712 B1 | 9/2002 | Dalton et al. | 438/781 |
| 6,509,415 B1 | * 1/2003 | Liu et al. | |
| 2001/0040294 A1 | 11/2001 | Hawker et al. | 23/48 |

FOREIGN PATENT DOCUMENTS

| | | |
|---|---|---|
| WO | WO 00/31183 | 6/2000 |
| WO | WO 01/78110 A2 | 10/2001 |

OTHER PUBLICATIONS

Veronica R. Reichert and Lon J. Mathias, "Tetrahedrally–Oriented Four–Armed Starand Branced Aramids", American Chemical Society, Macromolecules 1994, vol. 27, No. 24, pp. 7024–7029.

Veronica R. Reichert and Lon J. Mathais, "Highly Cross–Linked Polymers Based on Acetylene Derivatives of Tetraphenyladamantane", Americal Chemical Society, Macromolecules 1994, vol. 27, No. 24, pp. 7030–7034.

Denise R. Rutherford, J.K. Stille, C. Michael Elliott, Veronica R. Reichert, Poly(2,5–Ethynylenethiophenediyl-ethynylenes), Related Heteroaromatic Analogues, and Poly-(thien{3,2–b}thiphenes), Synthesis and Thermal and Electrical Properties, American Chemical Society, Macromolecules 1992, vol. 25, No. 9, pp. 2294–2306.

Charles M. Lewis and Lon J. Mathias, "Thermal Behavior of Polymers with Pendent Adamantyl Groups Using DMTA", Americal Chemical Society, Polym. Prepr. 1996, vol. 37(2), pp. 243–244.

Tina L. Grubb and Lon J. Mathias, "Synthesis of Benzyl Ether Polymers Containing Pendant Adamantyl Groups and the Effect on Polymer Properties", Americal Chemical Society, Polym. Prepr., 1996, vol. 37(1), pp. 551–552.

Charles M. Lewis, Lon J. Mathias, and Nichola Wiegal, "A New Class of Poly(ether ether Ketone)s based on Adamantyl–substituted Bisphenols: Effects of Pendent Adamantyl Groups on Polymer Properties", American Chemical Society, Polym. Prepr. 1995, vol. 36(2), pp. 140–141.

Veronica R. Reichert and Lon J. Mathias, "Rigid–Expanded Tetrahedral Cores for Four–Armed Branched Structures: 1,3,5,7–Tetrakis(4–iodophenyl)adamantane and its Derivatives", American Chemical Society, Polym. Prepr. 1993, vol. 34(1), pp. 495–496.

Lon J. Mathias and Veronica R. Reichert, "Synthesis of Macromolecules from 1,3,5, 7–Tetra(4–iodophenyl)adamantane: A New Core for Dendritic Molecules", American Chemical Society, Polym. Prepr. 1992, vol. 33(2), pp. 144–145.

Lon J. Mathias and Ralph M. Bozen, "Linear and Star–Branched Siloxy–Silane Polymers: One–pot A–B Polymerization and End–capping", American Chemical Society, Polym. Prepr. 1992, vol. 33(2), pp. 146–147.

(List continued on next page.)

*Primary Examiner*—Morton Foelak
(74) *Attorney, Agent, or Firm*—Sandra P. Thompson; Bingham McCutchen

(57) ABSTRACT

The present invention provides a composition comprising (a) thermosetting component comprising: (1) optionally monomer of Formula I as set forth below and (2) at least one oligomer or polymer of Formula II as set forth below where E, Q, G, h, l, j, and w are as set forth below and (b) porogen that bonds to thermosetting component (a). Preferably, the porogen is selected from the group consisting of unsubstituted polynorbornene, substituted polynorbornene, polycaprolactone, unsubstituted polystyrene, substituted polystyrene, polyacenaphthylene homopolymer, and polyacenaphthylene copolymer. Preferably, the present compositions may be used as dielectric substrate in microchips, multichip modules, laminated circuit boards, or printed wiring boards.

54 Claims, 26 Drawing Sheets

OTHER PUBLICATIONS

Lon J. Mathias, Charles M. Lewis and Kurt N. Wiegel, "*Poly(ehter ether ketone)s and Poly(ether sulfones) with Pendent Adamantyl Groups*", American Chemical Society, Macromolecules 1997, vol. 30, No. 19, pp. 5970–5975.

Havva Yagei Acar, Jennifer J. Jensen, Kevin Thigpen, John A McGowen and Lon J. Mathias, "*Evaluation of the Spacer Effect on Adamantane–Containing Vinyl Polymer Tg's*" American Chemical Society, Macromolecules 2000, vol. 34, No. 10, pp. 3855–3859.

Lon J. Mathias, Veronica R. Reichert and Andrew V.G. Muir, "*Synthesis of Rigid Tetrofunctional Molecules from 1,3,5, 7–Tetrakis(4–iodophenyl)adamantane*", American Chemical Society, Chem. Mater. 1993, vol. 5, No. 1, pp. 4–5.

Jennifer J. Jensen, Michael Grimsley and Lon J. Mathias, "*Adamantyl–Substituted Phenolic Polymers*", Journal of Polymer Science: Part A: Polymer Chemistry, 1996, vol. 34, pp. 397–402.

Lon J. Mathis, Gregory J. Tregre, *Synthesis, Characterization, and Cure of Allyl and Propargyl Functionalized Indene as a Thermoset Composite Matrix Resin*, Journal of Applied Polymer Science, 1998, vol. 68, pp. 475–482.

* cited by examiner 1,3/4-bis[1',3',5'-tris(3''/4''-bromophenyl)adamant-7'-yl]benzene

+

1,3-bis{3'/4'-[1''',3''',5'''-tris(3''''/4''''-bromophenyl)adamant-7'''-yl]phenyl}
-5,7-bis(3'''''/4'''''-bromophenyl)adamantane

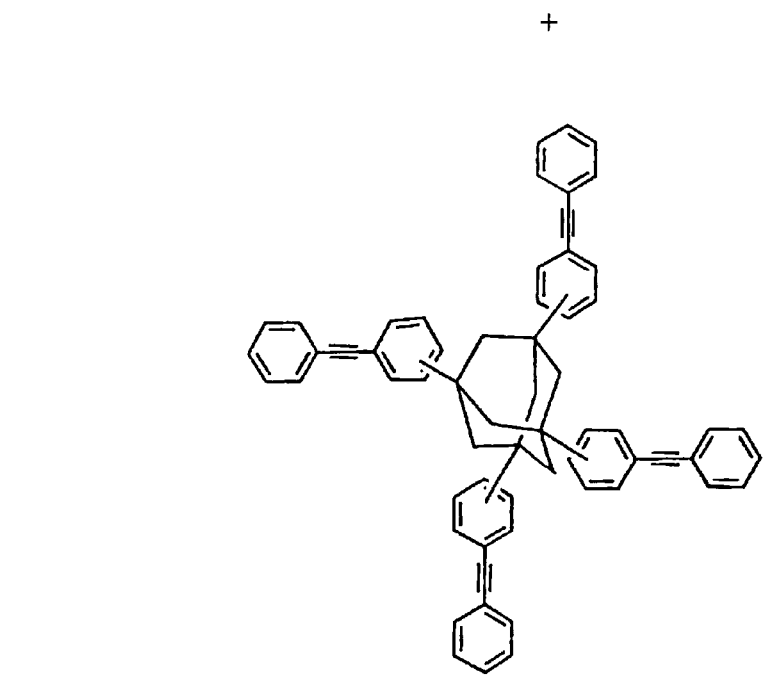
1,3,5,7-tetrakis[3'/4'-phenylethynyl)phenyl]adamantane
FIGURE 1D
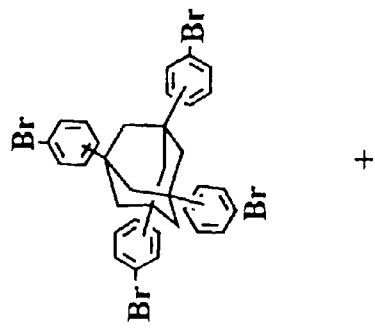
FIGURE 1C products 1,3/4-bis{1',3',5'-tris[3''/4''-(phenylethynyl)phenyl]adamant-7'-yl}benzene

+

1,3-bis{3'/4'-[1'',3'',5''-tris[3''''',4'''''-(phenylethynyl)phenyl]adamant-7''-yl]phenyl}-
5,7-bis{3'''',4''''-(phenylethynyl)phenyl]adamantane 1,3/4-bis[2',4',9'-tris(3''/4''-bromophenyl)diamant-11'-yl]benzene

+

2,4-bis{3'/4'-[2'',4'',9''-tris(3'''/4'''-bromophenyl)diamant-11''-yl]phenyl}-
9,11-bis(3''''/4''''-bromophenyl)diamantane FIGURE 3C products 1,3/4-bis{2',4',9'-tris[3'',4''-(phenylethynyl)phenyl]diamant-11'-yl}benzene

+

2,4-bis{3'/4'-[2'',4'',9''-tris[3'''/4'''-(phenylethynyl)phenyl]diamant-11''-yl]phenyl}-
9,11-bis[3''''/4''''-(phenylethynyl)phenyl]diamantane SEM: Cross SEM: Surface $R_{35}$ = hydrogen, phenyl, butyl, or hexyl

ORGANIC COMPOSITIONS

BENEFIT OF PENDING APPLICATIONS

This application claims the benefit of pending commonly assigned provisional patent applications 60/294,864 filed May 30, 2001; 60/350,187 filed Jan. 15, 2002; 60/350,557 filed Jan. 22, 2002; 60/353,011 filed Jan. 30, 2002; 60/376,219 filed Apr. 29, 2002, and 60/378,424 filed May 7, 2002, incorporated herein in their entirety.

FIELD OF THE INVENTION

The present invention relates to semiconductor devices, and in particular, to semiconductor devices having an organic low dielectric constant material and processes for the manufacture thereof.

BACKGROUND OF THE INVENTION

In an effort to increase the performance and speed of semiconductor devices, semiconductor device manufacturers have sought to reduce the linewidth and spacing of interconnects while minimizing the transmission losses and reducing the capacitative coupling of the interconnects. One way to diminish power consumption and reduce capacitance is by decreasing the dielectric constant (also referred to as "k") of the insulating material, or dielectric, that separates the interconnects. Insulator materials having low dielectric constants are especially desirable, because they typically allow faster signal propagation, reduce capacitance and cross talk between conductor lines, and lower voltages required to drive integrated circuits.

Since air has a dielectric constant of 1.0, a major goal is to reduce the dielectric constant of insulator materials down to a theoretical limit of 1.0, and several methods are known in the art for reducing the dielectric constant of insulating materials. These techniques include adding elements such as fluorine to the composition to reduce the dielectric constant of the bulk material. Other methods to reduce k include use of alternative dielectric material matrices. Another approach is to introduce pores into the matrix.

Therefore, as interconnect linewidths decrease, concomitant decreases in the dielectric constant of the insulating material are required to achieve the improved performance and speed desired of future semiconductor devices. For example, devices having interconnect linewidths of 0.13 or 0.10 micron and below seek an insulating material having a dielectric constant (k)<3.

Currently silicon dioxide ($SiO_2$) and modified versions of $SiO_2$, such as fluorinated silicon dioxide or fluorinated silicon glass (hereinafter FSG) are used. These oxides, which have a dielectric constant ranging from about 3.5–4.0, are commonly used as the dielectric in semiconductor devices. While $SiO_2$ and FSG have the mechanical and thermal stability needed to withstand the thermal cycling and processing steps of semiconductor device manufacturing, materials having a lower dielectric constant are desired in the industry.

Methods used to deposit dielectric materials may be divided into two categories: spin-on deposition (hereinafter SOD) and chemical vapor deposition (hereinafter CVD). Several efforts to develop lower dielectric constant materials include altering the chemical composition (organic, inorganic, blend of organic/inorganic) or changing the dielectric matrix (porous, non-porous). Table I summarizes the development of several materials having dielectric constants ranging from 2.0 to 3.5. (PE=plasma enhanced; HDP= high-density plasma) However, the dielectric materials and matrices disclosed in the publications shown in Table 1 fail to exhibit many of the combined physical and chemical properties desirable and even necessary for effective dielectric materials, such as higher mechanical stability, high thermal stability, high glass transition temperature, high modulus or hardness, while at the same time still being able to be solvated, spun, or deposited on to a substrate, wafer, or other surface. Therefore, it may be useful to investigate other compounds and materials that may be used as dielectric materials and layers, even though these compounds or materials may not be currently contemplated as dielectric materials in their present form.

TABLE 1

| MATERIAL | DEPOSITION METHOD | DIELECTRIC CONSTANT (k) | REFERENCE |
| --- | --- | --- | --- |
| Fluorinated silicon oxide (SiOF) | PE-CVD; HDP-CVD | 3.3–3.5 | U.S. Pat. No. 6,278,174 |
| Hydrogen Silsesquioxane (HSQ) | SOD | 2.0–2.5 | U.S. Pat. Nos. 4,756,977; 5,370,903; and 5,486,564; International Patent Publication WO 00/40637; E.S. Moyer et al., "Ultra Low k Silsesquioxane Based Resins", Concepts and Needs for Low Dielectric Constant <0.15 μm Interconnect Materials: Now and the Next Millennium, Sponsored by the American Chemical Society, pages 128–146 (Nov. 14–17, 1999) |
| Methyl Silsesquioxane (MSQ) | SOD | 2.4–2.7 | U.S. Pat. No. 6,143,855 |
| Polyorganosilicon | SOD | 2.5–2.6 | U.S. Pat. No. 6,225,238 |
| Fluorinated Amorphous Carbon (a-C:F) | HDP—CVD | 2.3 | U.S. Pat. No. 5,900,290 |
| Benzocyclobutene (BCB) | SOD | 2.4–2.7 | U.S. Pat. No. 5,225,586 |
| Polyarylene Ether (PAE) | SOD | 2.4 | U.S. Pat. Nos. 5,986,045; 5,874,516; and 5,658,994 |
| Parylene (N and F) | CVD | 2.4 | U.S. Pat. No. 5,268,202 |
| Polyphenylenes | SOD | 2.6 | U.S. Pat. Nos. 5,965,679 and 6,288,188B1; and Waeterloos et al., "Integration Feasibility of Porous SiLK Semiconductor Dielectric", Proc. Of the 2001 International Interconnect Tech. Conf., pp. 253–254 (2001). |

TABLE 1-continued

| MATERIAL | DEPOSITION METHOD | DIELECTRIC CONSTANT (k) | REFERENCE |
|---|---|---|---|
| Thermosettable benzocyclobutenes, polyarylenes, thermosettable perfluoroethylene monomer | SOD | 2.3 | International Patent Publication WO 00/31183 |
| Poly(phenylquinoxaline), organic polysilica | SOD | 2.3–3.0 | U.S. Pat. Nos. 5,776,990; 5,895,263; 6,107,357; and 6,342,454; and U.S. patent Publication 2001/0040294 |
| Organic polysilica | SOD | Not reported | U.S. Pat. No. 6,271,273 |
| Organic and inorganic Materials | SOD | 2.0–2.5 | U.S. Pat. No. 6,156,812 |
| Organic and inorganic Materials | SOD | 2.0–2.3 | U.S. Pat. No. 6,171,687 |
| Organic materials | SOD | Not reported | U.S. Pat. No. 6,172,128 |
| Organic | SOD | 2.12 | U.S. Pat. No. 6,214,746 |
| Organosilsesquioxane | CVD, SOD | <3.9 | WO 01/29052 |
| Fluorosilsesquioxane | CVD, SOD | <3.9 | WO 01/29141 |

Unfortunately, numerous organic SOD systems under development with a dielectric constant between 2.0 and 3.5 suffer from certain drawbacks in terms of mechanical and thermal properties as described above; therefore a need exists in the industry to develop improved processing and performance for dielectric films in this dielectric constant range. In addition, industry demands materials having demonstrated low dielectric constant extendibility, i.e. capable of being reduced to an even lower dielectric constant, e.g., from 2.7 to 2.5 to 2.2 to 2.0 and below.

Reichert and Mathias describe compounds and monomers that comprise adamantane molecules, which are in the class of cage-based molecules and are taught to be useful as diamond substitutes. (Polym, Prepr. (Am. Chem. Soc., Div. Polym. Chem.), 1993, Vol. 34 (1), pp. 495–6; Polym, Prepr. (Am. Chem. Soc., Div. Polym. Chem.), 1992, Vol. 33 (2), pp. 144–5; Chem. Mater., 1993, Vol. 5 (1), pp. 4–5; Macromolecules, 1994, Vol. 27 (24), pp. 7030–7034; Macromolecules, 1994, Vol. 27 (24), pp. 7015–7023; Polym, Prepr. (Am. Chem. Soc., Div. Polym. Chem.), 1995, Vol. 36 (1), pp. 741–742; 205$^{th}$ ACS National Meeting, Conference Program, 1993, pp. 312; Macromolecules, 1994, Vol. 27 (24), pp. 7024–9; Macromolecules, 1992, Vol. 25 (9), pp. 2294–306; Macromolecules, 1991, Vol. 24 (18), pp. 5232–3; Veronica R. Reichert, PhD Dissertation, 1994, Vol. 55-06B; ACS Symp. Ser.: Step-Growth Polymers for High-Performance Materials, 1996, Vol. 624, pp. 197–207; Macromolecules, 2000, Vol. 33 (10), pp. 3855–3859; Polym, Prepr. (Am. Chem. Soc., Div. Polym. Chem.), 1999, Vol. 40 (2), pp. 620–621; Polym, Prepr. (Am. Chem. Soc., Div. Polym. Chem.), 1999, Vol. 40 (2), pp. 577–78; Macromolecules, 1997, Vol. 30 (19), pp. 5970–5975; J. Polym. Sci, Part A: Polymer Chemistry, 1997, Vol. 35 (9), pp. 1743–1751; Polym, Prepr. (Am. Chem. Soc., Div. Polym. Chem.), 1996, Vol. 37 (2), pp. 243–244; Polym, Prepr. (Am. Chem. Soc., Div. Polym. Chem.), 1996, Vol. 37 (1), pp. 551–552; J. Polym. Sci., Part A: Polymer Chemistry, 1996, Vol. 34 (3), pp. 397–402; Polym, Prepr. (Am. Chem. Soc., Div. Polym. Chem.), 1995, Vol. 36 (2), pp. 140–141; Polym, Prepr. (Am. Chem. Soc., Div. Polym. Chem.), 1992, Vol. 33 (2), pp. 146–147; J. Appl. Polym. Sci., 1998, Vol. 68 (3), pp. 475–482). The adamantane-based compounds and monomers described by Reichert and Mathias are preferably used to form polymers with adamantane molecules at the core of a thermoset. The compounds disclosed by Reichert and Mathias in their studies, however, comprise only one isomer of the adamantane-based compound by design choice. Structure A shows this symmetrical para-isomer 1,3,5,7-tetrakis[4'-(phenylethynyl)phenyl]adamantane:

Structure A

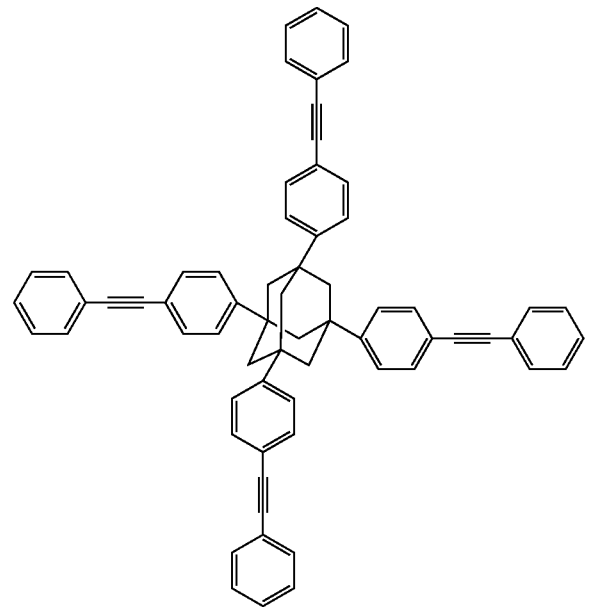

In other words, Reichert and Mathias in their individual and joint work contemplated a useful polymer comprising only one isomer form of the target adamantane-based monomer. A significant problem exists, however, when forming and processing polymers from the single isomer form (symmetrical "all-para" isomer) 1,3,5,7-tetrakis[4'-(phenylethynyl)phenyl]adamantane of the adamantane-based monomer. According to the Reichert dissertation (supra) and Macromolecules, vol. 27, (pp. 7015–7034) (supra), the symmetrical all-para isomer 1,3,5,7-tetrakis[4'-(phenylethynyl)phenyl]adamantane "was found to be soluble enough in chloroform that a $^1$H NMR spectrum could be obtained. However, acquisition times were found to be impractical for obtaining a solution $^{13}$C NMR spectrum." indicating that the all para isomer has low solubility. Thus, the Reichert symmetrical "all-para" isomer 1,3,5,7-tetrakis [4'-(phenylethynyl)phenyl]adamantane is insoluble in standard organic solvents and therefore, would not be useful in any application requiring solubility or solvent-based processing, such as flow coating, spin coating, or dip coating.

In our commonly assigned pending patent application PCT/US01/22204 filed Oct. 17, 2001 (claiming the benefit of our commonly assigned pending patent applications U.S. Ser. No. 09/545058 filed Apr. 7, 2000; U.S. Ser. No. 09/618945 filed Jul. 19, 2000; U.S. Ser. No. 09/897936 filed Jul. 5, 2001; and U.S. Ser. No. 09/902924 filed Jul. 10, 2001; and International Publication WO 01/78110 published Oct. 18, 2001), we discovered a composition comprising an isomeric thermosetting monomer or dimer mixture, wherein the mixture comprises at least one monomer or dimer having the structure correspondingly

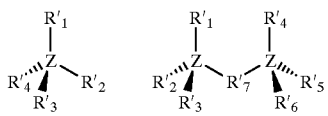

wherein Z is selected from cage compound and silicon atom; $R'_1$, $R'_2$, $R'_3$, $R'_4$, is $R'_5$, and $R'_6$ are independently selected from aryl, branched aryl, and arylene ether; at least one of the aryl, the branched aryl, and the arylene ether has an ethynyl group; and $R'_7$ is aryl or substituted aryl. We also disclose methods for formation of these thermosetting mixtures. This novel isomeric thermosetting monomer or dimer mixture is useful as a dielectric material in microelectronics applications and soluble in many solvents such as cyclohexanone. These desirable properties make this isomeric thermosetting monomer or dimer mixture ideal for film formation at thicknesses of about 0.1 μm to about 1.0 μm.

We filed a patent application Serial No. 10/160,773 on even date herewith that claims a porous version of the preceding isomeric mixture.

Our International Patent Publication WO 01/78110 published Oct. 18, 2001 teaches in its background section that methods for introducing nanosized voids include physical blending or chemical grafting of thermostable or thermolabile portions. This publication's invention is that nanosized voids may be introduced into dielectric materials by using cage structures such as adamantane or diamantane to achieve low dielectric constant material and defines low dielectric constant materials as having a dielectric constant of less than 3.0. However, this publication does not report any dielectric constant for its examples.

International Patent Publication WO 00/31183 teaches in its background section that although known porous thermoplastic materials had acceptable dielectric constants, the pores tended to collapse during subsequent high temperature processing and thus, the art teaches away from adding porosity to the cage structure that introduced nanosized voids in International Patent Publication WO 01/78110 published Oct. 18, 2001. In addition, U.S. Pat. Nos. 5,776,990; 5,895,263; 6,107,357; and 6,342,454 and U.S. Publication 2001/0040294 teach that although dielectric constants of 2.3–2.4 had been achieved at porosity levels less than about 20%, the pore content could not be further increased without comprising the small domain sizes and/or the non-interconnectivity of the pore structure. Similarly, U.S. Pat. Nos. 6,271,273; 6,156,812; 6,171,687; and 6,172,128 teach that the amount of the thermally labile monomer unit is limited to amounts less than about 30% by volume because if more than about 30% by volume of the thermally labile monomer is used, the resulting dielectric material has cylindrical or lamellar domains, instead of pores or voids, which lead to interconnected or collapsed structures upon removal, i.e., heating to degrade the thermally labile monomer units.

Although various methods are known in the art to lower the dielectric constant of a material, these methods have disadvantages. Thus, there is still a need in the semiconductor industry to a) provide improved compositions and methods to lower the dielectric constant of dielectric layers; b) provide dielectric materials with improved properties, such as thermal stability, glass transition temperature ($T_g$), modulus, and hardness; c) produce thermosetting compounds and dielectric materials that are capable of being solvated and spun-on to a wafer or layered material; and d) provide materials with demonstrated extendibility.

The present invention advantageously provides demonstrated extendibility so that semiconductor device manufacturers can use the present compositions for numerous generations of microchips. Also, the present invention provides for bonding of a porogen to a thermosetting component and thus, porogen movement is minimized and the possibility of pore aggregation is reduced.

SUMMARY OF THE INVENTION

In response to the need in the art and proceeding contrary to the wisdom in the art, we developed a composition comprising:

(a) thermosetting component comprising: (1) optionally monomer of Formula I

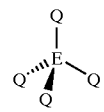

and (2) at least one oligomer or polymer of Formula II

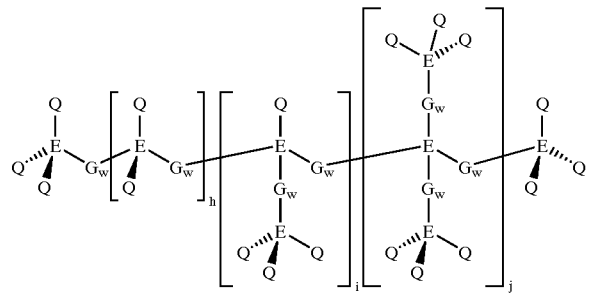

where E is a cage compound; each of Q is the same or different and selected from aryl, branched aryl, and substituted aryl wherein said substituents include hydrogen, halogen, alkyl, aryl, substituted aryl, heteroaryl, aryl ether, alkenyl, alkynyl, alkoxyl, hydroxyalkyl, hydroxyaryl, hydroxyalkenyl, hydroxyalkynyl, hydroxyl, or carboxyl; G is aryl or substituted aryl where substituents include halogen and alkyl; h is from 0 to 10; i is from 0 to 10; j is from 0 to 10; and w is 0 or 1;

(b) porogen that bonds to the thermosetting component (a).

We also discovered a method of lowering the dielectric constant of a composition comprising: (a) thermosetting component comprising: (1) optionally monomer of Formula I above and (2) at least one oligomer or polymer of Formula II above where E, Q, G, h, I, and j are defined as above; and (b) adhesion promoter comprising compound having at least bifunctionality wherein the bifunctionality may be the same or different and the first functionality is capable of interacting with the thermosetting component (a) and the second functionality is capable of interacting with a substrate when the composition is applied to the substrate comprising the steps of:

bonding porogen to the thermosetting component;

decomposing the bonded porogen; and volatilizing the decomposed porogen whereby pores form in the composition.

BRIEF DESCRIPTION OF THE DRAWINGS

FIGS. 1A through 1F illustrates how to make adamantane based compositions useful as the thermosetting component in the present compositions.

DETAILED DESCRIPTION OF THE INVENTION

Figure 1A:
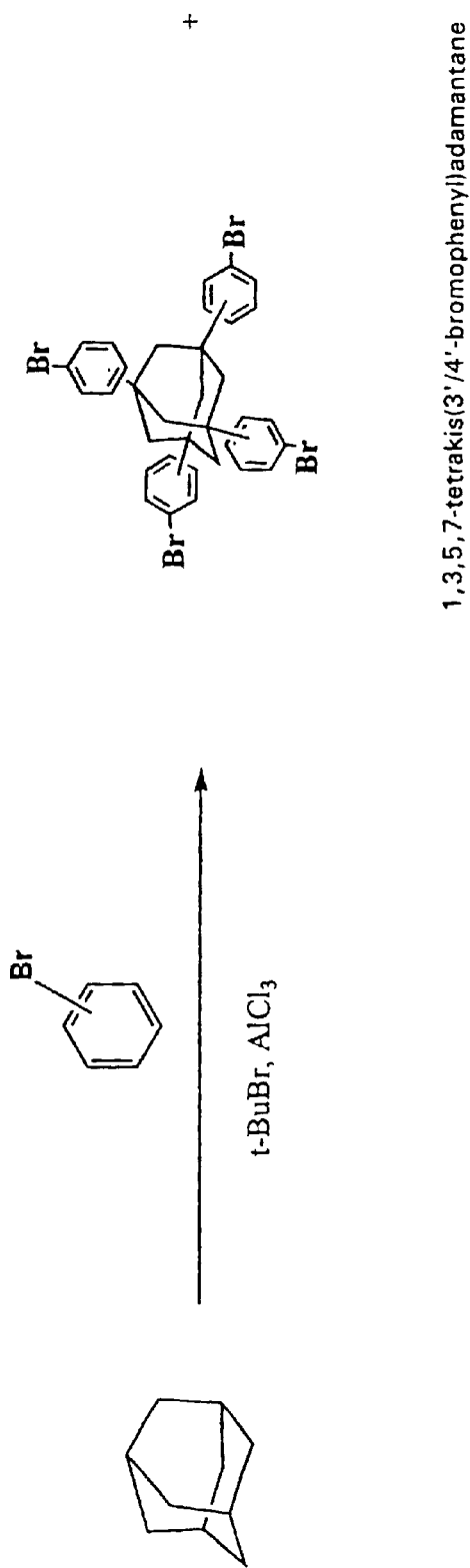

We filed a patent application Ser. No. 10/158,513 on even date herewith that claims a composition of a thermosetting component and a porogen wherein the porogen does not have to bond to the thermosetting component.

Thermosetting Component:

The phrases "cage structure", "cage molecule", and "cage compound" as used herein are intended to be used interchangeably and refer to a molecule having at least eight atoms arranged such that at least one bridge covalently connects two or more atoms of a ring system. In other words, a cage structure, cage molecule, or cage compound comprises a plurality of rings formed by covalently bound atoms, wherein the structure, molecule, or compound defines a volume, such that a point located within the volume cannot leave the volume without passing through the ring. The bridge and/or the ring system may comprise one or more heteroatoms, and may contain aromatic groups, partially cyclic or acyclic saturated hydrocarbon groups, or cyclic or acyclic unsaturated hydrocarbon groups. Further contemplated cage structures include fullerenes, and crown ethers having at least one bridge. For example, an adamantane or diamantane is considered a cage structure, while a naphthalene or an aromatic spirocompound are not considered a cage structure under the scope of this definition, because a naphthalene or an aromatic spirocompound do not have one, or more than one bridge and thus, do not fall within the description of the cage compound above. Cage compounds are preferably adamantane and diamantane and more preferably adamantane.

The phrase "bridgehead carbon" as used herein refers to any cage structure carbon bound to three other carbons. Thus, for example, adamantane has four bridgehead carbons while diamantane has eight bridgehead carbons.

Preferred dielectric material is thermosetting component disclosed and claimed in our commonly assigned pending patent application Ser. No. 60/347195 filed Jan. 8, 2002 and 60/384,303 filed on even date herewith, which are incorporated herein by reference in their entirety.

Preferably, the thermosetting component (a) comprises:

(1) adamantane monomer of Formula III

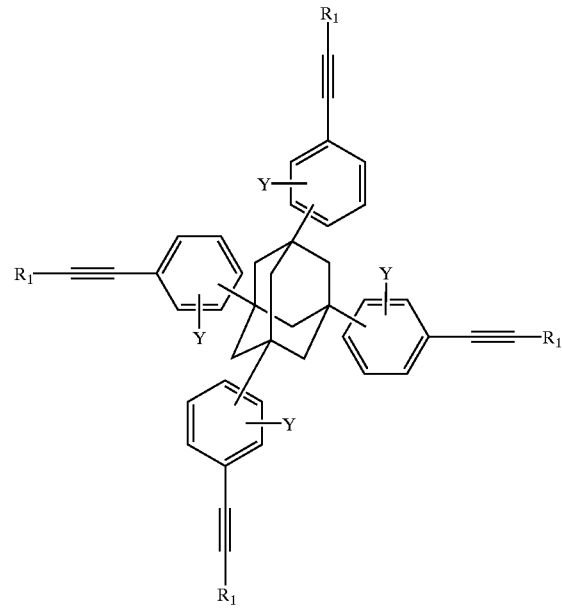

and (2) adamantane oligomer or polymer of Formula IV

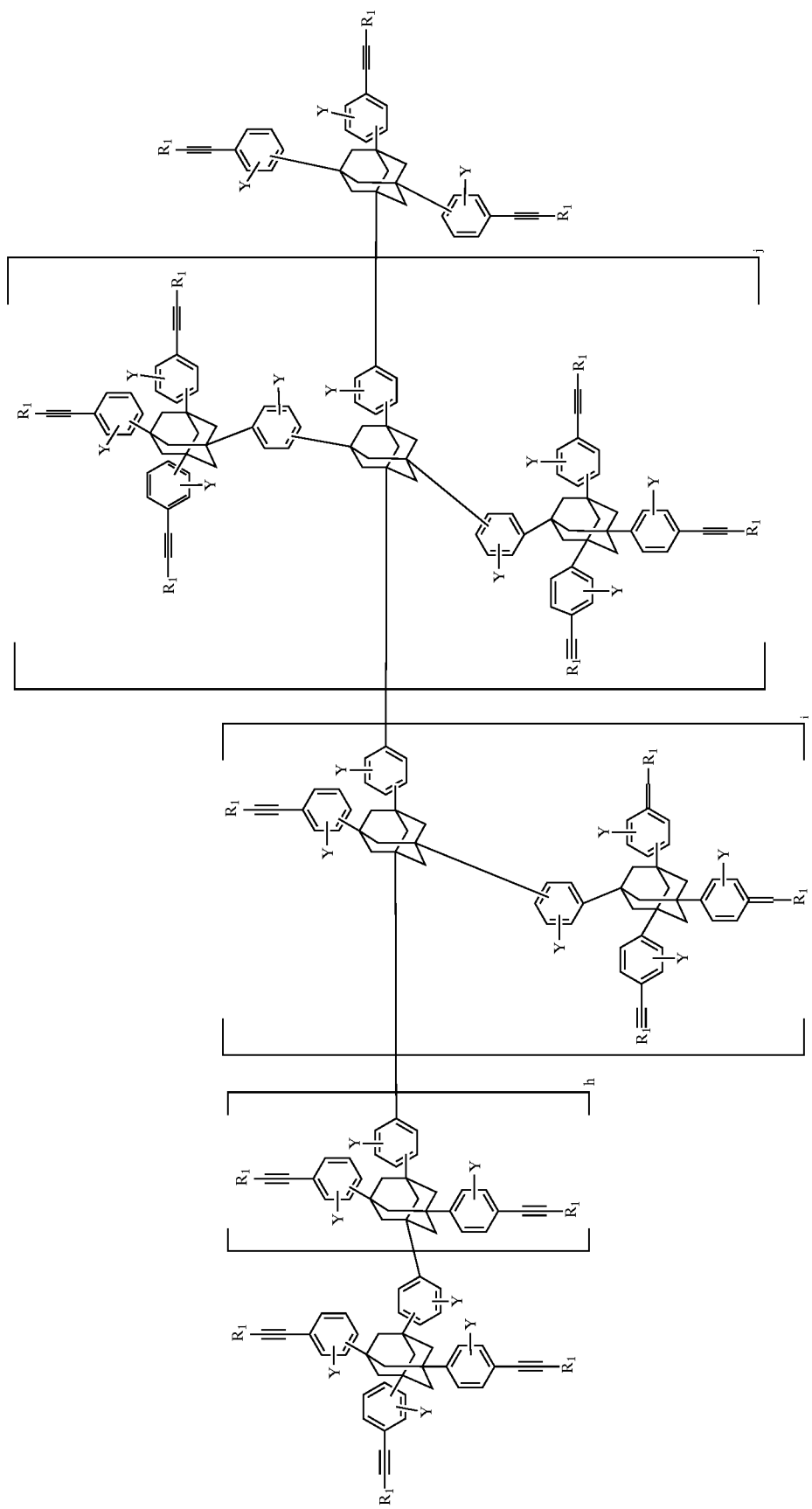

or (1) diamantane monomer of Formula V
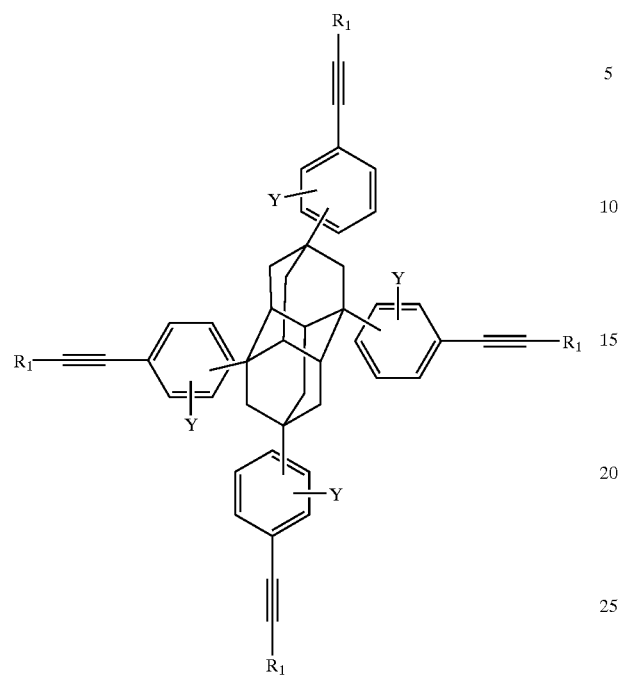
and (2) diamantane oligomer or polymer of Formula VI

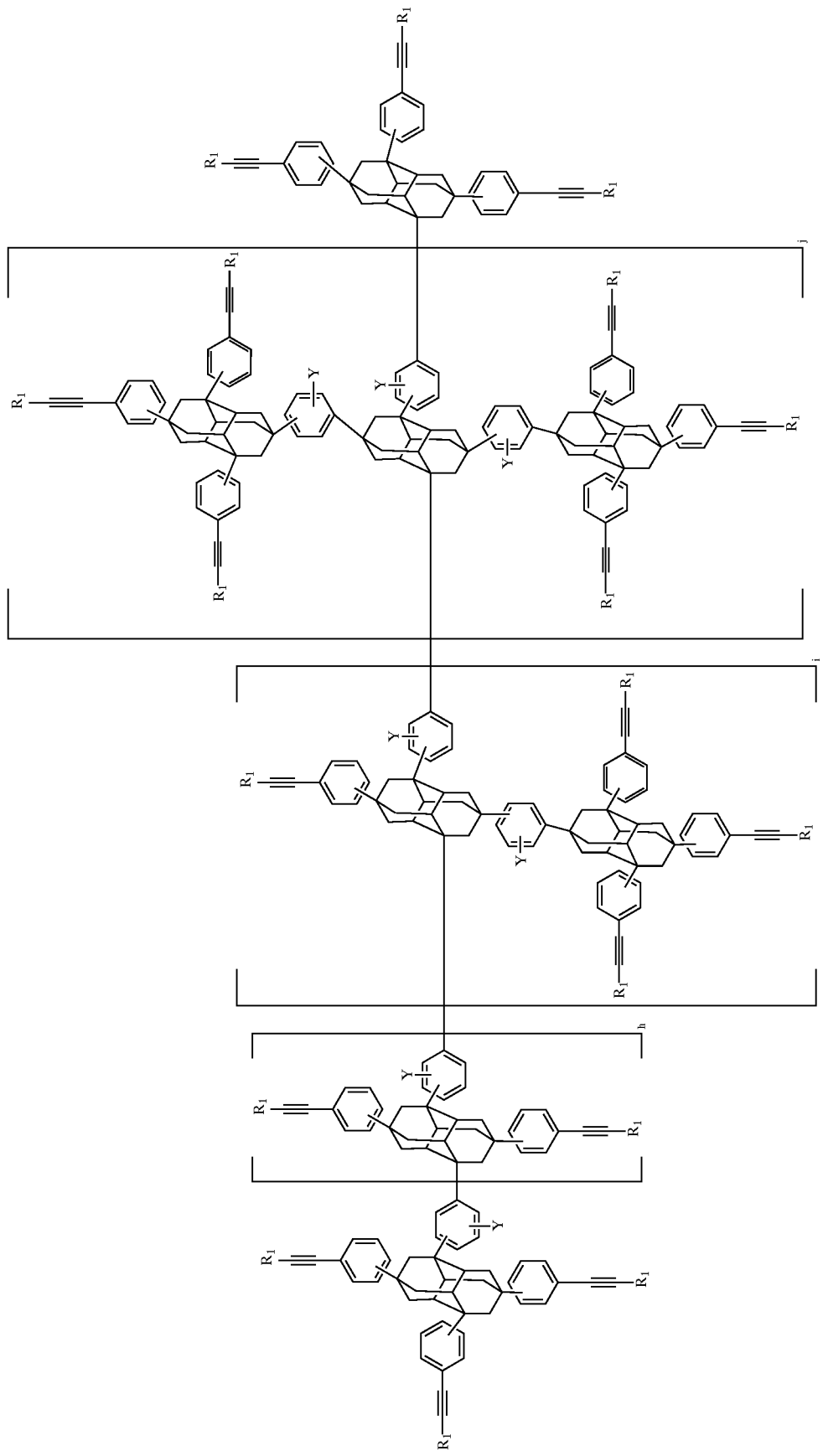

wherein h is from 0 to 10; i is from 0 to 10; j is from 0 to 10; each $R_1$ in Formulae III, IV, V, and VI is the same or different and selected from hydrogen, halogen, alkyl, aryl, substituted aryl, heteroaryl, aryl ether, alkenyl, alkynyl, alkoxyl, hydroxyalkyl, hydroxyaryl, hydroxyalkenyl, hydroxyalkynyl, hydroxyl, or carboxyl; and each Y in Formulae III, IV, V, and VI is the same or different and selected from hydrogen, alkyl, aryl, substituted aryl, or halogen.

Formulae II, IV, and VI represent random or irregular structures in that any one of the units h, i, and j may or may not repeat numerous times before another unit is present.

Thus, the sequence of units in Formulae II, IV, and VI above is random or irregular.

In the one embodiment, preferably the thermosetting component comprises adamantane monomer of Formula III above and at least one adamantane oligomer or polymer of Formula IV above where at least one of h, i, and j is at least 1. Preferably, the thermosetting component comprises diamantane monomer of Formula V above and at least one diamantane oligomer or polymer of Formula VI above where at least one of h, i, and j is at least 1.

Preferably, the thermosetting component comprises adamantane monomer of Formula III above and adamantane oligomer or polymer of Formula VII below.

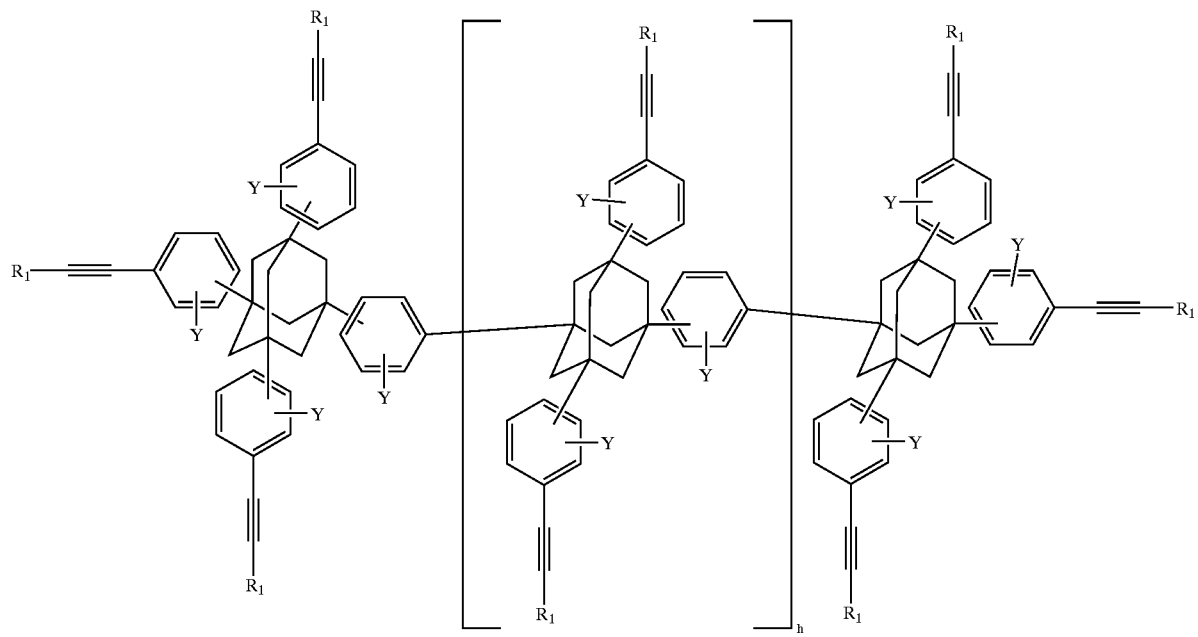

Preferably, the thermosetting component comprises diamantane monomer of Formula V above and diamantane oligomer or polymer of Formula VII below.
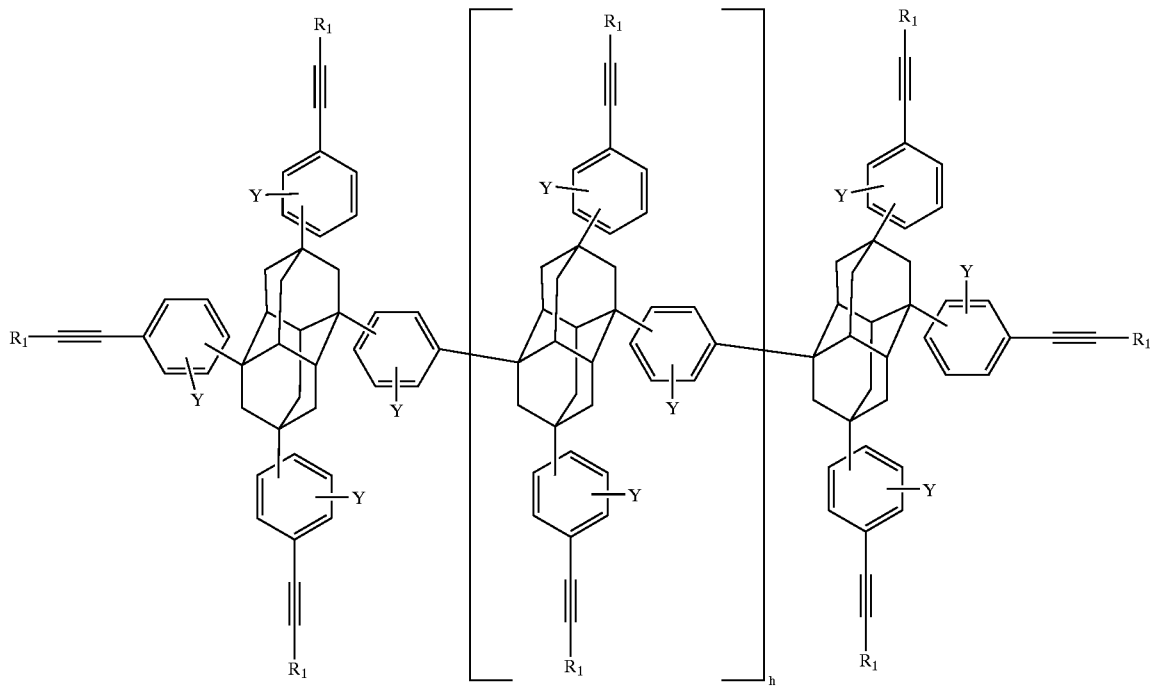
35
Preferably, the thermosetting component comprises adamantane monomer of Formula III above and adamantane dimer of Formula IX below.
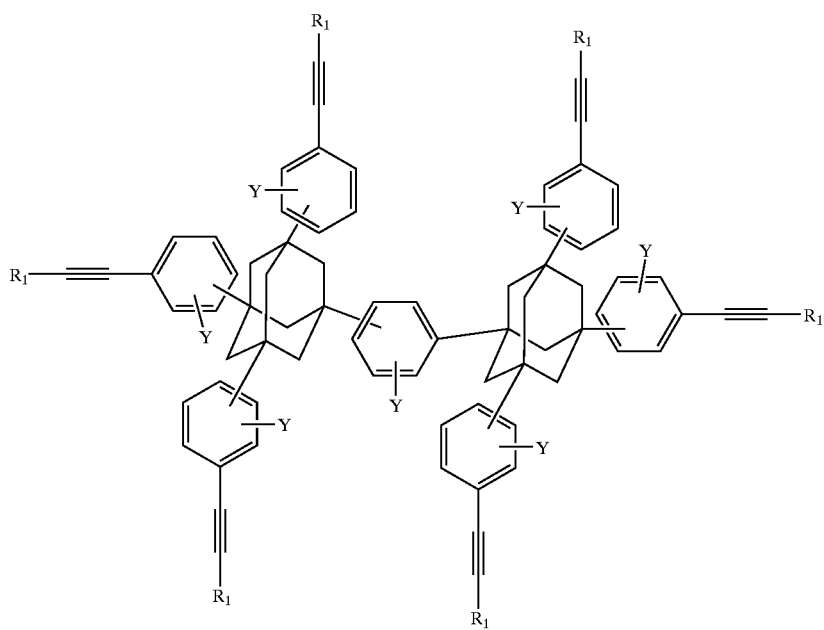

Preferably, the thermosetting component comprises diamantane monomer of Formula V above and diamantane dimer of Formula X below.
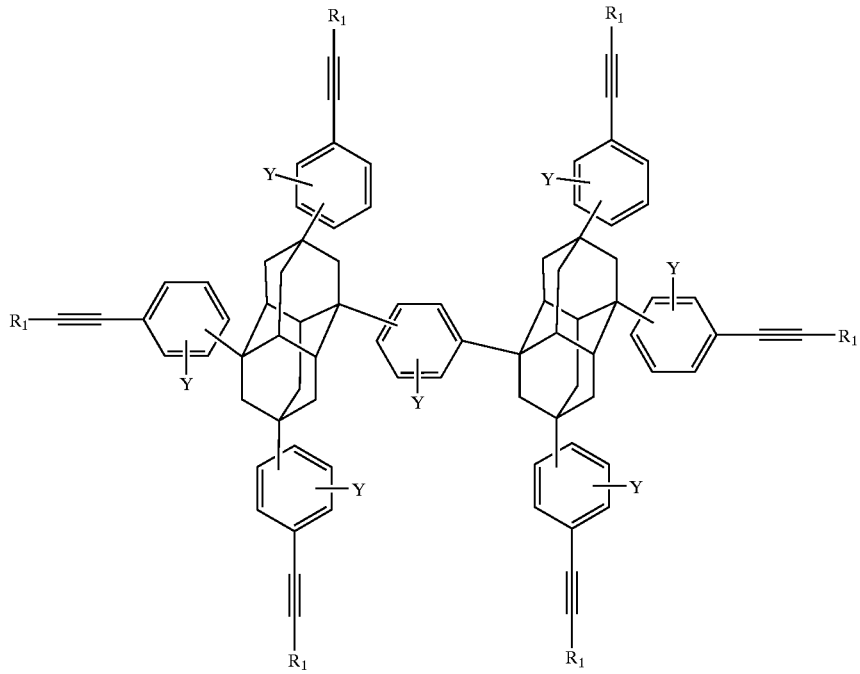
Preferably, the thermosetting component comprises adamantane monomer of Formula III above and adamantane trimer of Formula XI below.
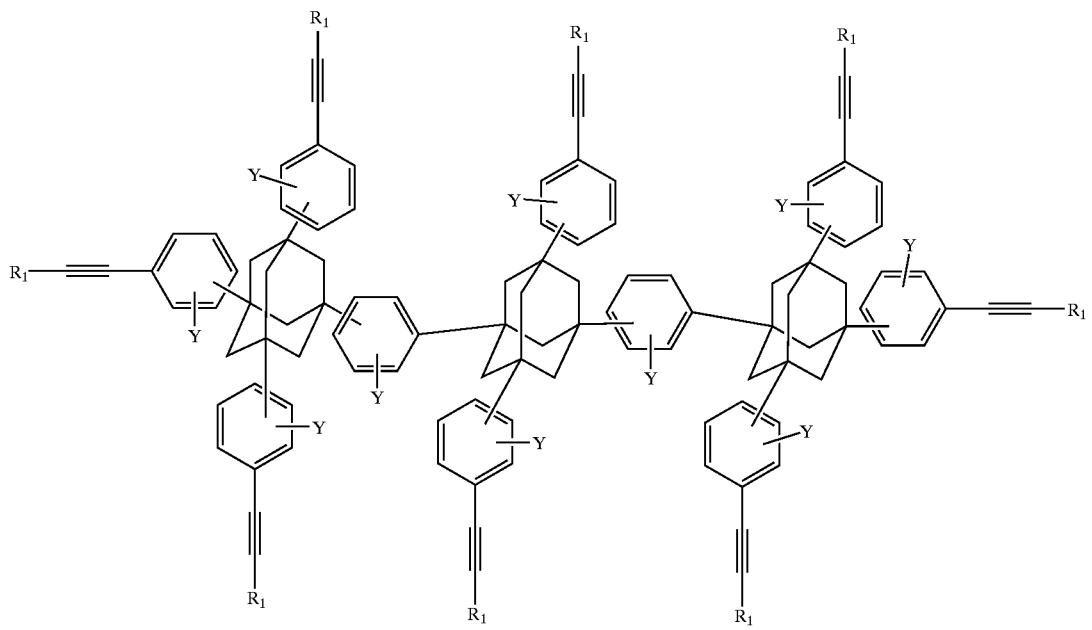

Preferably, the thermosetting component comprises diamantane monomer of Formula V above and diamantane trimer of Formula XII below.

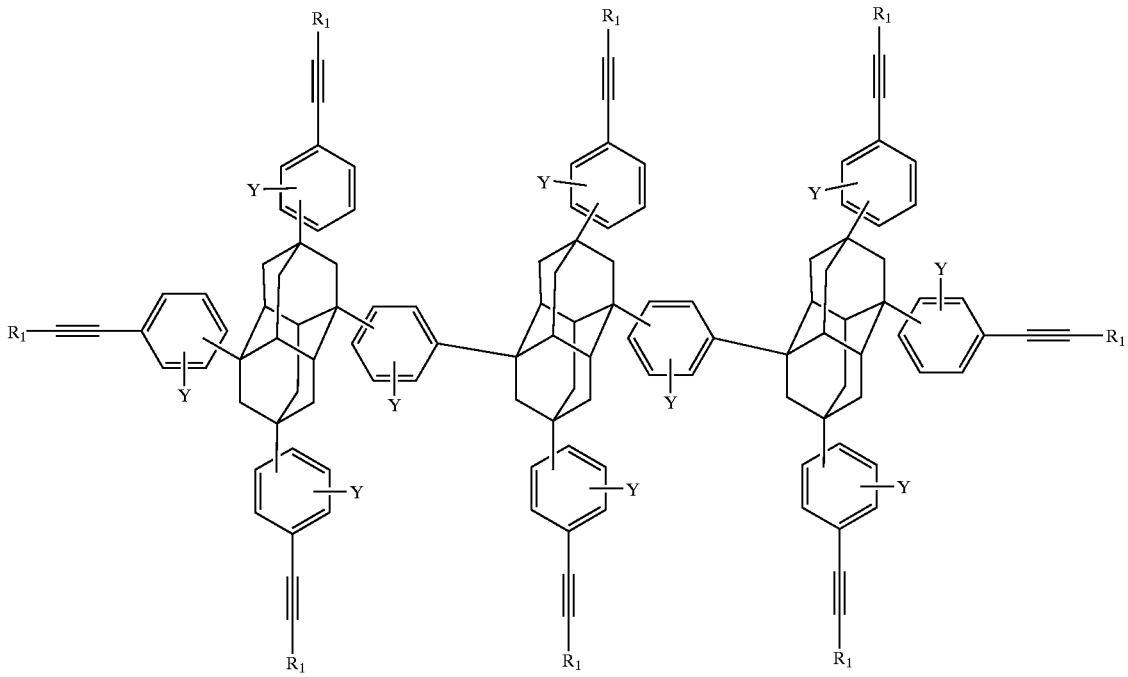

Preferably, the thermosetting component comprises adamantane monomer of Formula III above, adamantane dimer of Formula IX above, and at least one adamantane oligomer or polymer of Formula IV above where at least one of h, i, and j is at least 1. Preferably, the thermosetting component comprises diamantane monomer of Formula IV above, diamantane dimer of Formula X above, and at least one diamantane oligomer or polymer of Formula VI above where at least one of h, i, and j is at least 1.

Preferably, the thermosetting component comprises adamantane monomer of Formula II above, adamantane dimer of Formula IX above, adamantane trimer of Formula XI above, and at least one adamantane oligomer or polymer of Formula IV above where at least one of i and j is at least 1. Preferably, the thermosetting component comprises diamantane monomer of Formula V above, diamantane dimer of Formula X above, diamantane trimer of Formula XII above, and at least one diamantane oligomer or polymer of Formula VI above where at least one of i and j is at least 1.

The thermosetting component comprises adamantane monomer of Formula III that is a tetrasubstituted adamantane or a diamantane monomer of Formula V that is a tetrasubstituted diamantane. The preferred monomer is the adamantane monomer of Formula III. The adamantane framework carries a substituted aryl radical in each of positions 1, 3, 5, and 7. The compound with the Formula IV is an oligomer or polymer, linked via unsubstituted and/or substituted aryl units, of the adamantane monomer of Formula III. The compound with the Formula VI is an oligomer or polymer, linked via unsubstituted and/or substituted aryl units, of the diamantane monomer of Formula V. Generally, h, i, and j are whole numbers from 0 to 10, preferably 0 to 5, and more preferably 0 to 2. The simplest adamantane oligomer is thus the dimer (h is 0, i is 0, and j is 0 in Formula IV) as shown in Formula IX above, in which two adamantane frameworks are linked via an unsubstituted or substituted aryl unit. The simplest diamantane oligomer is thus the dimer (h is 0, i is 0, and j is 0 in Formula VI) as shown in Formula X above, in which two diamantane frameworks are linked via an unsubstituted or substituted aryl unit.

In another embodiment, preferably the present thermosetting component comprises at least one adamantane oligomer or polymer of Formula IV above where h is from 0 to 10, i is from 0 to 10, and j is from 0 to 10. Preferably, the present thermosetting component comprises at least one diamantane oligomer or polymer of Formula VI above where h is from 0 to 10, i is from 0 to 10, and j is from 0 to 10.

Preferably, the present thermosetting component comprises at least one adamantane oligomer or polymer of Formula IV above where h is 0 or 1, i is 0, and j is 0. This adamantane structure is shown as Formula VII above.

Preferably, the present thermosetting component comprises at least one diamantane oligomer or polymer of Formula VI above where h is 0 or 1, i is 0, and j is 0. This diamantane structure is shown as Formula VIII above.

Preferably, the thermosetting component comprises at least one adamantane oligomer or polymer of Formula IV above where h is 0, i is 0, and j is 0. This adamantane dimer is shown as Formula IX above.

Preferably, the thermosetting component comprises at least one diamantane oligomer or polymer of Formula VI above where h is 0, i is 0, and j is 0. This diamantane dimer is shown as Formula X above.

Preferably, the thermosetting component comprises at least one adamantane oligomer or polymer of Formula IV above where h is 1, i is 0, and j is 0. This adamantane trimer is as shown in Formula XI above.

Preferably, the thermosetting component (a) comprises at least one diamantane oligomer or polymer of Formula VI above where h is 1, i is 0, and j is 0. This diamantane trimer is as shown in Formula XII above.

Preferably, the thermosetting component comprises a mixture of at least one adamantane oligomer or polymer of Formula IV above where h is 2, i is 0, and j is 0 (linear oligomer or polymer) and h is 0, i is 1, and j is 0 (branched oligomer or polymer). Thus, this composition comprises a mixture of an adamantane linear tetramer as shown in Formula XIII below

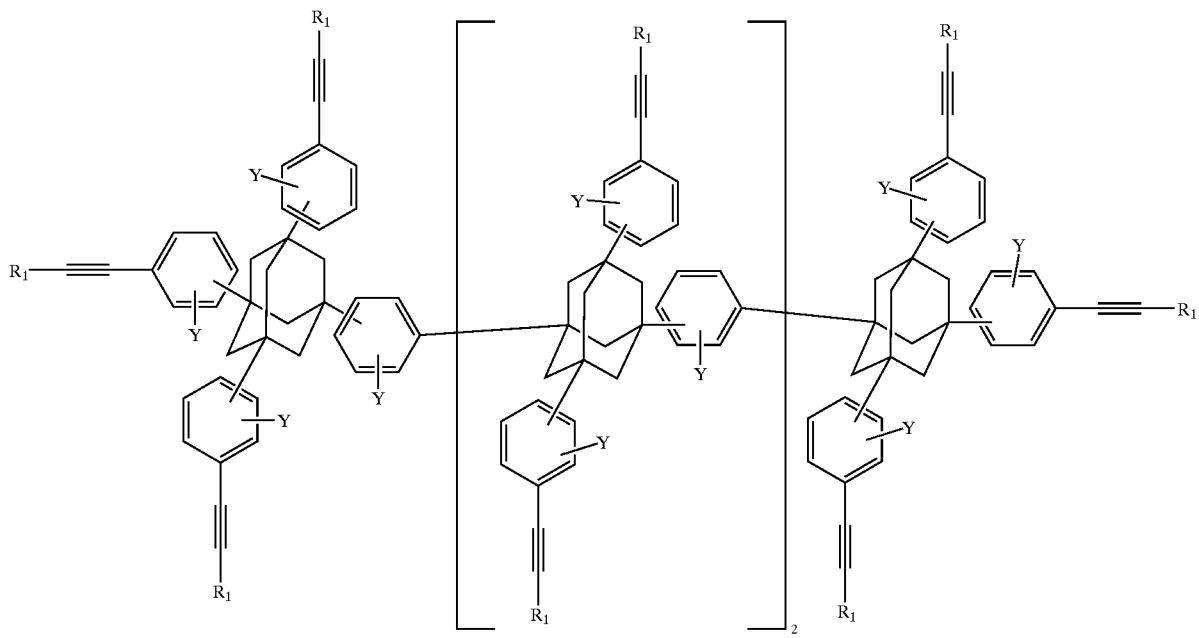
and adamantane branched tetramer as shown Formula XIV below
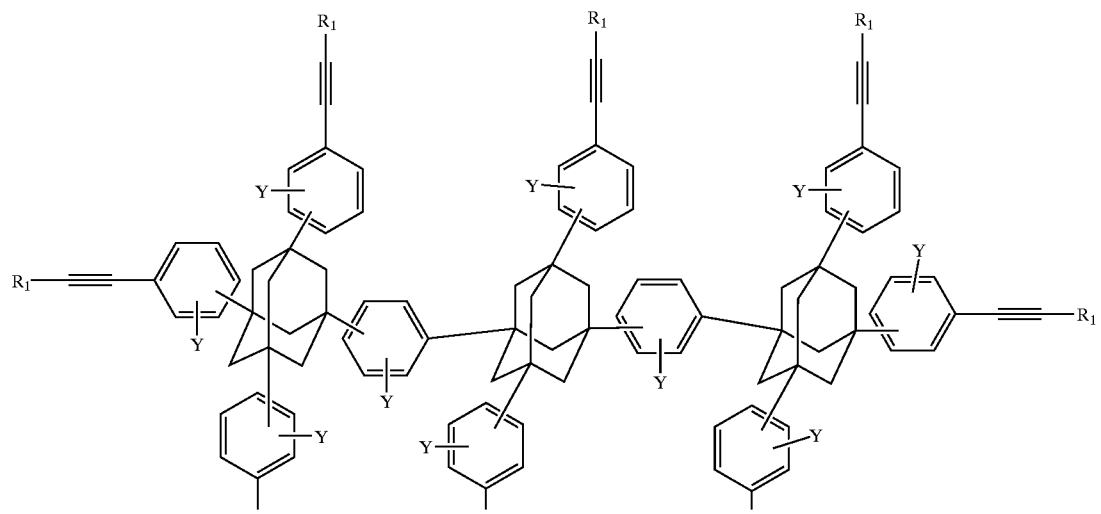

-continued
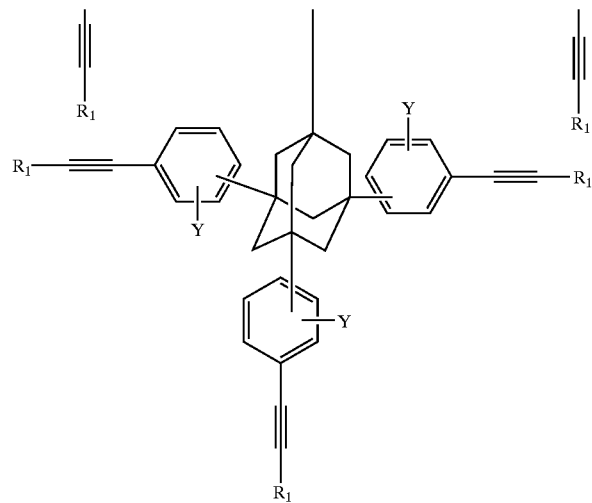
Preferably, the thermosetting component comprises at least one diamantane oligomer or polymer of Formula VI above where h is 2, i is 0, and j is 0 (linear oligomer or polymer) and h is 0, i is 1, and j is 0 (branched oligomer or polymer). Thus, the present composition comprises diamantane linear tetramer as shown in Formula XV below
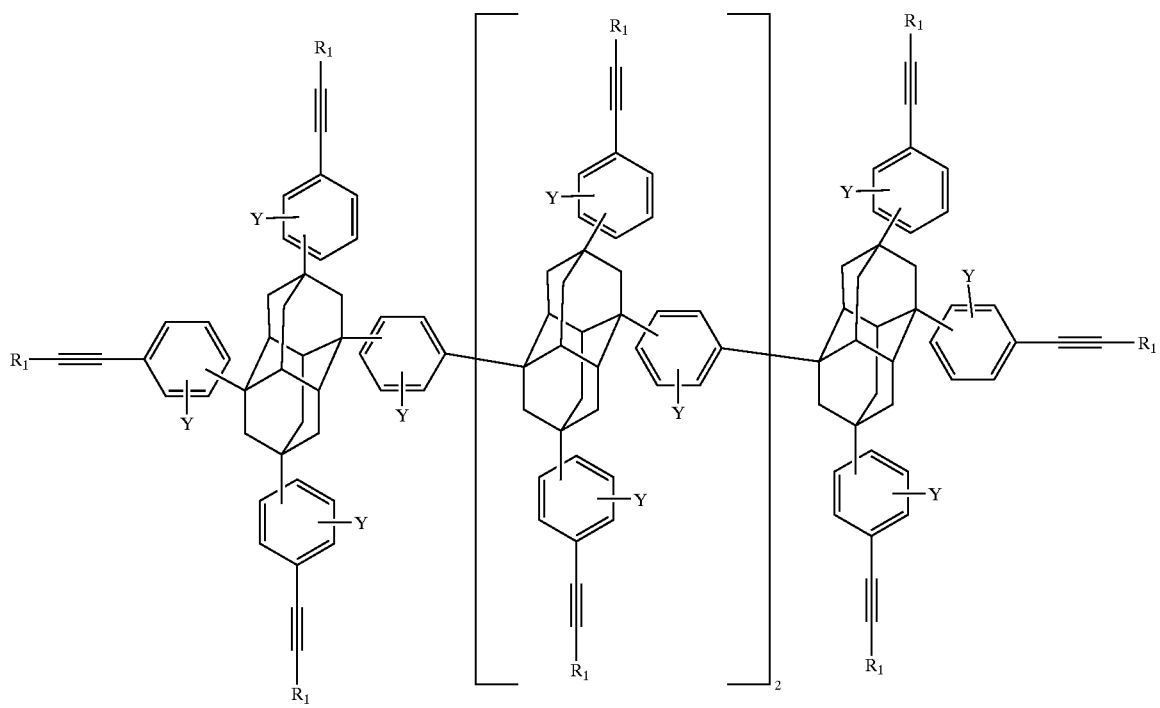

and diamantane branched tetramer as shown Formula XVI below

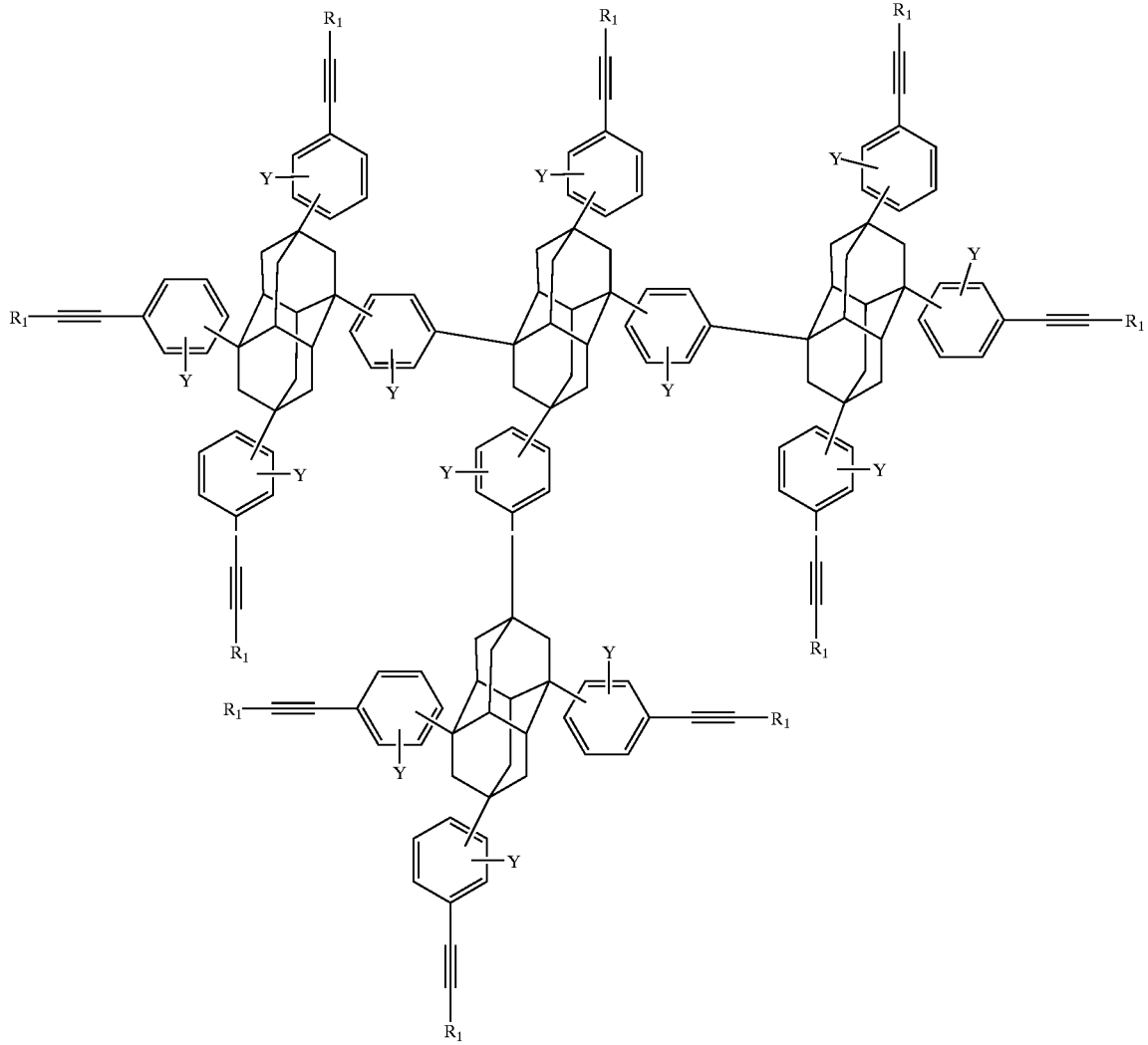

Preferably, the thermosetting component comprises adamantane dimer of Formula IX above and adamantane trimer of Formula XI above. Preferably, the thermosetting component comprises diamantane dimer of Formula X above and diamantane trimer of Formula XII above.

Preferably, the thermosetting component comprises adamantane dimer of Formula IX above and at least one adamantane oligomer or polymer of Formula IV above where h is 0, i is at least 1, and j is 0. Preferably, the thermosetting component comprises diamantane dimer of Formula X above and at least one diamantane oligomer or polymer of Formula VI above where h is 0, i is at least 1, and j is 0.

In both embodiments, for Formulae I and II above, preferred Q groups include aryl and aryl substituted with alkenyl and alkynyl groups and more preferred Q groups include (phenylethynyl)phenyl, phenylethynyl (phenylethynyl)phenyl, and (phenylethynyl)phenylphenyl moiety. Preferred aryls for G include phenyl, biphenyl, and terphenyl. The more preferred G group is phenyl.

The individual radicals $R_1$ of the substituted ethynyl radical on the phenyl ring attached to the adamantane or diamantane ring of the type $R_1\equiv C-$ are in each case the same or different in Formulae III, IV, V, VI, VII, VII, IX, X, XI, XII, XII, XIV, XV, and XVI above. $R_1$ is selected from hydrogen, halogen, alkyl, aryl, substituted aryl, heteroaryl, aryl ether, alkenyl, alkynyl, alkoxyl, hydroxyalkyl, hydroxyaryl, hydroxyalkenyl, hydroxyalkynyl, hydroxyl, or carboxyl. Each $R_1$ may be unbranched or branched and unsubstituted or substituted and the substituents may be unbranched or branched. It is preferred that the radicals alkyl, alkenyl, alkynyl, alkoxyl, hydroxyalkyl, hydroxyalkenyl, and hydroxyalkynyl contain from about 2 to about 10 carbon atoms and the radicals aryl, aryl ether, and hydroxyaryl contain from about 6 to about 18 carbon atoms. If $R_1$ stands for aryl, $R_1$ is preferably phenyl. Preferably, at least two of the $R_1C\equiv C$ groups on the phenyl groups are two different isomers. Examples of at least two different isomers include meta-, para-, and ortho-isomers. Preferably, the at least two different isomers are meta- and para-isomers. In the preferred monomer, 1,3,5,7-tetrakis[3'/4'-phenylethynyl)phenyl]adamantane (shown in FIG. 1D), five isomers form: (1) para-, para-, para-, para-; (2) para-, para-, para-, meta-; (3) para-, para-, meta-, meta-; (4) para-, meta-, meta-, meta-; and (5) meta-, meta-, meta-, meta-.

Each Y of the phenyl rings in the Formulae III, IV, V, VI, VII, VIII, IX, X, XI, XII, XIII, XIV, XV, and XVI above is in each case the same or different and selected from hydrogen, alkyl, aryl, substituted aryl, or halogen. When Y is aryl, examples of aryl groups include phenyl or biphenyl. Y is selected from preferably hydrogen, phenyl, and biphenyl and more preferably hydrogen. Preferably, at least one of the phenyl groups between two bridgehead carbons of adamantane or diamantane exists as at least two different isomers. Examples of at least two different isomers include meta-, para-, and ortho-isomers. Preferably, the at least two isomers are meta- and para-isomers. In the most preferred dimer 1,3/4-bis{1',3',5'-tris[3"/4"-(phenylethynyl)phenyl]adamant-7'-yl}benzene (shown in FIG. 1F), 14 isomers form as follows. Preferably, the phenyl group located between the two bridgehead carbons of the adamantane exists as meta- and para-isomers. For each of the two preceding isomers, seven isomers of the $R_1C{\equiv}C$ groups on the phenyl groups exist as follows: (1) para-, para-, para-, para-, para-, para-; (2) para-, para-, para-, para-, para-, meta-; (3) para-, para-, para-, para-, meta-, meta-; (4) para-, para-, para-, meta-, meta-, meta-; (5) para-, para-, meta-, meta-, meta-, meta-; (6) para-, meta-, meta-, meta-, meta-, meta-, and (7) meta-, meta-, meta-, meta-, meta-, meta-.

In addition to the branched adamantane structure of Formula XIV above, it should be understood that Formula IV above when h is 0, i is 0, and j is 1 represents further branching as shown in Formula XVII below. It should be understood that branching may occur beyond that of the Formula XVII structure because further branching of the pending adamantane units of the Formula XVII structure may also occur.

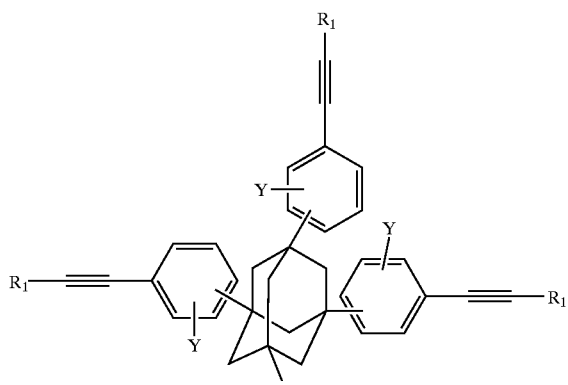

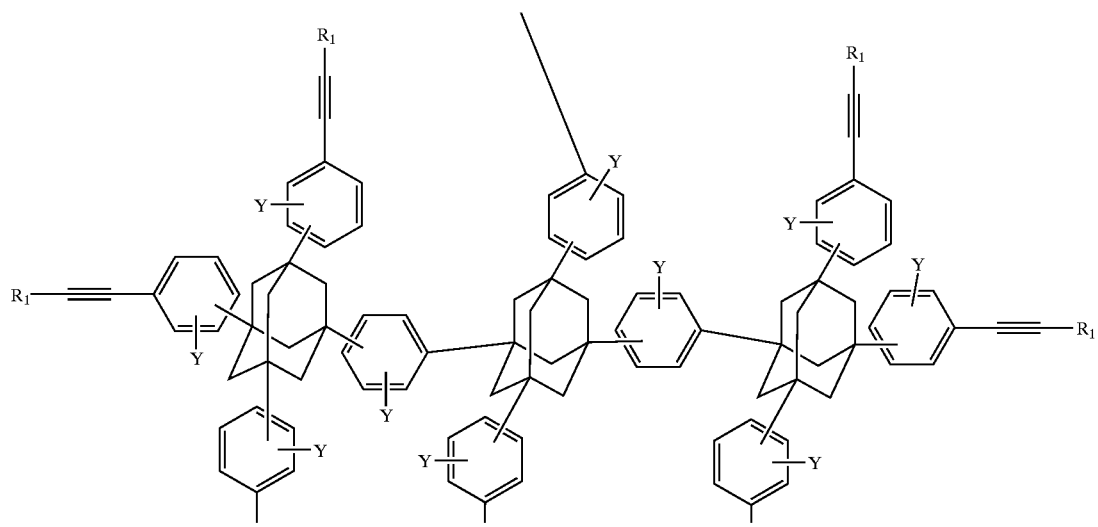

-continued

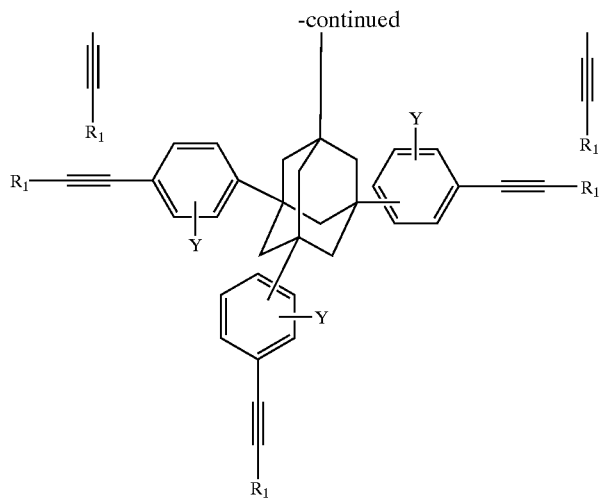

In addition to the branched diamantane structure of Formula XVI above, it should be understood that Formula VI above when h is 0, i is 0, and j is 1 represents further branching as shown in Formula XVIII below. It should be understood that branching may occur beyond that of the Formula XVIII structure because further branching of the pending diamantane units of the Formula XVIII structure may also occur.

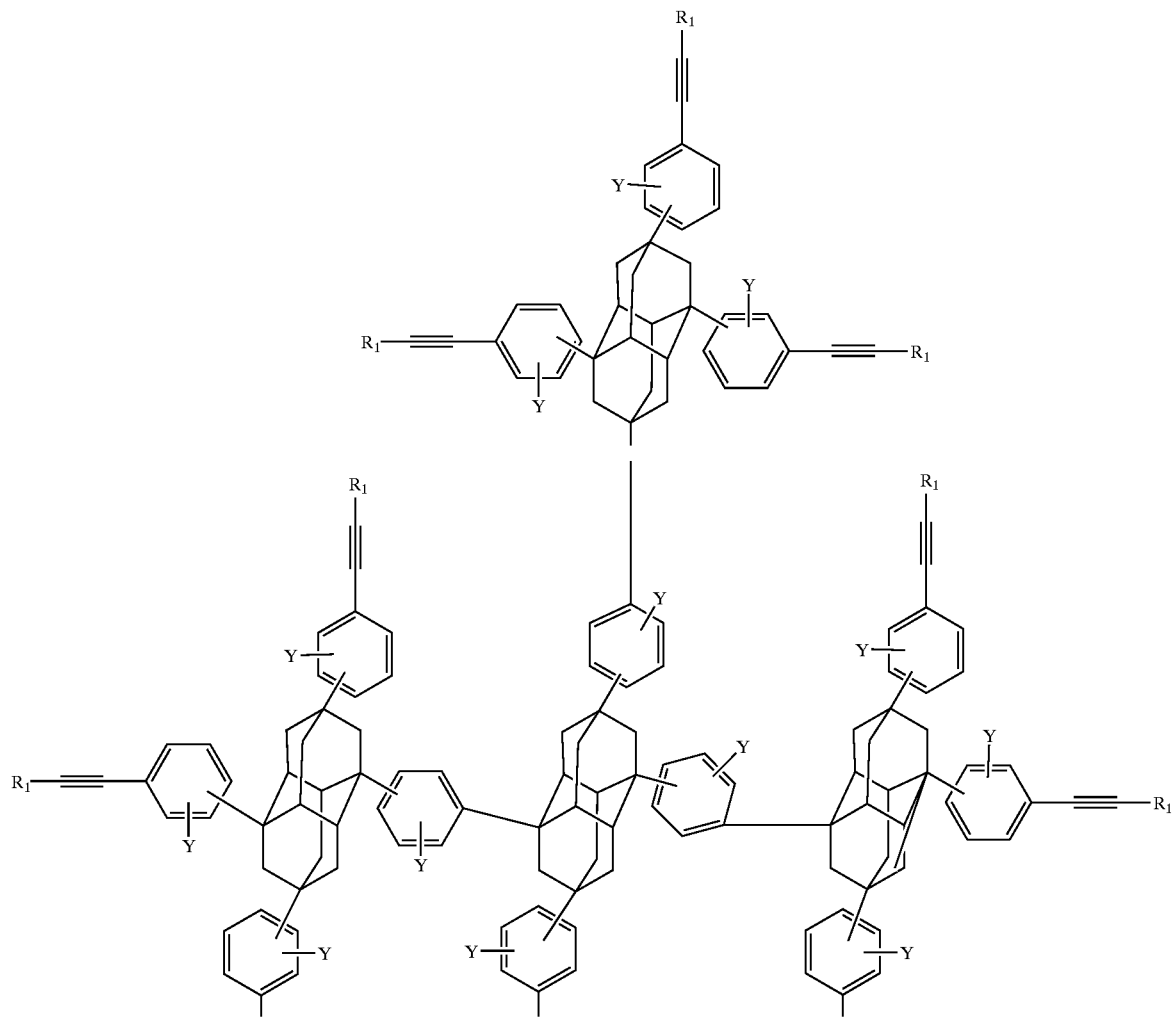

-continued

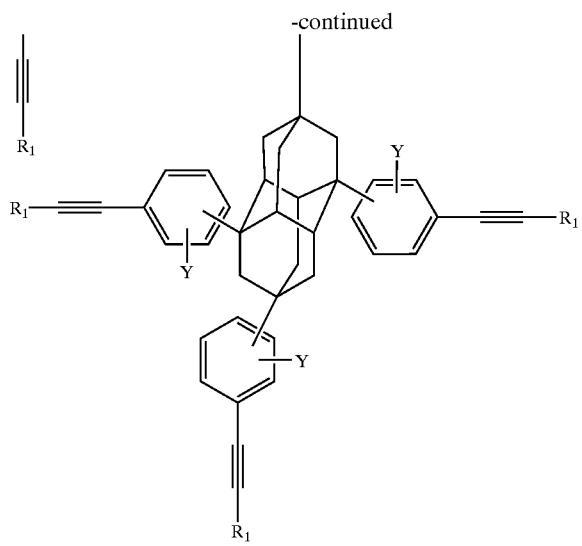

In thermosetting component, the monomer and oligomer or polymer contents are determined by the gel permeation chromatography techniques set forth below in the Analytical Test Methods section. The present composition comprises the adamantane or diamantane monomer in a quantity of about 30 to about 70 area-%, more preferably about 40 to about 60 area-% and even more preferably about 45 to about 55 area-% and the oligomer or polymer in a quantity of about 70 to about 30 area-%, more preferably about 60 to about 40 area-%, and even more preferably about 55 to about 45 area-%. Most preferably, the present composition comprises the monomer (1) in a quantity of approximately 50 area-% and the oligomer or polymer (2) in a quantity of approximately 50 area-%.

The Analytical Test Methods section sets forth two Gel Permeation Chromatography Methods. Both provide similar results. One skilled in the art may elect to use the second method in that it yields additional detail on the dimer and trimer.

In general, the quantity ratio of the adamantane or diamantane monomer (1) to oligomer or polymer (2) can be set in a desired manner, e.g. by altering the molar ratio of the starting components during the preparation of the composition according to the invention, by adjusting reaction conditions, and by altering the ratio of nonsolvent to solvent during precipitation/isolation steps.

A preferred process for preparing the thermosetting component (a) comprises the following steps.

In step (A), adamantane or diamantane is reacted with halogeno benzene compound of Formula XIX

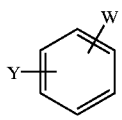

where W is halogen, to form a mixture which if adamantane is used, comprises at least one monomer of Formula XX

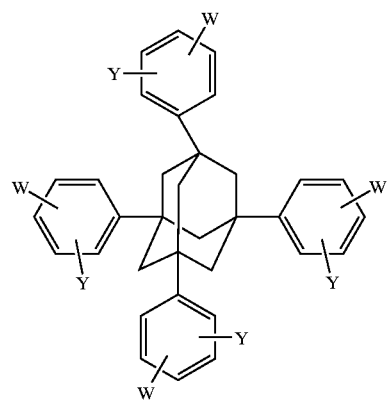

and at least one oligomer or polymer of Formula XXI where h is from 0 to 10, i is from 0 to 10, and j is from 0 to 10

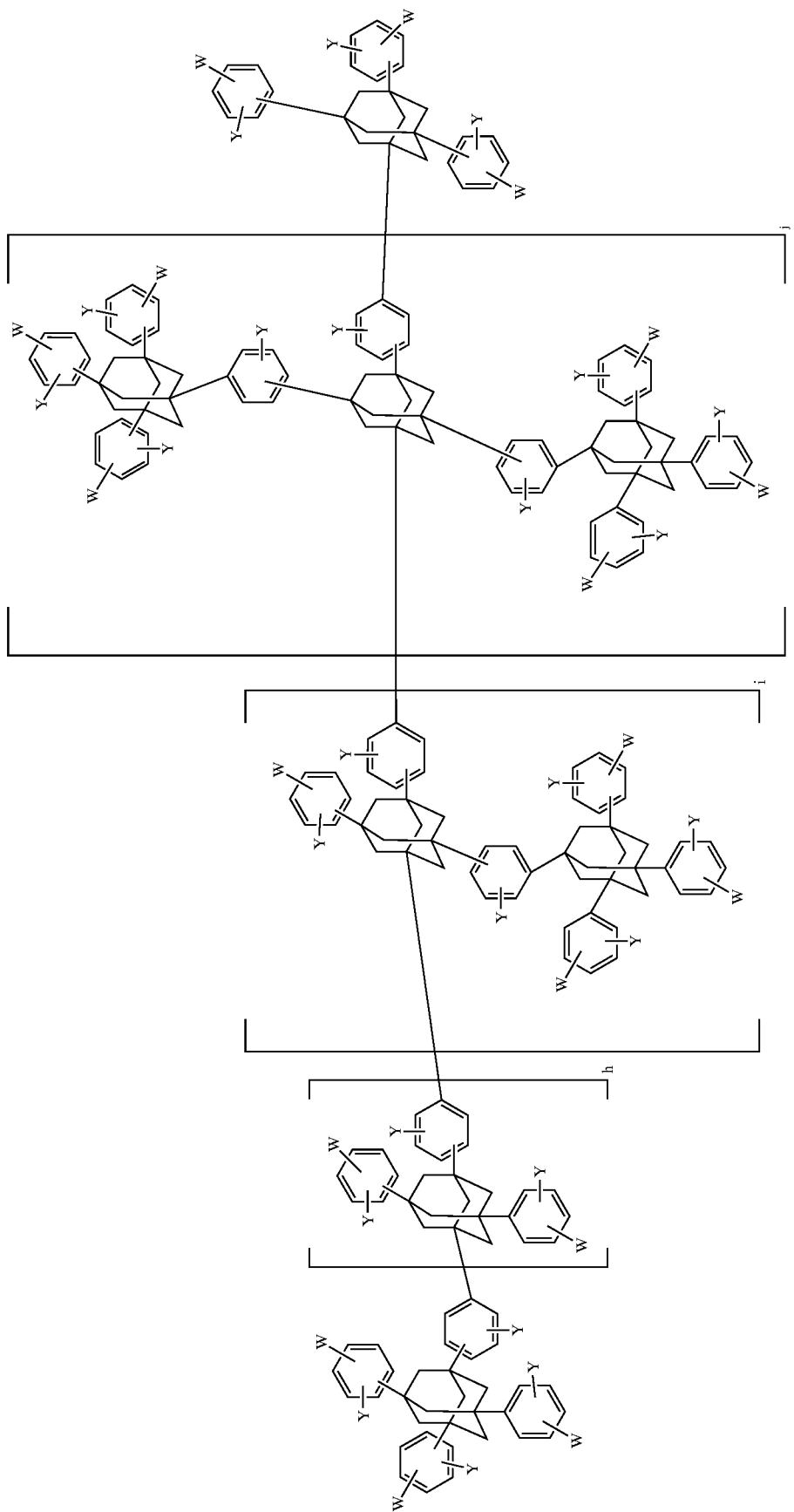

or if diamantane is used, comprises at least one monomer of Formula XXII
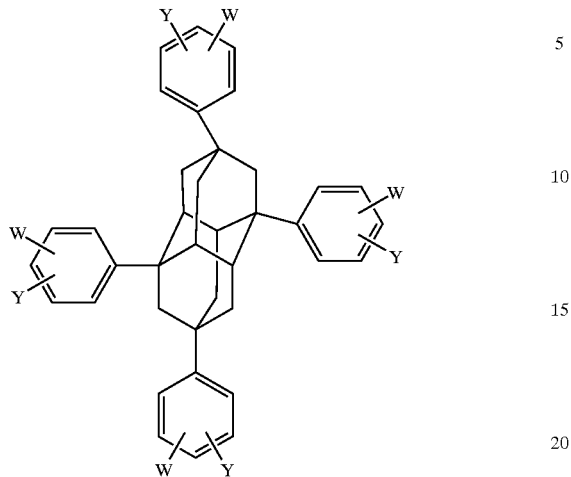
and at least one oligomer or polymer of Formula XXIII where h is from 0 to 10, i is from 0 to 10, and j is from 0 to 10

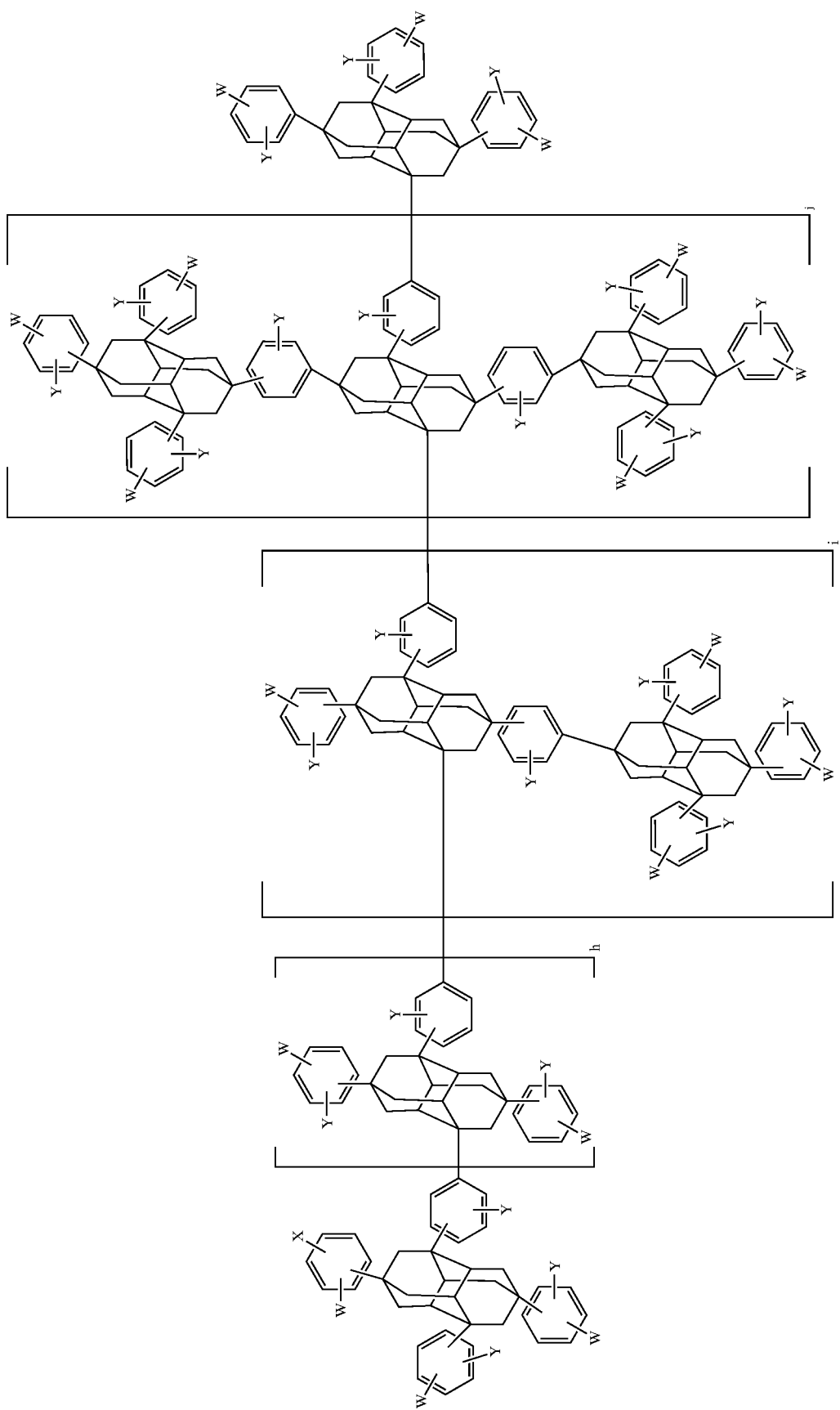

It should be understood to those skilled in the art that reaction may occur on diamantane at bridgehead carbons other than those indicated in Formulae XXII and XXIII above.

In step (B), the mixture resulting from step (A) is reacted with terminal alkyne of the formula $R_1C \equiv CH$. Preferably, the present process forms compositions of Formulae III and IV or V and VI above.

In step (A), adamantane or diamantane is reacted with halogeno benzene compound with the Formula XIX. In addition to the halogen radical W and the previously described radical Y, the halogeno benzene compound can also contain further substituents.

The halogeno benzene compound is preferably selected from bromobenzene, dibromobenzene, and iodobenzene. Bromobenzene and/or dibromobenzene are preferred, bromobenzene being even more preferred.

The reaction of adamantane or diamantane with the halogeno benzene compound (step (A)) takes place preferably through Friedel-Crafts reaction in the presence of a Lewis acid catalyst. Although all customary Lewis acid catalysts may be used, it is preferred that the Lewis acid catalyst contains at least one compound selected from aluminum(III) chloride ($AlCl_3$), aluminum(III) bromide ($AlBr_3$), and aluminum (III) iodide ($AlI_3$). Aluminum(III) chloride ($AlCl_3$) is most preferred. Despite the greater Lewis acidity of aluminum(III) bromide, its use is generally less preferred, because it has a low sublimation point of only 90° C. and is thus much more difficult to handle on an industrial scale than e.g. aluminum(III) chloride.

In a further preferred version, the Friedel-Crafts reaction is carried out in the presence of a second catalyst component. The second catalyst component preferably contains at least one compound selected from tertiary halogen alkane with 4 to 20 carbon atoms, tertiary alkanol with 4 to 20 carbon atoms, secondary and tertiary olefin with 4 to 20 carbon atoms and tertiary halogen alkyl aryl compound. In particular, the second catalyst component contains at least one compound selected from 2-bromo-2-methylpropane (tert.-butyl bromide), 2-chloro-2-methylpropane (tert.-butyl chloride), 2-methyl-2-propanol (tert.-butyl alcohol), isobutene, 2-bromopropane, and tert.-butylbromobenzene, with 2-bromo-2-methylpropane (tert.-butyl bromide) being most preferred. Overall, compounds whose alkyl groups include 5 or more carbon atoms are less suitable, as solid constituents precipitate out of the reaction solution at the end of the reaction.

It is most preferred that the Lewis acid catalyst is aluminum(III) chloride ($AlCl_3$) and the second catalyst component is 2-bromo-2-methylpropane (tert.-butyl bromide) or tert.-butylbromobenzene.

The preferable procedure for carrying out the Friedel-Crafts reaction is that adamantane or diamantane, halogeno benzene compound (e.g. bromobenzene), and Lewis acid catalyst (e.g. aluminium chloride) are mixed and heated at a temperature of 30° C. to 50° C., preferably 35° C. to 45° C. and in particular 40° C. At temperatures lower than 30° C., the reaction is not completed, i.e. a higher proportion of tri-substituted adamantane forms for example. In principle it is conceivable to use even higher temperatures than those given above (e.g. 60° C.), but this leads in an undesirable manner to a higher proportion of non-halogenated aromatic material (e.g. benzene) in the reaction mixture of step (A). The second component of the catalyst system, say tert.-butyl bromide, is then added to the above reaction solution generally over a period of 5 to 10 hours, preferably 6 to 7 hours and after the addition has ended, mixed into the reaction mixture in the temperature range named above customarily for a further 5 to 10 hours, preferably 7 hours.

Surprisingly, in addition to the monomeric tetraphenylated compound, e.g. 1,3,5,7-tetrakis(3'/4'-bromophenyl) adamantane, oligomers or polymers thereof were also found in the mixture obtained after step (A). It was wholly unexpected that the quantity ratio of adamantane monomer of Formula XX to adamantane oligomer or polymer of Formula XXI or diamantane monomer of Formula XXII to diamantane oligomer or polymer of Formula XXIII was controllable through the quantities of adamantane or diamantane, halogeno benzene compound (e.g. bromobenzene), and second catalyst component (e.g. tert.-butyl bromide) used. The molar ratio of adamantane or diamantane to halogeno benzene compound to second catalyst component in the reaction mixture of step (A) is preferably 1:(5–15):(2–10) and even more preferably 1:(8–12):(4–8).

In the compounds with the Formulae XX, XXI, XXII, and XXIII, the position of the halogen substituent W is undefined. Preferably, the mixtures comprise meta- and para-isomers which, unlike all para-isomers, advantageously produce improved solubility and good film properties. In the reaction mixture of step (A), in addition to monomers and oligomers or polymers, starting components and by-products, such as not wholly phenylated adamantanes, can also occur.

The mixture resulting from step (A) is optionally worked up using methods known to those skilled in the art. For example, it may be necessary to remove non-reacted halogen phenyl compound, say bromobenzene, from the mixture in order to obtain a product, usable for further reaction, with a high proportion of compounds of Formulae XX, XXI, XXII, and XXIII. Any solvent or solvent mixture which is miscible with the halogeno benzene compound, say bromobenzene, and is suitable for the precipitation of the compounds of Formulae XX, XXI, XXII, and XXIII may be used for the isolation of such a product. It is preferred to introduce the mixture resulting from step (A) into a nonpolar solvent or solvent mixture, e.g. by dropping in, with preference being given to the use of aliphatic hydrocarbons with 7 to 20 carbon atoms or mixtures thereof and in particular at least one component selected from heptane fraction (boiling point 93–99° C.), octane fraction (boiling point 98–110° C.) and alkane mixture currently commercially available from Honeywell International Inc. under the tradename Spezial Benzin 80–110° C. (petroleum ether with boiling point of 80–110° C.). Spezial Benzin 80–110° C. (petroleum ether with boiling point of 80–110° C.) is most preferred. The weight ratio of organic mixture to nonpolar solvent is preferably about 1:2 to about 1:20, more preferably about 1:5 to about 1:13, and even more preferably about 1:7 to about 1:11. Alternatively, a polar solvent or solvent mixture (e.g. methanol or ethanol) can be used for the working-up of the mixture obtained after step (A), but it is less preferred, as the product mixture then precipitates out as a rubbery composition.

We have found that the peak ratio of monomer resulting from step (A) above to its dimer and trimer and oligomer in the reaction mixture shifts dramatically if the step (A) mixture is precipitated into certain solvents. This discovery advantageously allows one skilled in the art to adjust process conditions in order to achieve a targeted ratio of monomer to dimer and trimer and oligomer. To reduce this ratio, preferably, a solvent is used in which the monomer and oligomer or polymer have different solubilities.

Preferred solvents for achieving this monomer to dimer and trimer ratio shift include Spezial Benzin 80–110° C.

(petroleum ether with boiling point of 80° C.–110° C.), ligroine (boiling point 90–110° C.), and heptane (boiling point 98° C.). The more preferred solvent is Spezial Benzin. More specifically, to achieve a shift from about 3:1 monomer:dimer+trimer+oligomer to about 1:1, the step (A) mixture is precipitated into Spezial Benzin or to attain a shift from about 3:1 monomer:dimer+trimer+oligomer to about 1.7–2.0:1.0, the step (A) reaction mixture is precipitated into ligroine and heptane. We know that these substantial changes in peak distribution at precipitation are explained by the loss of monomer in the precipitation filtrates: ⅔ loss in Spezial Benzin and ≧⅓ loss in ligroine and heptane, which correspond to monomer yield losses of 50 and 25–33%. In order for the ratio monomer:dimer+trimer+oligomer 3:1 to remain unchanged, the step (A) reaction mixture is precipitated into methanol where no yield losses are observed. This is corroborated by determination of yield losses of the filtrates and GPC analysis of the filtrates.

Like the synthesis described by Ortiz, the Friedel-Crafts reaction which is carried out according to a preferred version in step (A) of the present process starts direct from adamantane which is coupled with the halogeno benzene compound. Compared with previous syntheses of e.g. 1,3,5,7-tetrakis(3'/4'-bromophenyl)adamantane by Reichert et al., the present process is particularly advantageous because it is no longer necessary to produce tetrabrominated adamantanes first, which saves a reaction step. Also, less unwanted benzene forms.

It is known to those skilled in the art that the halogen radical W in the compounds of Formulae XX, XXI, XXII, and XXIII above can also be introduced, apart from a direct reaction of adamantane with halogen phenyl compound (e.g. with the help of a Friedel-Crafts reaction), by a multi-stage synthesis, for example, by coupling adamantane with a phenyl compound (i.e. without halogen radical W) followed by introduction of the radical W say through addition with $W_2$ (e.g. $Br_2$) although this is not preferred.

In step (B) of the preferred process, the (optionally worked-up) mixture obtained after step (A) is reacted with terminal alkyne of the formula $R_1C\equiv CH$ where $R_1$ is as previously defined.

In the formula $R_1C\equiv CH$, $R_1$ is identical with the previously described radical $R_1$ of the adamantane product of Formulae III and IV and the diamantane product of Formulae V and VI. Accordingly it is most preferred to use ethynyl benzene (phenylacetylene) as terminal alkyne for the reaction in step (B).

In order, in step (B), to couple the terminal alkyne to the halogeno benzene radicals located at the adamantane system, all conventional coupling methods suitable for this purpose may be used, as described for example in Diederich, F., and Stang, P. J., (Eds.) "Metal-Catalyzed Cross-Coupling Reactions", Wiley-VCH 1998 and March, J., "Advanced Organic Chemistry", 4th Edition, John Wiley & Sons 1992, pages 717/718.

When Y on the phenyl groups is attached to two cage structure bridgehead carbons in Formula XXI above or in Formula XXIII above, Y may react with phenylacetylene to generate terminal alkyne groups.

In a preferred version of the process according to the invention, the reaction of the (optionally worked-up) mixture obtained after step (A) with terminal alkyne is carried out in the presence of a catalyst system as used in the so-called Sonogashira coupling (cf. Sonogashira; Tohda; Hagihara; Tetrahedron Lett. 1975, page 4467). It is even more preferred to use a catalyst system which in each case contains at least one palladium-triarylphosphine complex with the formula $[Ar_3P]_2PdX_2$ (where Ar=aryl and X=halogen), a copper halide (e.g. CuI), a base (e.g. a trialkylamine), a triarylphosphine and a co-solvent. According to the invention, this preferred catalyst system can equally well consist of the named components. The co-solvent preferably contains at least one component selected from toluene, xylene, chlorobenzene, N,N-dimethylformamide and 1-methyl-2-pyrrolidone (N-methylpyrrolidone (NMP)). A catalyst system which contains the components bis-(triphenylphosphine)palladium (II)dichloride (i.e. $[Ph_3P]_2PdCl_2$), triphenylphosphine (i.e. $[Ph_3P]$), copper(I)-iodide, triethylamine and toluene as co-solvent is most preferred.

The preferred procedure for the reaction of the mixture obtained from step (A) (and optionally worked-up) with terminal alkyne is that the mixture is first mixed with the base (e.g. triethylamine) and the co-solvent (e.g. toluene) and this mixture is stirred for some minutes at room temperature. The palladium-triphenylphosphine complex (e.g. $Pd(PPh_3)_2Cl_2$), triphenylphosphine ($PPh_3$) and copper halide (e.g. copper(I)-iodide) are then added, and this mixture is heated in a temperature range of 50° C. to 90° C. (more preferably 80° C. to 85° C.). Terminal alkyne is then added in the named temperature range within 1 to 20 hours (more preferably 3 hours). After the ending of the addition, the mixture is heated for at least 5 to 20 hours (more preferably 12 hours) at a temperature of 75° C. to 85° C. (more preferably 80° C.). Solvent is then added to the reaction solution and distilled off under reduced pressure. Preferably, after filtration, the reaction solution is then cooled to a temperature of 20° C. to 30° C. (more preferably 25° C.). Finally, the reaction mixture of step (B), in particular for the removal of metal traces (e.g. Pd), is worked up with conventional methods which are known to those skilled in the art.

The peak ratio of monomer resulting from step (B) above to its dimer and trimer and oligomer in the reaction mixture shifts if the step (B) mixture is precipitated into certain solvents.

Surprisingly, it transpired that the reaction sequence starting direct from adamantane leads to an oligomeric or polymeric content in the reaction product of step (A) which can be controlled via the use ratio of adamantane, halogeno benzene compound and the second catalyst component, say tert.-butyl bromide. In corresponding manner, the benzene content in the reaction mixture of step (A) is also successfully regulated via this use ratio, which, because of the toxicity of benzene in industrial-scale syntheses, is of great importance. The oligomeric or polymeric content permits the same secondary chemistry as the monomer (e.g. 1,3,5,7-tetrakis(3'/4'-bromophenyl)adamantane, i.e. the oligomer or polymer is just as accessible as the monomer for the reaction with the terminal alkyne in step (B)).

Adhesion Promoter:

The phrase "adhesion promoter" as used herein means any component that when added to thermosetting component, improves the adhesion thereof to substrates compared with thermosetting component alone.

The phrase "compound having at least bifunctionality" as used herein means any compound having at least two functional groups capable of interacting or reacting, or forming bonds as follows. The functional groups may react in numerous ways including addition reactions, nucleophilic and electrophilic substitutions or eliminations, radical reactions, etc. Further alternative reactions may also include the formation of non-covalent bonds, such as Van der Waals, electrostatic bonds, ionic bonds, and hydrogen bonds.

Adhesion promoter is disclosed in our commonly assigned pending patent application Ser. No. 60/350187 filed Jan. 15, 2002 which is incorporated herein by reference in its entirety.

In the adhesion promoter, preferably at least one of the first functionality and the second functionality is selected from Si containing groups; N containing groups; C bonded to O containing groups; hydroxyl groups; and C double bonded to C containing groups. Preferably, the Si containing groups are selected from Si—H, Si—O, and Si—N; the N containing groups are selected from such as C—NH$_2$ or other secondary and tertiary amines, imines, amides, and imides; the C bonded to O containing groups are selected from =CO, carbonyl groups such as ketones and aldehydes, esters, —COOH, alkoxyls having 1 to 5 carbon atoms, ethers, glycidyl ethers; and epoxies; the hydroxyl group is phenol; and the C double bonded to C containing groups are selected from allyl and vinyl groups. For semiconductor applications, the more preferred functional groups include the Si containing groups; C bonded to O containing groups; hydroxyl groups; and vinyl groups.

An example of a preferred adhesion promoter having Si containing groups is silanes of the Formula XXIV: $(R_2)_k(R_3)_l Si(R_4)_m(R_5)_n$ wherein $R_2$, $R_3$, $R_4$, and $R_5$ each independently represents hydrogen, hydroxyl, unsaturated or saturated alkyl, substituted or unsubstituted alkyl where the substituent is amino or epoxy, saturated or unsaturated alkoxyl, unsaturated or saturated carboxylic acid radical, or aryl; at least two of $R_2$, $R_3$, $R_4$, and $R_5$ represent hydrogen, hydroxyl, saturated or unsaturated alkoxyl, unsaturated alkyl, or unsaturated carboxylic acid radical; and $k+l+m+n \leq 4$. Examples include vinylsilanes such as $H_2C=CHSi(CH_3)_2H$ and $H_2C=CHSi(R_6)_3$ where $R_6$ is $CH_3O$, $C_2H_5O$, AcO $H_2C=CH$, or $H_2C=C(CH_3)O$—, or vinylphenylmethylsilane; allylsilanes of the formula $H_2C=CHCH_2$—Si$(OC_2H_5)_3$ and $H_2C=CHCH_2$—Si(H)(OCH$_3$)$_2$ glycidoxypropylsilanes such as (3-glycidoxypropyl)methyidiethoxysilane and (3-glycidoxypropyl)trimethoxysilane; methacryloxypropylsilanes of the formula $H_2C=(CH_3)COO(CH_2)_3$—Si(OR$_7$)$_3$ where $R_7$ is an alkyl, preferably methyl or ethyl; aminopropylsilane derivatives including $H_2N(CH_2)_3Si(OCH_2CH_3)_3$, $H_2N(CH_2)_3Si(OH)_3$, or $H_2N(CH_2)_3OC(CH_3)_2CH=CHSi(OCH_3)_3$. The aforementioned silanes are commercially available from Gelest.

An example of a preferred adhesion promoter having C bonded to O containing groups is glycidyl ethers including but not limited to 1,1,1-tris-(hydroxyphenyl)ethane triglycidyl ether which is commercially available from TriQuest.

An example of a preferred adhesion promoter having C bonded to O containing groups is esters of unsaturated carboxylic acids containing at least one carboxylic acid group. Examples include trifunctional methacrylate ester, trifunctional acrylate ester, trimethylolpropane triacrylate, dipentaerythritol pentaacrylate, and glycidyl methacrylate. The foregoing are all commercially available from Sartomer.

An example of a preferred adhesion promoter having vinyl groups is vinyl cyclic pyridine oligomers or polymers wherein the cyclic group is pyridine, aromatic, or heteroaromatic. Useful examples include but not limited to 2-vinylpyridine and 4-vinylpyridine, commercially available from Reilly; vinyl aromatics; and vinyl heteroaromatics including but not limited to vinyl quinoline, vinyl carbazole, vinyl imidazole, and vinyl oxazole.

An example of a preferred adhesion promoter having Si containing groups is the polycarbosilane disclosed in commonly assigned copending allowed U.S. patent application Ser. No. 09/471299 filed Dec. 23, 1999 incorporated herein by reference in its entirety. The polycarbosilane is of the Formula XXV:

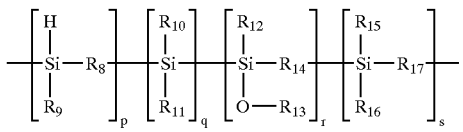

in which $R_8$, $R_{14}$, and $R_{17}$ each independently represents substituted or unsubsalltituted alkylene, cycloalkylene, vinylene, allylene, or arylene; $R_9$, $R_{10}$, $R_{11}$, $R_{10}$, $R_{15}$, and $R_{16}$ each independently represents hydrogen atom or organo group comprising alkyl, alkylene, vinyl, cycloalkyl, allyl, or aryl and may be linear or branched; $R_{13}$ represents organosilicon, silanyl, siloxyl, or organo group; and p, q, r, and s satisfy the conditions of [$4 \leq p+q+r+s \leq 100{,}000$], and q and r and s may collectively or independently be zero. The organo groups may contain up to 18 carbon atoms but generally contain from about 1 to about 10 carbon atoms. Useful alkyl groups include —CH$_2$— and —(CH$_2$)$_t$— where t>1.

Preferred polycarbosilanes of the present invention include dihydrido polycarbosilanes in which $R_8$ is a substituted or unsubstituted alkylene or phenyl, $R_9$ group is a hydrogen atom and there are no appendent radicals in the polycarbosilane chain; that is, q, r, and s are all zero. Another preferred group of polycarbosilanes are those in which the $R_9$, $R_{10}$, $R_{11}$, $R_{12}$, $R_{15}$, and $R_{16}$ groups of Formula XXV are substituted or unsubstituted alkenyl groups having from 2 to 10 carbon atoms. The alkenyl group may be ethenyl, propenyl, allyl, butenyl or any other unsaturated organic backbone radical having up to 10 carbon atoms. The alkenyl group may be dienyl in nature and includes unsaturated alkenyl radicals appended or substituted on an otherwise alkyl or unsaturated organic polymer backbone. Examples of these preferred polycarbosilanes include dihydrido or alkenyl substituted polycarbosilanes such as polydihydridocarbosilane, polyallylhydrididocarbosilane and random copolymers of polydihydridocarbosilane and polyallylhydridocarbosilane.

In the more preferred polycarbosilanes, the $R_9$ group of Formula XXV is a hydrogen atom and $R_8$ is methylene and the appendent radicals q, r, and s are zero. Other preferred polycarbosilane compounds of the invention are polycarbosilanes of Formula XXV in which $R_9$ and $R_{15}$ are hydrogen, $R_8$ and $R_{17}$ are methylene, and $R_{16}$ is an alkenyl, and appendent radicals q and r are zero. The polycarbosilanes may be prepared from well known prior art processes or provided by manufacturers of polycarbosilane compositions. In the most preferred polycarbosilanes, the $R_9$ group of Formula XXV is a hydrogen atom; $R_8$ is —CH$_2$—; q, r, and s are zero and p is from 5 to 25. These most preferred polycarbosilanes may be obtained from Starfire Systems, Inc. Specific examples of these most preferred polycarbosilanes follow:

| Polycarbosilane | Weight Average Molecular Weight (Mw) | Polydispersity | Peak Molecular Weight (Mp) |
|---|---|---|---|
| 1 | 400–1,400 | 2–2.5 | 330–500 |
| 2 | 330 | 1.14 | 320 |

-continued

| Polycarbosilane | Weight Average Molecular Weight (Mw) | Polydispersity | Peak Molecular Weight (Mp) |
|---|---|---|---|
| 3 (with 10% allyl groups) | 10,000–14,000 | 10.4–16 | 1160 |
| 4 (with 75% allyl groups) | 2,400 | 3.7 | 410 |

As can be observed in Formula XXV, the polycarbosilanes utilized in the subject invention may contain oxidized radicals in the form of siloxyl groups when r>0. Accordingly, $R_{13}$ represents organosilicon, silanyl, siloxyl, or organo group when r>0. It is to be appreciated that the oxidized versions of the polycarbosilanes (r>0) operate very effectively in, and are well within the purview of the present invention. As is equally apparent, r can be zero independently of p, q, and s the only conditions being that the radicals p, q, r, and s of the Formula XXV polycarbosilanes must satisfy the conditions of [4<p+q+r+s<100,000], and q and r can collectively or independently be zero.

The polycarbosilane may be produced from starting materials that are presently commercially available from many manufacturers and by using conventional polymerization processes. As an example of synthesis of the polycarbosilanes, the starting materials may be produced from common organo silane compounds or from polysilane as a starting material by heating an admixture of polysilane with polyborosiloxane in an inert atmosphere to thereby produce the corresponding polymer or by heating an admixture of polysilane with a low molecular weight carbosilane in an inert atmosphere to thereby produce the corresponding polymer or by heating an admixture of polysilane with a low molecular carbosilane in an inert atmosphere and in the presence of a catalyst such as polyborodiphenylsiloxane to thereby produce the corresponding polymer. Polycarbosilanes may also be synthesized by Grignard Reaction reported in U.S. Pat. No. 5,153,295 hereby incorporated by reference.

An example of a preferred adhesion promoter having hydroxyl groups is phenol-formaldehyde resins or oligomers of the Formula XXVI:—[$R_{18}C_6H_2(OH)(R_{19})$]$_u$— where $R_{18}$ is substituted or unsubstituted alkylene, cycloalkylene, vinyl, allyl, or aryl; $R_{19}$ is alkyl, alkylene, vinylene, cycloalkylene, allylene, or aryl; and u=3–100. Examples of useful alkyl groups include —$CH_2$— and —$(CH_2)_v$— where v>1. A particularly useful phenol-formaldehyde resin oligomer has a molecular weight of 1500 and is commercially available from Schenectady International Inc.

The present adhesion promoter is preferably added in small, effective amounts from about 0.5% to up to 20% based on the weight of the present thermosetting composition and amounts up to about 5.0% by weight of the composition are generally more preferred.

By combining the adhesion promoter with the thermosetting component and subjecting the composition to thermal or a high energy source, the resulting compositions have superior adhesion characteristics throughout the entire polymer so as to ensure affinity to any contacted surface of the coating. The present adhesion promoters also improve striation control, viscosity, and film uniformity. Visual inspection confirms the presence of improved striation control.

The present compositions may also comprise additional components such as additional adhesion promoters, anti-foam agents, detergents, flame retardants, pigments, plasticizers, stabilizers, and surfactants.

Porogen:

The term "pore" as used herein includes void and cells in a material and any other term meaning space occupied by gas in the material. Appropriate gases include relatively pure gases and mixtures thereof. Air, which is predominantly a mixture of $N_2$ and $O_2$, is commonly distributed in the pores but pure gases such as nitrogen, helium, argon, $CO_2$, or CO are also contemplated. Pores are typically spherical but may alternatively or additionally include tubular, lamellar, discoidal, voids having other shapes, or a combination of the preceding shapes and may be open or closed. The term "porogen" as used herein means a decomposable material that is radiation, thermally, chemically, or moisture decomposable, degradable, depolymerizable, or otherwise capable of breaking down and includes solid, liquid, or gaseous material. The decomposed porogen is removable from or can volatilize or diffuse through a partially or fully cross-linked matrix to create pores in a subsequently fully cured matrix and thus, lower the matrix's dielectric constant and includes sacrificial polymers. Supercritical materials such as $CO_2$ may be used to remove porogen and decomposed porogen fragments. Preferably, for a thermally decomposable porogen, the porogen comprises a material having a decomposition temperature less than the glass transition temperature ($T_g$) of a material combined with it and greater than the curing temperature of the material combined with it. Preferably, the present porogens have a degradation or decomposition temperature of about 350° C. or greater. Preferably, the degraded or decomposed porogens volatilize at a temperature greater than the cure temperature of the material with which the porogen is combined and less than the Tg of the material. Preferably, the degraded or decomposed porogens volatilize at a temperature of about 96° C. or greater.

The phrase "porogen bonds to the thermosetting component" covers addition reactions, nucleophilic and electrophilic substitutions or eliminations, radical reactions, etc. Further alternative reactions may also include the formation of non-covalent bonds, such as Van der Waals, electrostatic bonds, ionic bonds, and hydrogen bonds.

Although International Patent Publication WO 00/31183 teaches that a porogen may be added to thermosettable benzocyclobutene, polyarylene, or thermosettable perfluoroethylene monomer to increase porosity thereof and thus, lower the dielectric constant of that resin, the reference teaches that a porogen that is known to function well with a first matrix system will not necessarily function well with another matrix system.

The present porogens preferably comprise unsubstituted polynorbornene, substituted polynorbornene, polycaprolactone, unsubstituted polystyrene, substituted polystyrene, polyacenaphthylene homopolymer, and polyacenaphthylene copolymer. The more preferred porogen is substituted polynorbornene. Preferably, the porogen has functional groups selected from the group consisting of epoxy, hydroxy, carboxylic acid groups, amino, and ethynyl. Preferably, the porogen has a functional group on at least one of its ends.

Figure 4:
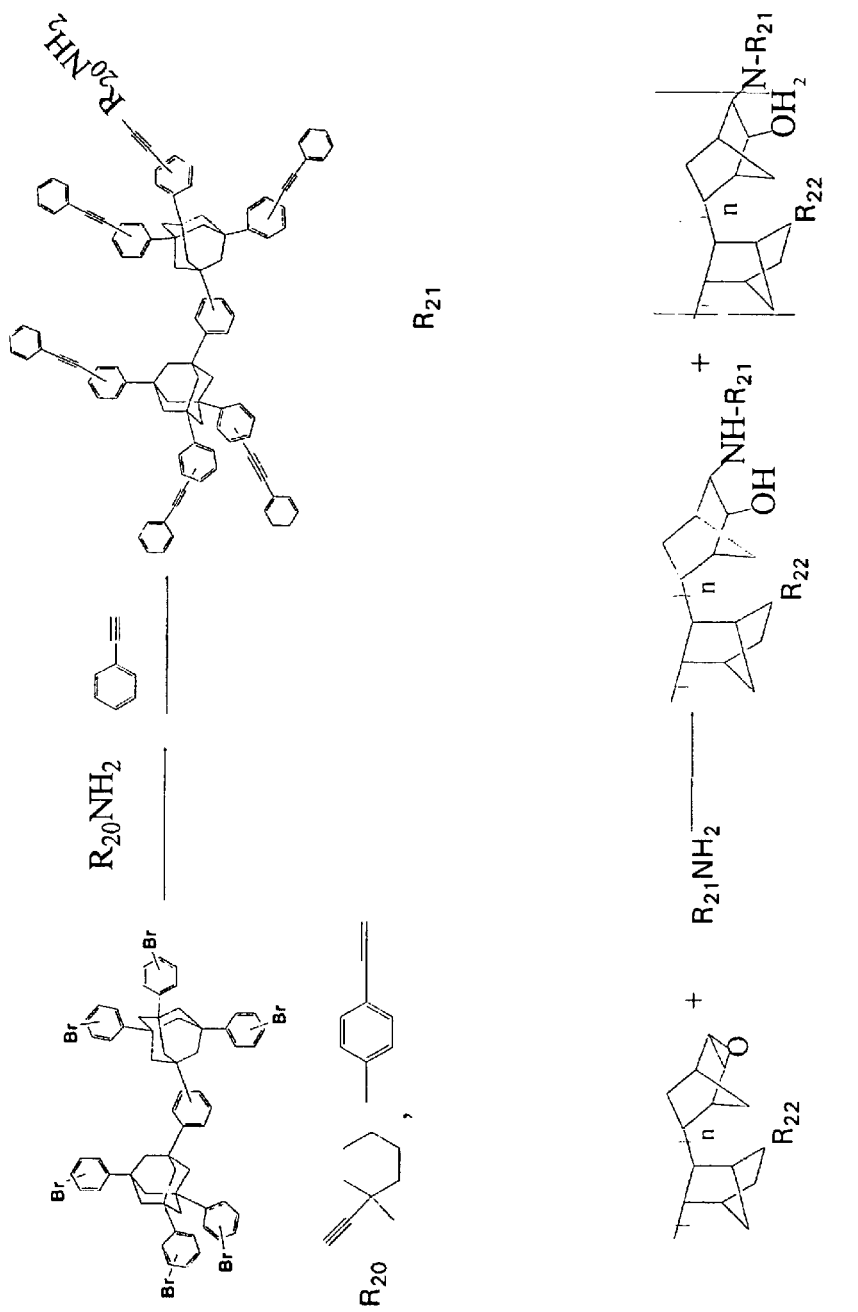
FIGS. 4 through 11 illustrate reaction schemes for covalently bonding the thermosetting component to the porogen in the present compositions.
Figure 5:
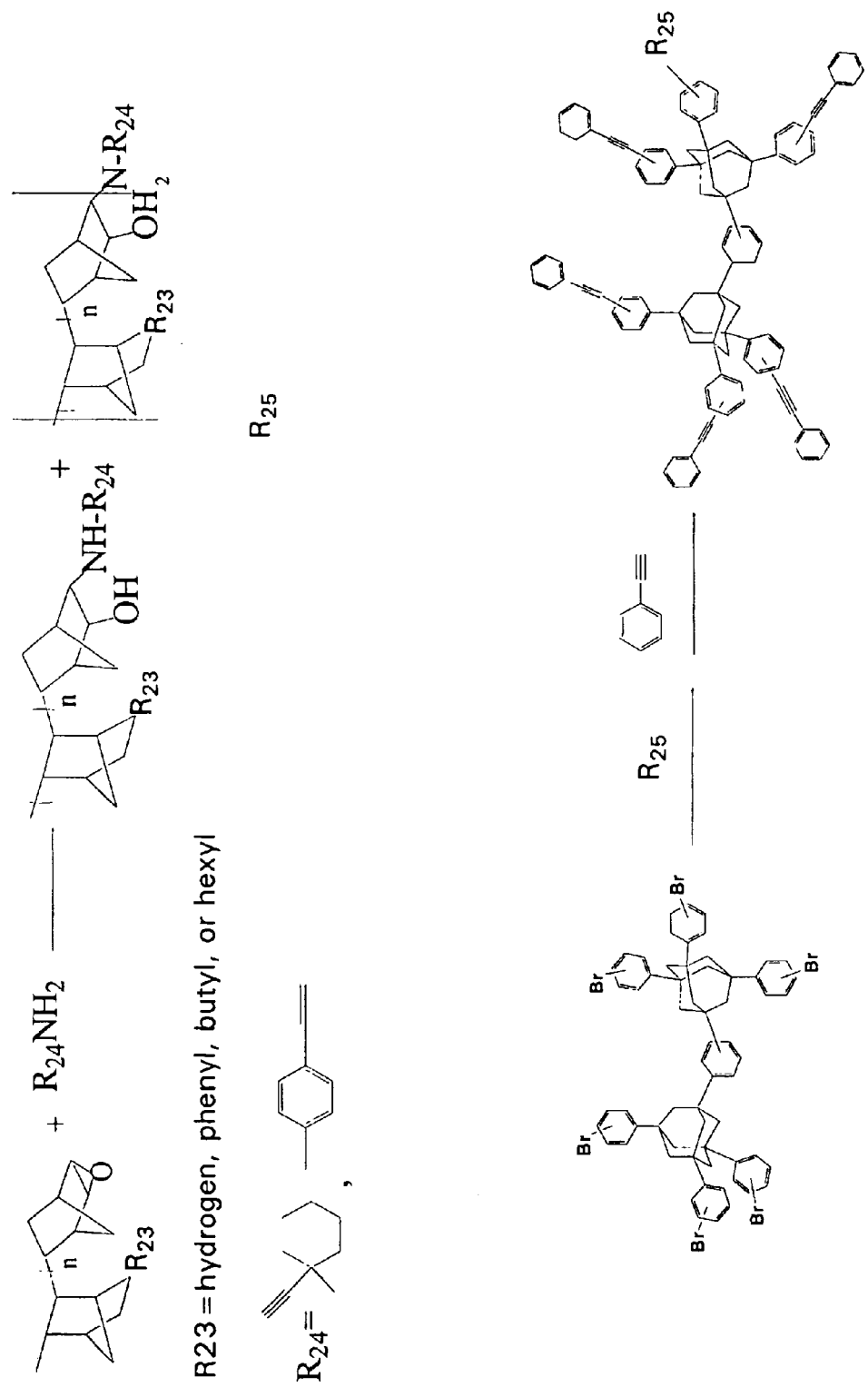
Figure 6:
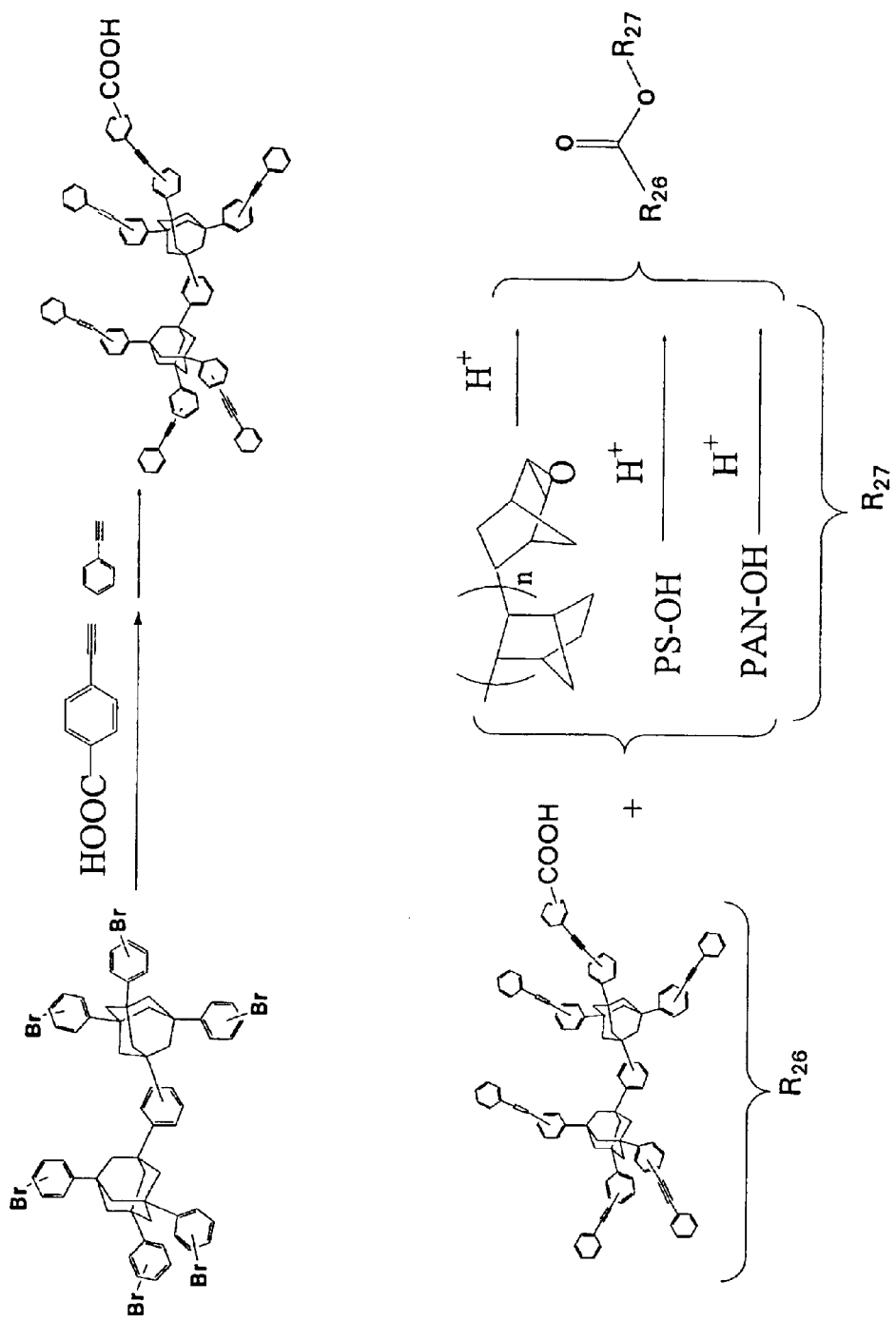
Figure 7:
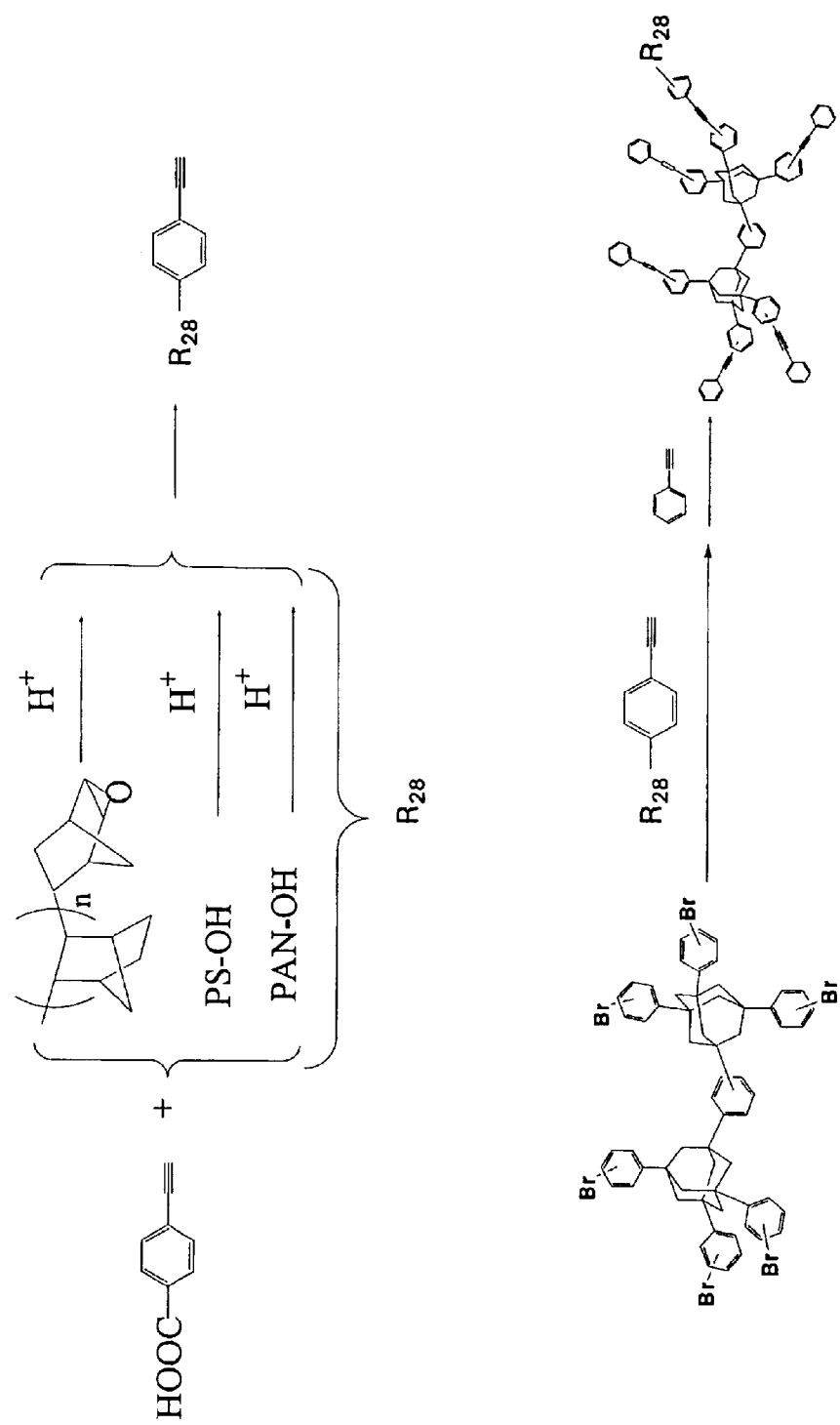
Figure 8:
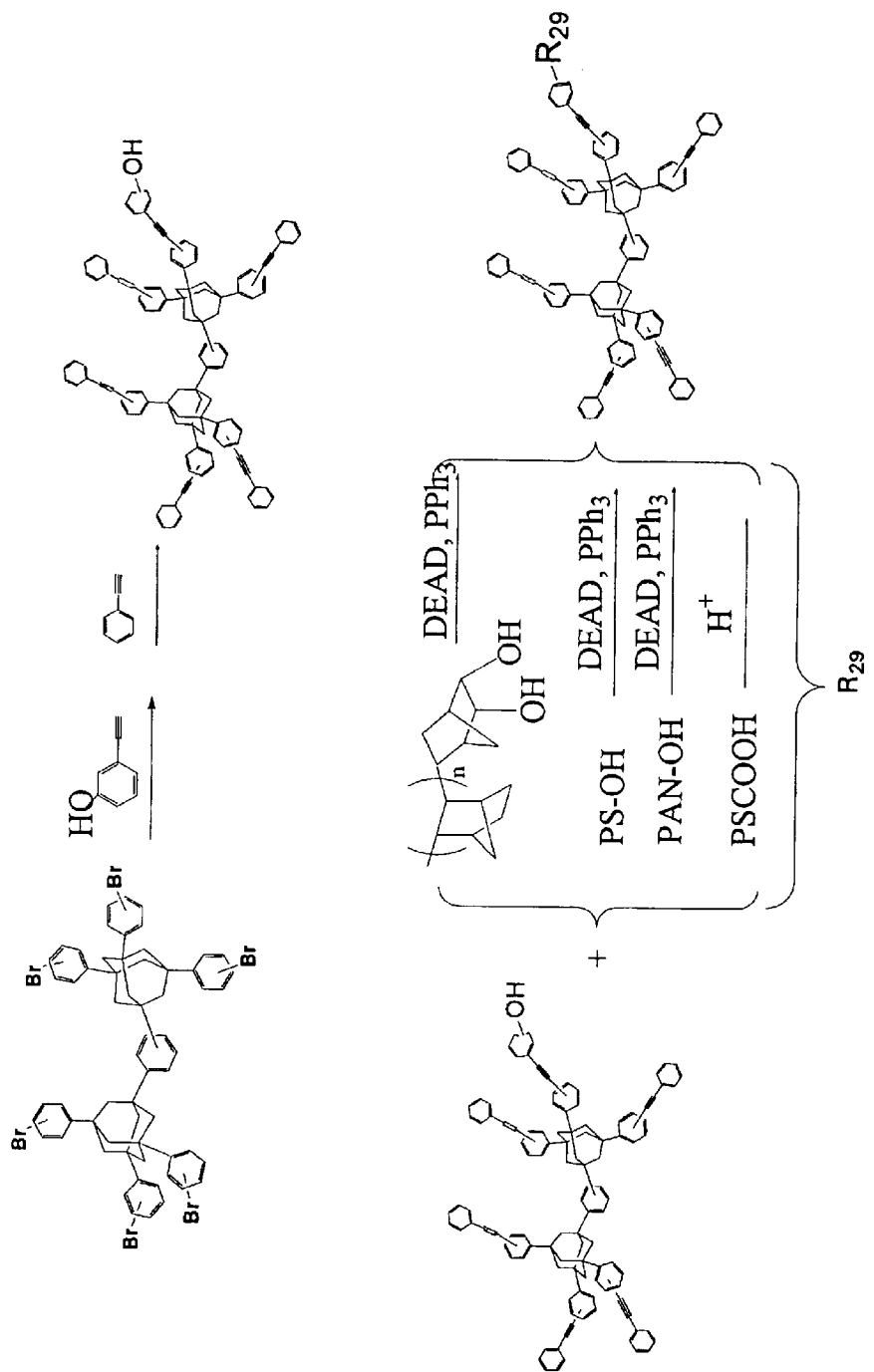
Figure 9:
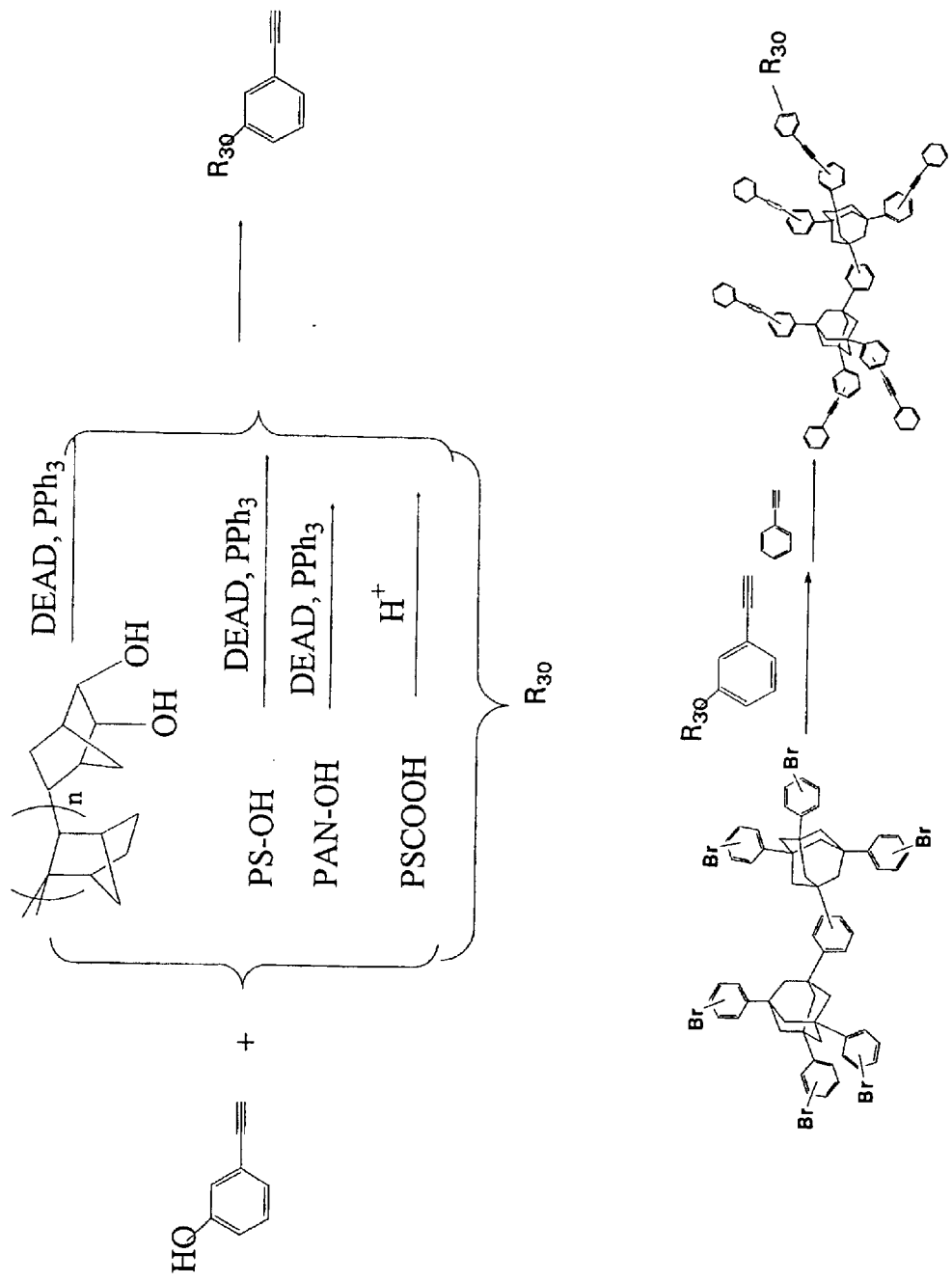
Figure 10:
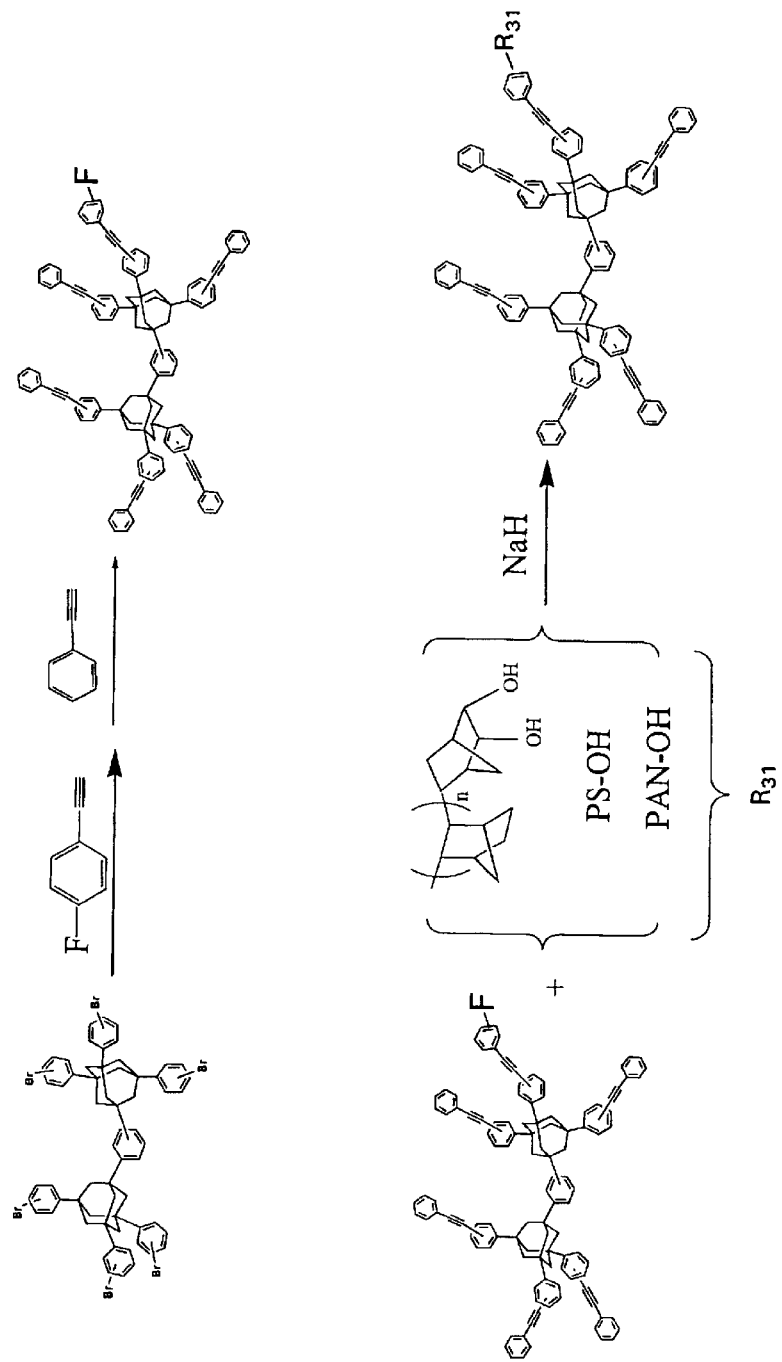
Figure 11:
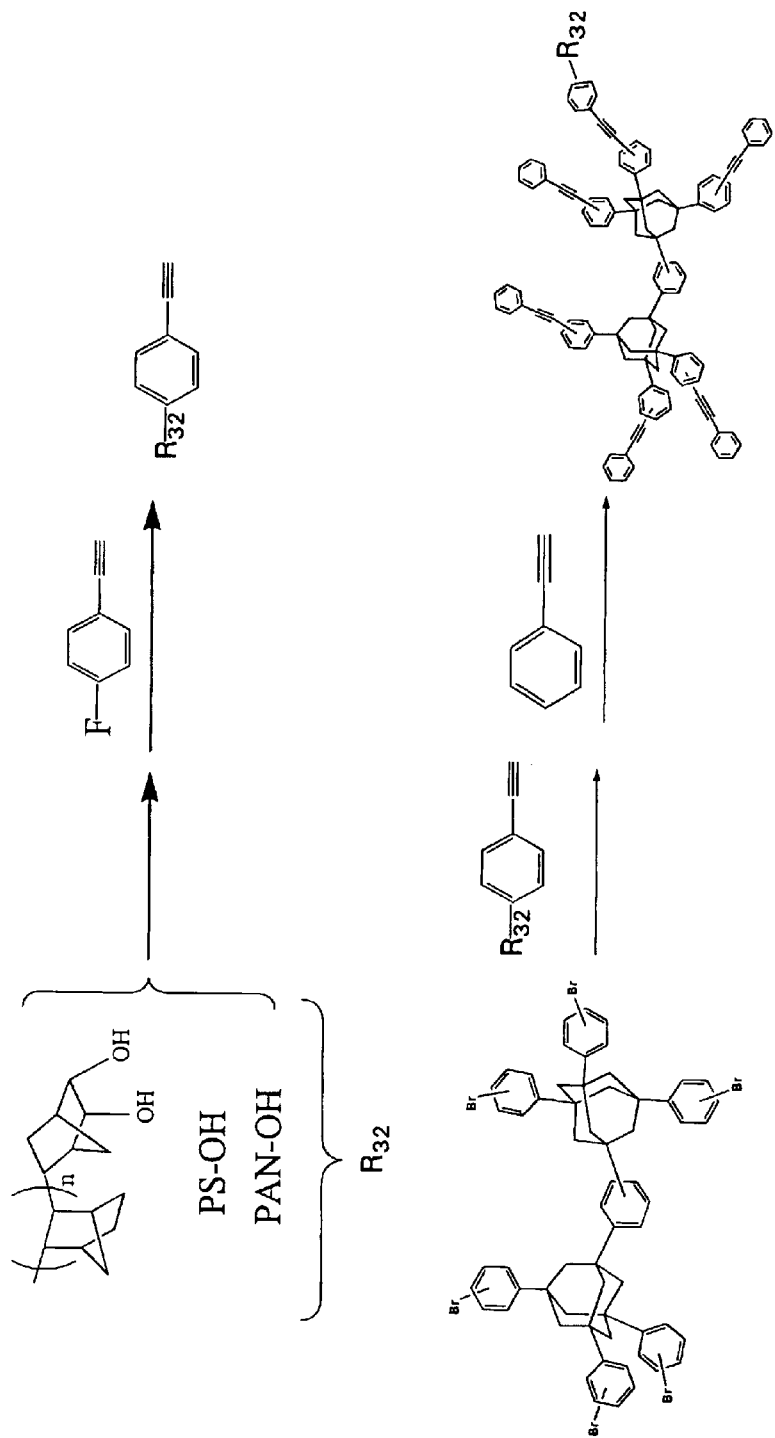

Preferably, the porogen is bonded to the thermosetting component through an ethynyl containing group. In one embodiment, the ethynyl containing group is first reacted with the porogen as shown in FIGS. 5, 7, 9, and 11. In a preferred embodiment, the ethynyl containing group is first reacted with the thermosetting component as shown in FIGS. 4, 6, 8, and 10. In FIGS. 4 though 11, although only 1,3/4-bis[1',3',5'-tris(3"/4"-bromophenyl)adamant-7'-yl] benzene is shown, it is understood that similar reaction occur for other useful thermosetting components including 1,3,5,7-tetrakis(3'/4'-bromophenyl)adamantane and 1,3-bis{3'/4'-[1",3',5"-tris(3'"/4'"-bromophenyl)adamant-7"-yl]phenyl}-5,7-bis{3""/4""-bromophenyl)adamantane. Useful ethynyl containing groups include fluorine; amine; or hydroxy; and preferably, are acetylene; 4-ethynylaniline; 3-hydroxyphenylacetylene; 4-fluorophenylacetylene; and 1-ethylcyclohexylamine. Preferably, a covalent bond forms between the porogen and the thermosetting component through the ethynyl containing group.

Useful polyacenaphthylene homopolymers may have weight average molecular weights ranging from preferably about 300 to about 20,000; more preferably about 300 to about 10,000; and most preferably about 300 to about 7,000.

The amount of thermosetting component used is about 50 to about 90 weight percent while the amount of porogen used is about 10 to about 50 weight percent. Preferably, an adhesion promoter as described above is added to the porogen bonded to the thermosetting component. Based on a composition comprising the adhesion promoter and the porogen bonded to the thermosetting component, about 0.1 to about 15 weight percent of adhesion promoter is used and about 5 to about 50 weight percent porogen bonded to the thermosetting component is used.

Pore Generation:

The term "degrade" as used herein refers to the breaking of covalent bonds. Such breaking of bonds may occur in numerous ways including heterolytic and homolytic breakage. The breaking of bonds need not be complete, i.e., not all breakable bonds must be cleaved. Furthermore, the breaking of bonds may occur in some bonds faster than in others. Ester bonds, for example, are generally less stable than amide bonds, and therefore, are cleaved at a faster rate. Breakage of bonds may also result in the release of fragments differing from one another, depending on the chemical composition of the degraded portion.

In the pore generation process, for thermally degradable porogens, thermal energy is applied to the porogen bonded to the thermosetting component to substantially degrade or decompose the porogen into its starting components or monomers. As used herein, "substantially degrade" preferably means at least 80 weight percent of the porogen degrades or decomposes. For the preferred thermosetting components of Formulae I and II above, the Tg is from about 400° C. to about 450° C. so the present porogens which have a degradation or decomposition temperature of about 350° C. or greater are particularly useful with this thermosetting component.

Thermal energy is also applied to volatilize the substantially degraded or decomposed porogen out of the thermosetting component matrix. Preferably, the same thermal energy is used for both the degradation and volatilization steps. As the amount of volatilized degraded porogen increases, the resulting porosity of the thermosetting component increases. For the preferred thermosetting components of Formulae I and II above, the Tg is from about 400° C. to about 450° C. so the present substantially degraded porogens which have a volatilization temperature of about 96° C. or greater are particularly useful with said thermosetting component.

Preferably, the cure temperature used for cross-linking the thermosetting component will also substantially degrade the porogen and volatilize it out of the thermosetting matrix. Typical cure temperature and conditions will be described in the Utility section below.

The resulting pores may be uniformly or randomly dispersed throughout the matrix. Preferably, the pores are uniformly dispersed throughout the matrix.

Alternatively, other procedures or conditions which at least partially remove the porogen without adversely affecting the thermosetting component may be used. Preferably, the porogen is substantially removed. Typical removal methods include, but are not limited to, exposure to radiation, such as but not limited to, electromagnetic radiation such as ultraviolet, x-ray, laser, or infrared radiation; mechanical energy such as sonication or physical pressure; or particle radiation such as gamma ray, alpha particles, neutron beam, or electron beam.

Utility:

The term "layer" as used herein includes film and coating.

The term "low dielectric constant polymer" as used herein refers to an organic, organometallic, or inorganic polymer with a dielectric constant of approximately 3.0, or lower. The low dielectric material is typically manufactured in the form of a thin layer having a thickness from 100 to 25,000 Angstroms but also may be used as thick films, blocks, cylinders, spheres etc.

The present composition of thermosetting component, adhesion promoter, and porogen is useful in lowering the dielectric constant of a material. Preferably, the dielectric material has a dielectric constant k of less than or equal to about 3.0 and more preferably, from about 1.9 to 3.0. The dielectric material has a glass transition temperature of preferably at least about 350° C.

Layers of the instant compositions of thermosetting component, adhesion promoter, and porogen may be formed by solution techniques such as spraying, rolling, dipping, spin coating, flow coating, or casting, with spin coating being preferred for microelectronics. Preferably, the present composition is dissolved in a solvent. Suitable solvents for use in such solutions of the present compositions include any suitable pure or mixture of organic, organometallic, or inorganic molecules that are volatized at a desired temperature. Suitable solvents include aprotic solvents, for example, cyclic ketones such as cyclopentanone, cyclohexanone, cycloheptanone, and cyclooctanone; cyclic amides such as N-alkylpyrrolidinone wherein the alkyl has from about 1 to 4 carbon atoms; and N-cyclohexylpyrrolidinone and mixtures thereof. A wide variety of other organic solvents may be used herein insofar as they are able to aid dissolution of the adhesion promoter and at the same time effectively control the viscosity of the resulting solution as a coating solution. Various facilitating measures such as stirring and/or heating may be used to aid in the dissolution. Other suitable solvents include methyethylketone, methylisobutylketone, dibutyl ether, cyclic dimethylpolysiloxanes, butyrolactone, γ-butyrolactone, 2-heptanone, ethyl 3-ethoxypropionate, polyethylene glycol [di]methyl ether, propylene glycol methyl ether acetate (PGMEA), and anisole, and hydrocarbon solvents such as mesitylene, xylenes, benzene, and toluene. Preferred solvent is cyclohexanone. Typically, layer thicknesses are between 0.1 to about 15 microns. As a dielectric interlayer for microelectronics, the layer thickness is generally less than 2 microns.

The present composition may be used in electrical devices and more specifically, as an interlayer dielectric in an interconnect associated with a single integrated circuit ("IC") chip. An integrated circuit chip typically has on its surface a plurality of layers of the present composition and multiple layers of metal conductors. It may also include regions of the present composition between discrete metal conductors or regions of conductor in the same layer or level of an integrated circuit.

In application of the instant polymers to ICs, a solution of the present composition is applied to a semiconductor wafer using conventional wet coating processes such as, for example, spin coating; other well known coating techniques such as spray coating, flow coating, or dip coating may be employed in specific cases. As an illustration, a cyclohexanone solution of the present composition is spin-coated onto a substrate having electrically conductive components fabricated therein and the coated substrate is then subjected to thermal processing. An exemplary formulation of the instant composition is prepared by dissolving the present composition in cyclohexanone solvent under ambient conditions with strict adherence to a clean-handling protocol to prevent trace metal contamination in any conventional apparatus having a non-metallic lining. The resulting solution comprises based on the total solution weight, from preferably about 2 to about 30 weight percent of thermosetting component, adhesion promoter, and porogen, and about 70 to about 98 weight percent solvent and more preferably about 5 to about 25 weight percent of thermosetting component, adhesion promoter, and porogen, and about 75 to about 95 weight percent solvent.

An illustration of the use of the present invention follows. Application of the instant compositions to form a layer onto planar or topographical surfaces or substrates may be carried out by using any conventional apparatus, preferably a spin coater, because the compositions used herein have a controlled viscosity suitable for such a coater. Evaporation of the solvent by any suitable means, such as simple air drying during spin coating, by exposure to an ambient environment, or by heating on a hot plate up to 350° C., may be employed. The substrate may have on it at least one layer of the present preferred composition of thermosetting component, adhesion promoter, and porogen.

Substrates contemplated herein may comprise any desirable substantially solid material. Particularly desirable substrate layers comprise films, glass, ceramic, plastic, metal or coated metal, or composite material. In preferred embodiments, the substrate comprises a silicon or gallium arsenide die or wafer surface, a packaging surface such as found in a copper, silver, nickel or gold plated leadframe, a copper surface such as found in a circuit board or package interconnect trace, a via-wall or stiffener interface ("copper" includes considerations of bare copper and its oxides), a polymer-based packaging or board interface such as found in a polyimide-based flex package, lead or other metal alloy solder ball surface, glass and polymers. Useful substrates include silicon, silicon nitride, silicon oxide, silicon oxycarbide, silicon dioxide, silicon carbide, silicon oxynitride, titanium nitride, tantalum nitride, tungsten nitride, aluminum, copper, tantalum, organosiloxanes, organo silicon glass, and fluorinated silicon glass. In other embodiments, the substrate comprises a material common in the packaging and circuit board industries such as silicon, copper, glass, and polymers. The present compositions may also be used as a dielectric substrate material in microchips, multichip modules, laminated circuit boards, or printed wiring boards. The circuit board made up of the present composition will have mounted on its surface patterns for various electrical conductor circuits. The circuit board may include various reinforcements, such as woven non-conducting fibers or glass cloth. Such circuit boards may be single sided, as well as double sided.

Layers made from the present compositions possess a low dielectric constant, high thermal stability, high mechanical strength, and excellent adhesion to electronic substrate surfaces. Because the adhesion promoter is molecularly dispersed, these layers demonstrate excellent adhesion to all affixed surfaces including underlying substrates and overlaid capping or masking layers, such as $SiO_2$ and $Si_3N_4$ capping layers. The use of these layers eliminates the need for an additional process step in the form of at least one primer coating application to achieve adhesion of the film to a substrate and/or overlaid surface.

After application of the present composition to an electronic topographical substrate, the coated structure is subjected to a bake and cure thermal process at increasing temperatures ranging from about 50° C. up to about 450° C. to polymerize the coating. The curing temperature is at least about 300° C. because a lower temperature is insufficient to complete the reaction herein. Generally, it is preferred that curing is carried out at temperatures of from about 375° C. to about 425° C. Curing may be carried out in a conventional curing chamber such as an electric furnace, hot plate, and the like and is generally performed in an inert (non-oxidizing) atmosphere (nitrogen) in the curing chamber. In addition to furnace or hot plate curing, the present compositions may also be cured by exposure to ultraviolet radiation, microwave radiation, or electron beam radiation as taught by commonly assigned patent publication PCT/US96/08678 and U.S. Pat. Nos. 6,042,994; 6,080,526; 6,177,143; and 6,235,353, which are incorporated herein by reference in their entireties. Any non oxidizing or reducing atmospheres (e.g., argon, helium, hydrogen, and nitrogen processing gases) may be used in the practice of the present invention, if they are effective to conduct curing of the present adhesion promoter-modified thermosetting component to achieve the low k dielectric layer herein.

While not to be construed as limiting, it is observed that the processing used to prepare the present low dielectric constant composition results in a homogeneous solution of thermosetting component, adhesion promoter, and porogen. The preferred silane adhesion promoter advantageously serves multiple functions in the low dielectric constant composition. For example, the processing of the present composition enables the preferred polycarbosilane adhesion promoter to interact with both the porogen and the unsaturated structures of thermosetting component. It is believed that the silane portions of the preferred polycarbosilane interact with the porogen and thermosetting component. It is speculated that the polycarbosilane acts as a surfactant or emulsification agent to uniformly disperse the porogen within the thermosetting component in the low dielectric composition. This is critical to producing a composition that gives a homogeneous film (or layer) with uniformly dispersed pores of very small dimension. The silane portion of the polycarbosilane also reacts with the substrate surfaces, thereby creating a chemically bonded adherent interface for the dominant thermosetting monomer precursor. It has been proposed that silylene/silyl radicals being available throughout the composition act as attachment sources to fasten and secure any interface surface of contact by chemical bonding therewith. The interactions between the various components and the reactions of the silane portion may occur during formulation and treatment prior to layer formation. As indicated, the dispersion of silane functionality with the porogen and thermosetting component throughout the composition accounts for the uniform porosity in the resulting layers. The dispersion of the silane functionality also leads to reactive radicals as well as the superb adhesion of the instant layers to both underlying substrate surfaces as well as overlayered surface structures such as cap or masking layers. Crucial to the materials discovered herein are the findings that the preferred Formula XXV polycarbosilane adhesion promoters have a hydrido substituted silicon in the backbone structure of the polycarbosilane. This feature of the polycarbosilane enables it to: (1) mix uniformly with the porogen to form a homogeneous composition, (2) be reactive with thermosetting component; (3) uniformly blend and disperse the porogen within the thermosetting component providing a uniform composition leading to uniform distribution of small pores in the final porous layer, and (4) generate a polycarbosilane-modified thermosetting composition and porous layer that possesses improved adhesion performance.

As indicated earlier, the present adhesion promoter-modified thermosetting component (a) coating may act as an interlayer and be covered by other coatings, such as other dielectric ($SiO_2$) coatings, $SiO_2$ modified ceramic oxide layers, silicon containing coatings, silicon carbon containing coatings, silicon nitrogen containing coatings, silicon-nitrogen-carbon containing coatings, diamond like carbon coatings, titanium nitride coatings, tantalum nitride coatings, tungsten nitride coatings, aluminum coatings, copper coatings, tantalum coatings, organosiloxane coatings, organo silicon glass coatings, and fluorinated silicon glass coatings. Such multilayer coatings are taught in U.S. Pat. No. 4,973,526, which is incorporated herein by reference. And, as amply demonstrated, the present polycarbosilane-modified thermosetting component (a) prepared in the instant process may be readily formed as interlined dielectric layers between adjacent conductor paths on fabricated electronic or semiconductor substrates.

The present films may be used in dual damascene (such as copper) processing and substractive metal (such as aluminum or aluminum/tungsten) processing for integrated circuit manufacturing. The present compositions may be used as an etch stop, hardmask, air bridge, or passive coating for enveloping a completed wafer. The present composition may be used in a desirable all spin-on stacked film as taught by Michael E. Thomas, "Spin-On Stacked Films for Low $k_{eff}$ Dielectrics", *Solid State Technology* (July 2001), incorporated herein in its entirety by reference. The present layers may be used in stacks with other layers comprising organosiloxanes such as taught by commonly assigned U.S. Pat. No. 6,143,855 and pending U.S. Ser. No. 10/078919 filed Feb. 19, 2002; Honeywell International Inc.'s commercially available HOSP ® product; nanoporous silica such as taught by commonly assigned U.S. Pat. No. 6,372,666; Honeywell International Inc.'s commercially available NANOGLASS ® E product; organosilsesquioxanes taught by commonly assigned WO 01/29052; and fluorosilsesquioxanes taught by commonly assigned WO 01/29141, incorporated herein in their entirety.

Analytical Test Methods:

Proton NMR: A 2–5 mg sample of the material to be analyzed was put into an NMR tube. About 0.7 ml deuterated chloroform was added. The mixture was shaken by hand to dissolve the material. The sample was then analyzed using a Varian 400 MHz NMR.

High Performance Liquid Chromatography (HPLC): A HPLC with a Phenomenex luna Phenyl-Hexyl 250×4.6 mm 5 micron column was used. The column temperature was set at 40° C. Water and acetonitrile were used to improve peak separation.

| TIME | WATER | ACETONITRILE |
| --- | --- | --- |
| Initial | 20% | 80% |
| 10 minutes | 0% | 100% |
| 30 minutes | 0% | 100% |

The following experimental conditions were used:

| | |
| --- | --- |
| INJECTION VOLUME | 10 microliters |
| DETECTION | UV at 200 nm |
| STOP TIME | 30 minutes |
| POST TIME | 5 minutes |

The samples were prepared as follows.

For a mixture of the halogenated intermediate such as the mixture of 1,3,5,7-tetrakis(3'/4'-bromophenyl)adamantane and 1,3/4-bis[1',3',5'-tris(3"/4"-bromophenyl]adamant-7'-yl] benzene of Preparation 1 below, the reaction mixture (0.5–1 milliliter) was shaken with approximately 4% HCl (several milliliters). The organic layer was shaken with water. An organic layer sample (twenty microliters) was taken and added to acetonitrile (one milliliter).

For a mixture of the final product such as the mixture of 1,3,5,7-tetrakis[3'/4'-(phenylethynyl)phenyl]adamantane and 1,3/4-bis{1',3',5'-tris[3"/4"-(phenylethynyl)phenyl] adamant-7'-yl}benzene of Preparation 1 below, the reaction mixture (0.5 gram) was mixed with chloroform (five milliliters) and 3–5% HCl (5 milliliters) and shaken. The organic layer was washed by water. An organic layer sample (100 microliters) was added to tetrahydrofuran (0.9 milliliter).

Gel Permeation Chromatography (GPC 1): The GPC analysis was done with Waters liquid chromatography system composed from Water 717 plus Autosampler, Waters in-line degasser, Waters 515 HPLC pump, Waters 410 Differential Refractometer (RI detector), and two columns: HP PI gel 5µ MIXED D. The analysis conditions were:

| | |
| --- | --- |
| Mobile Phase | Tetrahydrofuran (THF) |
| Column flow (milliliters/min) | 1.0 |
| Column temperature (° C.) | 40.0 |
| Detection | Refractive Index, Polarity positive |
| Analysis run time | 25 min |
| Injection quantity (µL) | 50 |

The solid product sample (10 milligrams) was prepared by dissolving in tetrahydrofuran (one milliliter).

Gel Permeation Chromatography (GPC 2): This method may be used to provide additional detail about the dimer and trimer peaks. The following conditions are used:

| | |
| --- | --- |
| Analysis Apparatus | Shimadzu LC10 |
| Separation Column | Plgel 5 µ pre-column |
| | Plgel 5 µ 1000 Å, 300 × 7.5 nm |
| | Plgel 5 µ 500 Å, 300 × 7.5 nm |
| | Plgel 5 µ 100 Å, 300 × 7.5 nm |
| Mobile Phase | Eluent A: toluene |
| Column Flow (milliliters/minute) | 1.0 |
| Column Temperature (° C.) | 40 |
| Detection | Refractive Index, Polarity Positive |
| Analysis Run Time (minutes) | 32 |
| Trial Solution | 10 milligrams/milliliter toluene |
| Injection Quantity (µ) | 50 |

To calculate the contents, in other words area-%, the peak area belonging to the monomer or the peak area belonging to the oligomer or polymer is related to the total of all the peak areas in the chromatogram.

Gel Permeation Chromatography (GPC 3): Separation was performed with a Waters 2690 separation module with Waters 996 diode array and Waters 410 differential refractometer detectors. The separation was performed on two PLgel 3 μm Mixed-E 300×7.5 mm columns with chloroform flowing at 1 ml/min. Injection volumes of 25 μl of solutions of about 1 mg/ml concentration were run in duplicate. Good reproducibility was observed.

The column was calibrated with relatively monodisperse polystyrene standards between 20,000 and 500 molecular weight. With the lower molecular weight standards nine distinct components could be resolved corresponding to butyl terminated styrene monomer through oligomers with nine styrenes. The logs of the peak molecular weight of the standards were fit with a third order polynomial of the elution time. The instrumental broadening was evaluated from the ratio of the full width at half maximum to the mean elution time of toluene.

The absorbance for Preparations 1 and 2 below was a maximum at about 284 nm. The chromatograms had similar shapes at absorbance at wavelengths below about 300 nm. The results presented here correspond to 254 nm absorbance. The peaks were identified by the molecular weight of the polystyrene that would be eluting at the same time. These values should not be considered as measurements of molecular weight of the Preparation 1 and 2 oligomers. The sequential elution of higher oligomers, trimers, dimers, oligomers, and incomplete oligomers at increasing times can be quantitated.

Each component was broader than that which would be observed for a monodisperse species. This width was analyzed from the full width in minutes at half maximum of the peak. To roughly account for the instrumental broadening, we calculated $$\text{width}_{corrected} = [\text{width}_{observed}^2 - \text{width}_{instrument}^2]^{1/2}$$

where $\text{width}_{instrument}$ is the observed width of toluene corrected by the ratio of the elution times of the peak to that for toluene. The peak width was converted to a molecular weight width through the calibration curve and ratioed to the peak molecular width. Since the molecular weight of styrene oligomers was proportional to the square of their size, the relative molecular weight width can be converted to a relative oligomer size width by dividing by 2. This procedure accounted for the difference in molecular configuration of the two species.

Liquid Chromatography-Mass Spectroscopy (LC-MS): This analysis was performed on a Finnigan/MAT TSQ7000 triple stage quadrupole mass spectrometer system, with an Atmospheric Pressure Ionization (API) interface unit, using a Hewlett-Packard Series 1050 HPLC system as the chromatographic inlet. Both mass spectral ion current and variable single wavelength UV data were acquired for time-intensity chromatograms.

Chromatography was conducted on a Phenomenex Luna 5-micron pheny-hexyl column (250×4.6 mm). Sample auto-injections were generally between 5 and 20 microliters of concentrated solutions, both in tetrahydrofuran and without tetrahydrofuran. The preferred preparation of concentrated sample solutions for analysis was dissolution in tetrahydrofuran, of about 5 milligrams solid product per milliliter, for 10 microliter injections. The mobile phase flow through the column was 1.0 milliliter/minute of acetonitrile/water, initially 70/30 for 1 minute then gradient programmed to 100% acetonitrile at 10 minutes and held until 40 minutes.

Atmospheric Pressure Chemical Ionization (APCI) mass spectra were recorded in both positive and negative ionization, in separate experiments. Positive APCI was more informative of molecular structure for these final products, providing protonated pseudomolecular ions including adducts with acetonitrile matrix. The APCI corona discharge was 5 microamps, about 5 kV for positive ionization, and about 4 kV for negative ionization. The heated capillary line was maintained at 200° C. and the vaporizer cell at 400° C. The ion detection system after quadrupole mass analysis was set at 15 kV conversion dynode and 1500V electron multiplier voltage. Mass spectra were typically recorded at 1.0 second/scan from about m/z 50 to 2000 a.m.u. for negative ionization, and from about m/z 150 a.m.u. up for positive ionization. In separate positive ion experiments, the mass range was scanned up both to 2000 a.m.u. in low mass tune/calibration mode and to 4000 a.m.u. in high mass tune/calibration mode.

Differential Scanning Calorimetry (DSC): DSC measurements were performed using a TA Instruments 2920 Differential Scanning Calorimeter in conjunction with a controller and associated software. A standard DSC cell with temperature ranges from 250° C. to 725° C. (inert atmosphere: 50 ml/min of nitrogen) was used for the analysis. Liquid nitrogen was used as a cooling gas source. A small amount of sample (10–12 mg) was carefully weighed into an Auto DSC aluminum sample pan (Part # 990999-901) using a Mettler Toledo Analytical balance with an accuracy of ±0.0001 grams. Sample was encapsulated by covering the pan with the lid that was previously punctured in the center to allow for outgasing. Sample was heated under nitrogen from 0° C. to 450° C. at a rate of 100° C./minute (cycle 1), then cooled to 0° C. at a rate of 100° C./minute. A second cycle was run immediately from 0° C. to 450° C. at a rate of 100° C./minute (repeat of cycle 1). The cross-linking temperature was determined from the first cycle.

FTIR analysis: FTIR spectra were taken using a Nicolet Magna 550 FTIR spectrometer in transmission mode. Substrate background spectra were taken on uncoated substrates. Film spectra were taken using the substrate as background. Film spectra were then analyzed for change in peak location and intensity.

Dielectric Constant: The dielectric constant was determined by coating a thin film of aluminum on the cured layer and then doing a capacitance-voltage measurement at 1 MHz and calculating the k value based on the layer thickness.

Glass Transition Temperature (Tg): The glass transition temperature of a thin film was determined by measuring the thin film stress as a function of temperature. The thin film stress measurement was performed on a KLA 3220 Flexus. Before the film measurement, the uncoated wafer was annealed at 500° C. for 60 minutes to avoid any errors due to stress relaxation in the wafer itself. The wafer was then deposited with the material to be tested and processed through all required process steps. The wafer was then placed in the stress gauge, which measured the wafer bow as function of temperature. The instrument calculated the stress versus temperature graph, provided that the wafer thickness and the film thickness were known. The result was displayed in graphic form. To determine the Tg value, a horizontal tangent line was drawn (a slope value of zero on the stress vs. temperature graph). Tg value was where the graph and the horizontal tangent line intersect.

It should be reported if the Tg was determined after the first temperature cycle or a subsequent cycle where the maximum temperature was used because the measurement process itself may influence Tg.

Isothermal Gravimetric Analysis (ITGA) Weight Loss: Total weight loss was determined on the TA Instruments 2950 Thermogravimetric Analyzer (TGA) used in conjunction with a TA Instruments thermal analysis controller and associated software. A platinel II Thermocouple and a Standard Furnace with a temperature range of 25° C. to 1000° C. and heating rate of 0.1° C. to 100° C./min were used. A small amount of sample (7 to 12 mg) was weighed on the TGA's balance (resolution: 0.1 g; accuracy: to ±0.1% and heated on a platinum pan. Samples were heated under nitrogen with a purge rate of 100 ml/min (60 ml/min going to the furnace and 40 ml/min to the balance). Sample was equilibrated under nitrogen at 20° C. for 20 minutes, then temperature was raised to 200° C. at a rate of 10° C./minute and held at 200° C. for 10 minutes. Temperature was then ramped to 425° C. at a rate of 10° C./minute and held at 425° C. for 4 hours. The weight loss at 425° C. for the 4 hour period was calculated.

Shrinkage: Film shrinkage was measured by determining the film thickness before and after the process. Shrinkage was expressed in percent of the original film thickness. Shrinkage was positive if the film thickness decreased. The actual thickness measurements were performed optically using a J. A. Woollam M-88 spectroscopic ellipsometer. A Cauchy model was used to calculate the best fit for Psi and Delta (details on Ellipsometry can be found in e.g. "Spectroscopic Ellipsometry and Reflectometry" by H. G. Thompkins and William A. McGahan, John Wiley and Sons, Inc., 1999).

Refractive Index: The refractive index measurements were performed together with the thickness measurements using a J. A. Woollam M-88 spectroscopic ellipsometer. A Cauchy model was used to calculate the best fit for Psi and Delta. Unless noted otherwise, the refractive index was reported at a wavelenth of 633 nm (details on Ellipsometry can be found in e.g. "Spectroscopic Ellipsometry and Reflectometry" by H. G. Thompkins and William A. McGahan, John Wiley and Sons, Inc., 1999).

Modulus and Hardness: Modulus and hardness were measured using instrumented indentation testing. The measurements were performed using a MTS Nanoindenter XP (MTS Systems Corp., Oak Ridge, Tenn.). Specifically, the continuous stiffness measurement method was used, which enabled the accurate and continuous determination of modulus and hardness rather than measurement of a discrete value from the unloading curves. The system was calibrated using fused silica with a nominal modulus of 72+-3.5 GPa. The modulus for fused silica was obtained from average value between 500 to 1000 nm indentation depth. For the thin films, the modulus and hardness values were obtained from the minimum of the modulus versus depth curve, which is typically between 5 to 15% of the film thickness.

Tape Test: The tape test was performed following the guidelines given in ASTM D3359–95. A grid was scribed into the dielectric layer according to the following. A tape test was performed across the grid marking in the following manner: (1) a piece of adhesive tape, preferably Scotch brand #3 m600-½×1296, was placed on the present layer, and pressed down firmly to make good contact; and (2) the tape was then pulled off rapidly and evenly at an angle of 180° to the layer surface. The sample was considered to pass if the layer remained intact on the wafer, or to have failed if part or all of the film pulled up with the tape.

Stud pull Test: Epoxy-coated studs were attached to the surface of a wafer containing the layers of the present invention. A ceramic backing plate was applied to the back side of the wafer to prevent substrate bending and undue stress concentration at the edges of the stud. The studs were then pulled in a direction normal to the wafer surface by a testing apparatus employing standard pull protocol steps. The stress applied at the point of failure and the interface location were then recorded.

Compatibility with Solvents: Compatibility with solvents was determined by measuring film thickness, refractive index, FTIR spectra, and dielectric constant before and after solvent treatment. For a compatible solvent, no significant change should be observed.

Average Pore Size Diameter: The $N_2$ isotherms of porous samples was measured on a Micromeretics ASAP 2000 automatic isothermal $N_2$ sorption instrument using UHP (ultra high purity industrial gas) $N_2$, with the sample immersed in a sample tube in a liquid $N_2$ bath at 77° K.

For sample Preparation, the material was first deposited on silicon wafers using standard processing conditions. For each sample, three wafers were prepared with a film thickness of approximately 6000 Angstroms. The films were then removed from the wafers by scraping with a razor blade to generate powder samples. These powder samples were pre-dried at 180° C. in an oven before weighing them, carefully pouring the powder into a 10 mm inner diameter sample tube, then degassing at 180° C. at 0.01 Torr for>3 hours.

The adsorption and desorption $N_2$ sorption was then measured automatically using a 5 second equilibration interval, unless analysis showed that a longer time was required. The time required to measure the isotherm was proportional to the mass of the sample, the pore volume of the sample, the number of data points measured, the equilibration interval, and the P/Po tolerance. (P is actual pressure of the sample in the sample tube. Po is the ambient pressure outside the instrument.) The instrument measures the $N_2$ isotherm and plots $N_2$ versus P/Po.

The apparent BET (Brunauer, Emmett, Teller method for multi-layer gas absorption on a solid surface disclosed in S. Brunauer, P. H. Emmett, E. Teller; *J. Am. Chem. Soc.*, 60, 309–319 (1938)) surface area was calculated from the lower P/Po region of the N2 adsorption isotherm using the BET theory, using the linear section of the BET equation that gives an $R^2$ fit>0.9999.

The pore volume was calculated from the volume of $N_2$ adsorbed at the relative pressure P/Po value, usually $P/Po^{18}$ 0.95, which is in the flat region of the isotherm where condensation is complete, assuming that the density of the adsorbed $N_2$ is the same as liquid $N_2$ and that all the pores are filled with condensed $N_2$ at this P/Po.

The pore size distribution was calculated from the adsorption arm of the $N_2$ isotherm using the BJH (E. P. Barret, L. G. Joyner, P. P. Halenda; *J. Am. Chem. Soc.*, 73, 373–380 (1951)) pore size distribution from the N2 isotherm using the Kelvin equation) theory. This uses the Kelvin equation, which relates curvature to suppression of vapor pressure, and the Halsey equation, which describes the thickness of the adsorbed $N_2$ monolayer versus P/Po, to convert the volume of condensed $N_2$ versus P/Po to the pore volume in a particular range of pore sizes.

The average cylindrical pore diameter D was the diameter of a cylinder that has the same apparent BET surface area Sa ($m^2$/g) and pore volume Vp (cc/g) as the sample, so D (nm)=4000Vp/Sa.

Thermal Desorption Mass Spectroscopy: Thermal Desorption Mass Spectroscopy (TDMS) is used to measure the thermal stability of a material by analyzing the desorbing species while the material is subjected to a thermal treatment.

The TDMS measurement was performed in a high vacuum system equipped with a wafer heater and a mass spectrometer, which was located close to the front surface of the wafer. The wafer was heated using heating lamps, which heat the wafer from the backside. The wafer temperature was measured by a thermocouple, which was in contact with the front surface of the wafer. Heater lamps and thermocouple were connected to a programmable temperature controller, which allowed several temperature ramp and soak cycles. The mass spectrometer was a Hiden Analytical HAL IV RC RGA 301. Both mass spectrometer and the temperature controller were connected to a computer, which read and recorded the mass spectrometer and the temperature signal versus time.

To perform TDMS analysis, the material was first deposited as a thin film onto an 8 inch wafer using standard processing methods. The wafer was then placed in the TDMS vacuum system and the system was pumped down to a pressure below 1 e–7 torr. The temperature ramp was then starting using the temperature controller. The temperature and the mass spectrometer signal were recorded using the computer. For a typical measurement with a ramp rate of about 10 degree C per minute, one complete mass scan and one temperature measurement are recorded every 20 seconds. The mass spectrum at a given time and temperature at a given time can be analyzed after the measurement is competed.

EXAMPLES

Comparative A:

We measured the dielectric constant of a composition similar to Example 5 of our International Patent Publication WO 01/78110 and the dielectric constant was 2.7.

PREPARATIONS

Preparation 1

Preparation of Thermosetting Component (Referred to herein as "P1")

Step (a): Preparation of Mixture of 1,3,5,7-tetrakis(3'/4'-bromophenyl)adamantane (shown in FIG. 1A); 1,3/4-bis[1', 3',5'-tris(3"/4"-bromophenyl)adamant-7'-yl]benzene (shown in FIG. 1C); and at least 1,3-bis{3'/4'-[1",3",5"-tris(3'"/4'"-bromophenyl)adamant-7"-yl]phenyl}-5,7-bis(3""/4""-bromophenyl)adamantane (shown in FIG. 1C) (collectively "P1 Step (a) Product")

A first reaction vessel was loaded with adamantane (200 grams), bromobenzene (1550 milliliters), and aluminum trichloride (50 grams). The reaction mixture was heated to 40° C. by a thermostatted water bath. Tert-butyl bromide (1206 grams) was added slowly over a period of 4–6 hours to the reaction mixture. The reaction mixture at 40° C. was stirred overnight.

A second reaction vessel was loaded with 1000 milliliters of aqueous hydrogen chloride (5%w/w). The contents of the first reaction vessel were gradually discharged into the second reaction vessel while maintaining the reaction mixture at 25–35° C. by an external ice bath. An organic phase (dark brown lower phase) was separated and washed with water (1000 milliliters). About 1700 milliliters of the organic phase remained.

Figure 1B:
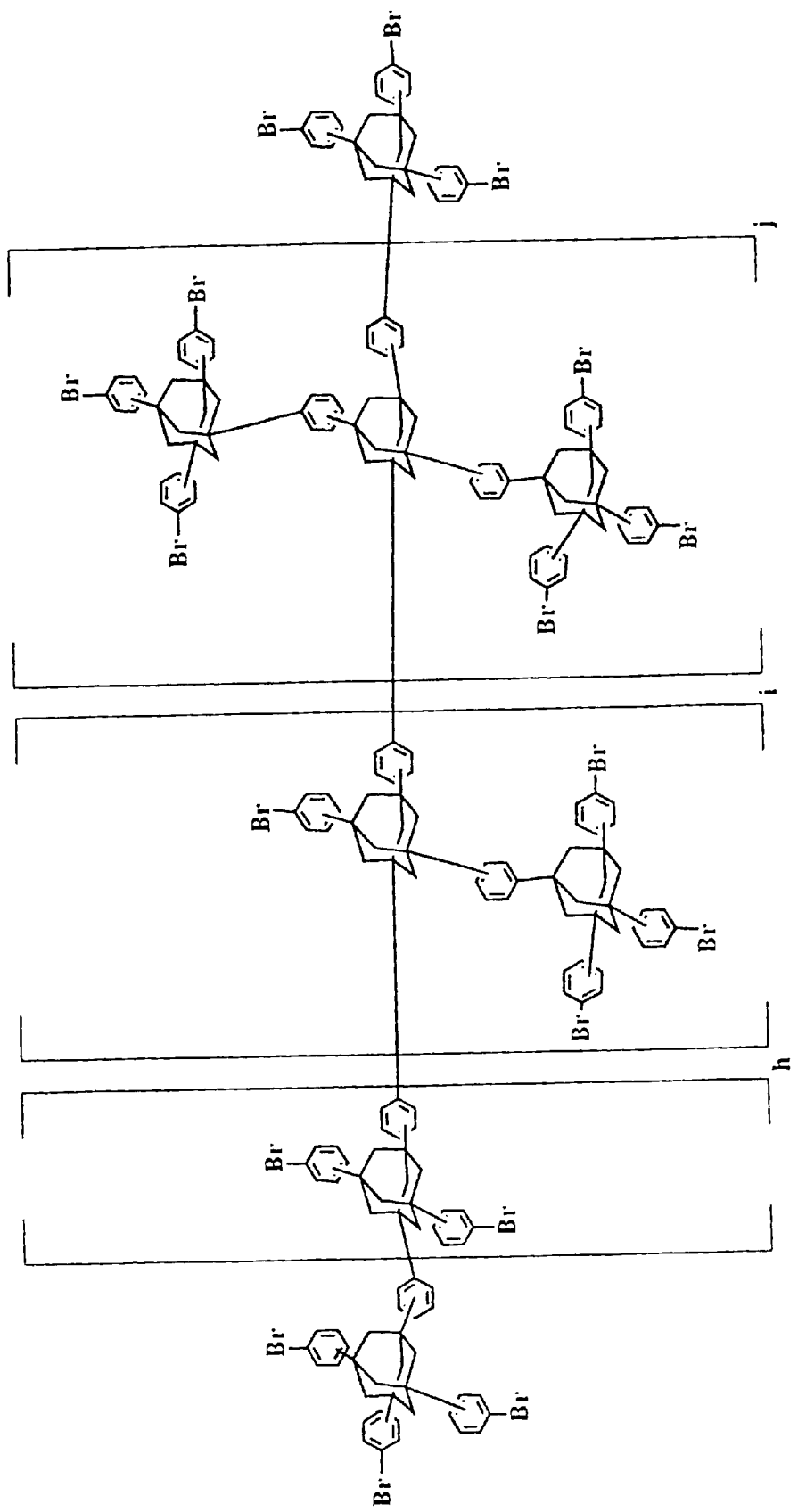
Figure 1C:
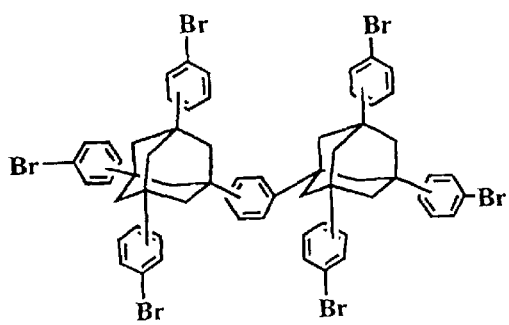
Figure 1C:
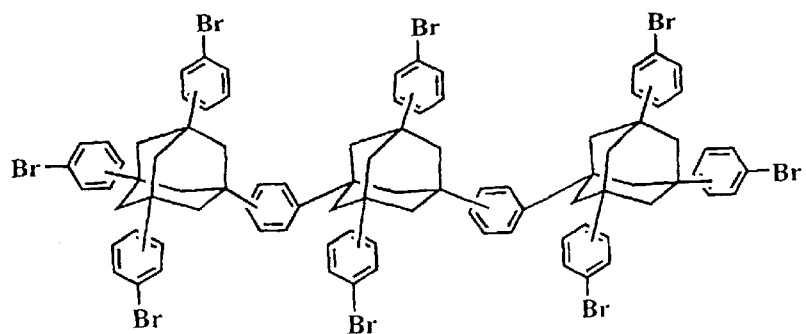

A third reaction vessel was loaded with 20.4 liters of petroleum ether (mainly isooctane with a boiling range of 80° C.–110° C.). The contents of the second reaction vessel were slowly added over a period of one hour to the third reaction vessel. The resulting mixture was stirred for at least one hour. The precipitate was filtered off and the filter cake was washed twice with 300 milliliters per wash of the aforementioned petroleum ether. The washed filter cake was dried overnight at 45° C. at 40 mbar. The P1 Step (a) Product yield was 407 grams dry weight. This reaction is shown in FIGS. 1A through 1C as follows. FIG. 1A shows the resulting monomer. FIG. 1B shows the resulting generic dimer and higher products while FIG. 1C shows the resulting specific dimer and trimer covered by the FIG. 1B structure.

Analytical techniques including GPC, HPLC, and NMR were used to identify the product. GPC analysis showed: 1,3,5,7-tetrakis(3'/4'-bromophenyl)adamantane (shown in FIG. 1A) had a peak molecular weight of 430; 1,3/4-bis[1', 3',5'-tris(3"/4"-bromophenyl)adamant-7'-yl]benzene (shown in FIG. 1C) had a peak molecular weight of 820; 1,3-bis{3'/ 4'-[1",3",5"-tris(3'"/4'"-bromophenyl)adamant-7"-yl] phenyl}-5,7-bis(3""/4""-bromophenyl)adamantane (shown in FIG. 1C) had a peak molecular weight of about 1150 (shoulder).

Step (b): Preparation of Mixture of 1,3,5,7-tetrakis[3',4'-(phenylethynyl)phenyl]adamantane (shown in FIG. 1D); 1,3/4-bis{1',3',5'-tris[3"/4"-(phenylethynyl)phenyl] adamant-7'-yl} benzene (shown in FIG. 1F); and at least 1,3-bis{3'/4'-[1",3",5"-tris[3'"/4 '"-(phenylethynyl)phenyl] adamantane-7"-yl]phenyl}-5,7-bis[3""/4""-(phenylethynyl) phenyl]adamantane (shown in FIG. 1F) (collectively "P1 Step (b) Product")

A first reactor under nitrogen was loaded with toluene (1500 milliliters), triethylamine (4000 milliliters), and the P1 Step (a) Product prepared above (1000 grams dry). The mixture was heated to 80° C. and bis-(triphenyl-phosphine) palladium(II)dichloride (i.e., [Ph$_3$P]$_2$PdCl$_2$) (7.5 grams) and tri-phenylphosphine (i.e. [Ph$_3$P]) (15 grams) were added. After ten minutes, copper(I)iodide (7.5 grams) was added.

Over a period of three hours, a solution of phenylacetylene (750 grams) was added to the first reactor. The reaction mixture at 80° C. was stirred for 12 hours to ensure that the reaction was complete. Toluene (4750 milliliters) was added. The solvent was then distilled off under reduced pressure and a maximum sump temperature and the reaction mixture was cooled down to about 50° C. The triethylammonium bromide (about 1600 milliliters) was filtered off. The filter cake was washed three times with 500 milliliters per wash of toluene. The organic phase was washed with 1750 milliliters of HCl (10 w/w %) and then washed with water (2000 milliliters).

To the washed organic phase, water (1000 milliliters), ethylene diamine tetraacetic acid (EDTA) (100 grams), and dimethylglyoxime (20 grams) were added. About 150 milliliters of NH$_4$OH (25 w/w %) were added to achieve a pH of 9. The reaction mixture was stirred for one hour. The organic phase was separated and washed with water (1000 milliliters). With a Dean-Stark trap, azeotropic drying occurred until water evolution ceased. Filtering agent dolomite (100 grams) (tradename Tonsil) was added. The mixture was heated to 100° C. for 30 minutes. Dolomite was filtered off with a cloth filter having fine pores and the remainder was washed with toluene (200 milliliters). Silica (100 grams) was added. The reaction mixture was stirred for 30 minutes. The silica was filtered off with a cloth filter having fine pores and the remainder was washed with toluene (200 milliliters). Aqueous NH$_3$ (20 w/w %), in an amount of 2500 milliliters, and 12.5 g of N-acetylcysteine were added. The phases were separated. The organic phase was washed with 1000 milliliters of HCl (10% w/w) and then washed two times with 1000 milliliters per wash of water. The toluene was distilled off under a reduced pressure of about 120 mbar. The pot temperature did not exceed about 70° C. A dark brown viscous oil (1500–1700 milliliters) remained. To the hot mass in the pot, iso-butyl acetate (2500 milliliters) was added and a dark brown solution formed (4250 milliliters).

Figure 1E:
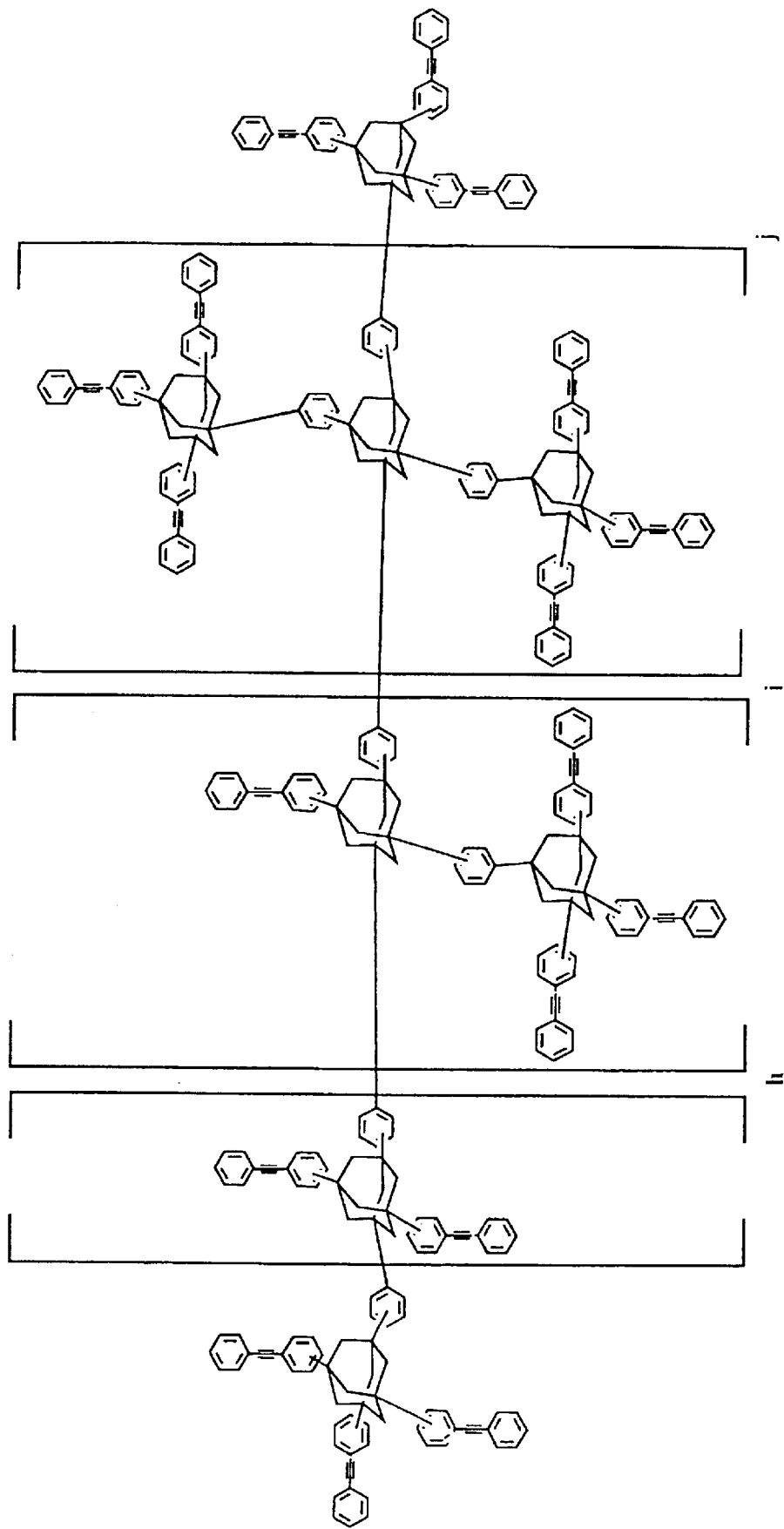
Figure 1F:
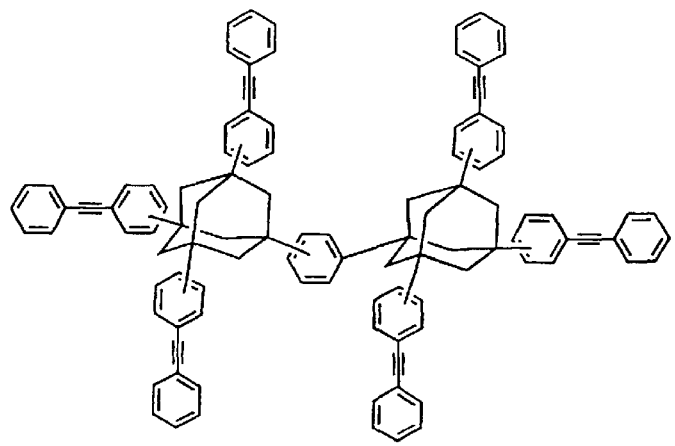
Figure 1F:
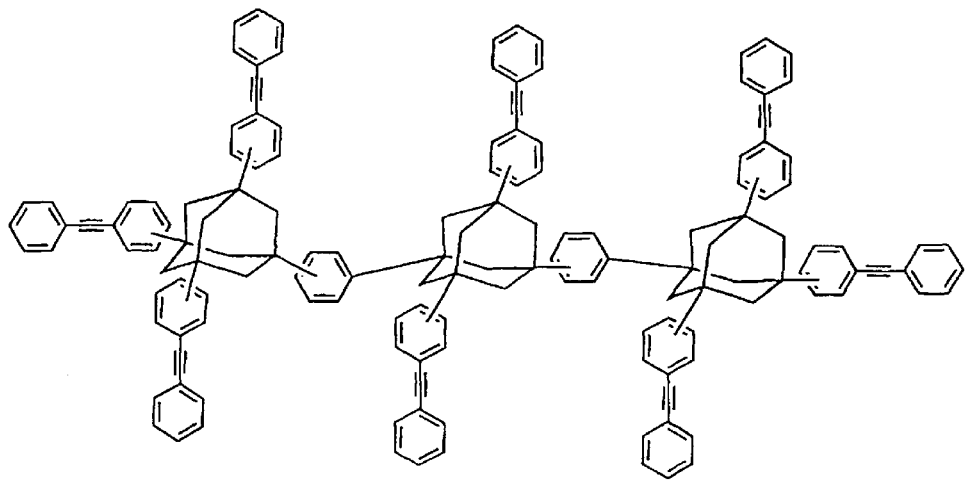

A second reactor was loaded with 17000 milliliters of petroleum ether (mainly isooctane with a boiling range of 80° C.–110° C.). The contents of the first reactor were added over a period of one hour to the second reactor and stirred overnight. The precipitate was filtered and washed four times with 500 milliliters per wash of the aforedescribed petroleum ether. The product was dried under reduced pressure for four hours at 45° C. and five hours at 80° C. The P1 Step (B) product yield was 850–900 grams. This reaction is shown in FIGS. 1D through 1F as follows. FIG. 1D shows the resulting monomer. FIG. 1E shows the resulting generic dimer and higher products while FIG. 1F shows the resulting specific dimer and trimer covered by the FIG. 1F structure.

Analytical techniques including GPC, HPLC, NMR, and FTIR were used to identify the product. GPC analysis showed: 1,3,5,7-tetrakis[3',4'-(phenylethynyl)phenyl] adamantane (shown in FIG. 1D) had a peak molecular weight of about 900; 1,3/4-bis{1',3',5'-tris[3"/4"-(phenylethynyl)phenyl]adamant-7'-yl} benzene (shown in FIG. 1F) had a peak molecular weight of about 1500; 1,3-bis{3'/4'-[1",3",5"-tris [3'"/4'"-(phenylethynyl)phenyl] adamant-7"-yl]phenyl}-5,7-bis[3""/4""-(phenylethynyl) phenyl]adamantane (shown in FIG. 1F) had a peak molecular weight of about 2100 (shoulder).

The melting point was 164–167° C. From NMR, a multiplet occurred at 6,9–8 ppm 2,8+–0,2H (aromatic part) and 1,7–2,7 ppm 1H+–0,2H (cage portion). From GPC, the ratio of the monomeric and small molecules to oligomeric compounds was 50±5%. FTIR showed the following:

| PEAKS IN CENTIMETERS$^{-1}$ (PEAK INTENSITY) | STRUCTURE |
| --- | --- |
| 3050 (weak) | Aromatic C—H |
| 2930 (weak) | Aliphatic C—H on adamantane |
| 2200 (very weak) | Acetylene |
| 1600 (very strong) | Aromatic C=C |
| 1500 (strong) | |
| 1450 (medium) | |
| 1350 (medium) | |

LC—MS study showed the presence of peaks:
of main monomeric product m/z 840,
of its derivatives, m/z 640, 740, 940; 706, 606, 806; 762, 662, 862; 938, 838, 1038
of dimeric products, m/z 1402, 1302, 1502; 1326, 1226, 1426.

The GPC 3 results follow.

| | Amount (Weight %) | | | | Peak Molecular Weight (Relative to PS) | | | | |
| --- | --- | --- | --- | --- | --- | --- | --- | --- | --- |
| Inc Mnmr | Mnmr | Dmr | Trmr | Hi Olgmr | Inc Mnmr | Mnmr | Dmr | Trmr | ΔR/R Mnmr |
| w/mnmr | 49.3 | 30.9 | 10.1 | 9.7 | | 744 | 1304 | 1676 | 0.10 |

Preparation 2

Preparation of Thermosetting Component (Referred to herein as "P2")

Step (a): Preparation of Mixture of 1,3,5,7-tetrakis(3'/4'-bromophenyl)adamantane (shown in FIG. 1A); 1,3/4-bis[1', 3',5'-tris(3"/4"-bromophenyl)adamant-7'-yl] benzene (shown in FIG. 1C); and at least 1,3-bis{3'/4'-[1",3",5"-tris (3'"/4'"-bromophenyl)adamant-7"-yl]phenyl}-5,7-bis(3""/ 4""-bromophenyl)adamantane(shown in FIG. 1C) (collectively "P2 Step (a) Product")

A first reaction vessel was loaded with 1,4-dibromobenzene (587.4 grams) and aluminum trichloride (27.7 grams). This reaction mixture was heated to 90° C. by a thermostatted water bath and maintained at this temperature for one hour without stirring and for an additional one hour with stirring. The reaction mixture was cooled down to 50° C. Adamantane (113.1 grams) was added to the cooled reaction mixture. Over a period of four hours, t-butyl-bromobenzene (796.3 grams) was added to the reaction mixture. The reaction mixture was stirred for an additional 12 hours.

A second reaction vessel was loaded with HCl (566 milliliters, 10% aqueous w/w). The contents of the first reaction vessel at 50° C. were discharged into the second reaction vessel while maintaining the mixture at 25–35° C. by an external ice bath. The reaction mass was a light brown suspension. The organic phase was a dark brown lower phase and separated from the reaction mixture. The separated organic phase was washed with water (380 milliliters). After this washing, about 800 milliliters of organic phase remained.

A third reaction vessel was loaded with heptane (5600 milliliters). Slowly over a period of one hour, the contents of the second reaction vessel were added to the third reaction vessel. The suspension was stirred for at least four hours and the precipitate was filtered off. The filter cake was washed twice with 300 milliliters per wash of heptane. The P2 Step (a) Product yield was 526.9 grams (wet) and 470.1 grams (dry).

Analytical techniques including GPC, HPLC, and NMR were used to identify the product. GPC analysis showed: 1,3,5,7-tetrakis(3'/4'-bromophenyl)adamantane (shown in FIG. 1A) had a peak molecular weight of about 430; 1,3/4-bis[1',3',5'-tris(3"/4"-bromophenyl)adamant-7'-yl] benzene (shown in FIG. 1C) had a peak molecular weight of about 820; 1,3-bis{3'/4'-[1",3",5"-tris(3'"/4'"-bromophenyl) adamant-7"-yl]phenyl}-5,7-bis(3""/4""-bromophenyl) adamantane (shown in FIG. 1C) had a peak molecular weight of about 1150 (shoulder).

Step (b): Preparation of Mixture of 1,3,5,7-tetrakis[3',4'-(phenylethynyl)phenyl]adamantane (shown in FIG. 1D); 1,3/4-bis{1',3',5'-tris[3"/4"-(phenylethynyl)phenyl] adamant-7'-yl}benzene (shown in FIG. 1F); and at least 1,3-bis{3'/4'-[1",3",5"-tris[3'"/4'"-(phenylethynyl)phenyl] adamant-7"-yl]phenyl}-5,7-bis[3""/4""-(phenylethynyl) phenyl]adamantane (shown in FIG. 1F) (collectively "P2 Step (b) Product")

A first reaction pot under nitrogen was loaded with toluene (698 milliliters), triethylamine (1860 milliliters), and the P2 Step (a) Product prepared above (465 grams dry). The mixture was heated to 80° C. Palladium-triphenylphosphine complex (i.e. [Ph(PPh$_3$)$_2$Cl$_2$](4.2 grams) was added to the reaction mixture. After waiting ten minutes, triphenylphosphine (i.e., PPh$_3$)(8.4 grams) was added to the reaction mixture. After waiting another ten mintues, copper(I)-iodide (4.2 grams) was added to the reaction mixture.

Over a period of three hours, a solution of phenylacetylene (348.8 grams) was added to the reaction mixture. The reaction mixture at 80° C. was stirred for 12 hours to ensure that the reaction was complete. Toluene (2209 milliliters) was added to the reaction mixture and then distilled off under reduced pressure and a maximum sump temperature. The reaction mixture was cooled down to about 50° C. and the triethylammonium bromide was filtered off. The filter cake was washed twice with 250 milliliters per wash of toluene. The organic phase was washed with HCl (10 w/w %)(500 milliliters) and water (500 milliliters).

To the organic phase, water (500 milliliters), EDTA (18.6 grams), and dimethylglyoxime (3.7 grams) were added. NH$_4$OH (25 w/w %)(about 93 milliliters) was added to keep the pH=9. The reaction mixture was stirred for one hour. The organic phase was separated from the insoluble material and the emulsion containing the palladium-complex. The separated organic phase was washed with water (500 milliliters). With a Dean-Stark trap, azeotropic drying of the washed organic phase occurred until water evolution ceased. Filtering agent dolomite (tradename Tonsil)(50 grams) was added and the reaction mixture was heated to 100° C. for 30 minutes. The dolomite was filtered off with a cloth filter having fine pores and the organic material was washed with toluene (200 milliliters). Silica (50 grams) was added and the reaction mixture was stirred for 30 minutes. The silica was filtered off with a cloth filter having fine pores and the organic material was washed with toluene (200 milliliters). Aqueous NH$_3$ (20% w/w)(250 milliliters) and N-acetylcysteine (12.5 grams) were added. The phases were separated. The organic phase was washed with HCl(10% w/w)(500 milliliters). The organic material was washed twice with 500 milliliters per wash of water. The toluene was distilled off under reduced pressure of about 120 mbar. The pot temperature did not exceed 70° C. A dark brown viscous oil (about 500–700 milliliters) remained. To the hot mass in the pot, iso-butyl acetate (1162 milliliters) was added. A dark brown solution (about 1780 milliliters) formed.

A second reaction pot was loaded with heptane (7120 milliliters). Over a period of one hour, the contents of the first reaction pot were added to the second reaction pot. The precipitate was stirred for at least three hours and filtered off. The product was washed four times with 250 milliliters per wash of heptane. The product was dried under reduced pressure of 40 mbar at 80° C. The P2 Step (b) Product yield was 700 grams wet or 419 grams dry.

Analytical techniques including GPC, HPLC, and NMR were used to identify the product. GPC analysis showed: 1,3,5,7-tetrakis[3',4'-(phenylethynyl)phenyl]adamantane (shown in FIG. 1D) had a peak molecular weight of about 900; 1,3/4-bis{1',3',5'-tris[3"/4"-(phenylethynyl)phenyl]adamant-7'-yl} benzene (shown in FIG. 1F) had a peak molecular weight of about 1500; 1,3-bis{3'/4'-[1",3",5"-tris[3'"/4'"-(phenylethynyl)phenyl]adamant-7"-yl]phenyl}-5,7-bis[3'"/4'"-(phenylethynyl)phenyl]adamantane (shown in FIG. 1F) had a peak molecular weight of about 2100 (shoulder).

The melting point was 164–167° C. From NMR, a multiplet occurred at 6,9–8 ppm 2,8+–0,2H (aromatic part) and 1,7–2,7 ppm 1H+–0,2H (cage portion). From GPC, the ratio of the monomeric and small molecules to oligomeric compounds was 50±5%. FTIR showed the following:

| PEAKS IN CENTIMETERS$^{-1}$ (PEAK INTENSITY) | STRUCTURE |
| --- | --- |
| 3050 (weak) | Aromatic C—H |
| 2930 (weak) | Aliphatic C—H on adamantane |
| 2200 (very weak) | Acetylene |
| 1600 (very strong) | Aromatic C=C |
| 1500 (strong) | |
| 1450 (medium) | |
| 1350 (medium) | |

LC—MS study showed the presence of peaks:
of main monomeric product m/z 840,
of its derivatives, m/z 640, 740, 940; 706, 606, 806; 762, 662, 862; 938, 838, 1038
of dimeric products, m/z 1402, 1302, 1502; 1326, 1226, 1426.

GPC 3 results follow.

| | Amount (Weight %) | | | | Peak Molecular Weight (Relative to PS) | | | | |
| --- | --- | --- | --- | --- | --- | --- | --- | --- | --- |
| Inc Mnmr | Mnmr | Dmr | Trmr | Hi Olgmr | Inc Mnmr | Mnmr | Dmr | Trmr | ΔR/R Mnmr |
| 7.7 | 36.4 | 26.8 | 12.3 | 16.8 | 546 | 763 | 1328 | 1672 | 0.14 |

Preparation 3

Impact of Solvent on ratio of 1,3,5,7-tetrakis[3',4'-(phenylethynyl)phenyl]adamantane (shown in FIG. 1D) to 1,3/4-bis{1',3',5'-tris[3"/4"-phenylethynyl)phenyl]adamant-7'-yl} benzene (shown in FIG. 1F) and at least 1,3-bis{3'/4'-[1",3",5"-tris[3'"/4'"-(phenylethynyl)phenyl]adamant-7"-yl]phenyl}-5,7-bis[3""/4""-(phenylethynyl) phenyl] adamantane (shown in FIG. 1F) 850 milliliters of P1 Step (a) Product was divided into four equal parts, and subjected to precipitation in petroleum ether, ligroine, heptane, and methanol. Each part was precipitated into 2520 ml of the solvent, vacuum filtered (Büchner funnel diam. 185 mm), washed on filter twice by 150 ml of the solvent, then dried in a vacuum oven for two hours at about 20° C., overnight at 40° C., and at 70–80° C. to constant weight.

Precipitation into hydrocarbons resulted in very dispersed light beige powders that dried without complications. Precipitation into methanol gave heavy, brownish granular solid (particles size approximately 1 mm), which formed tar when dried at 20° C. This product was dried further.

Reaction mixtures were analyzed by GPC during the reaction and before precipitation. All filtrates and final solids were analyzed by GPC and the results are in Table 4. In Table 4, PPT stands for precipitation, monomer is 1,3,5,7-tetrakis(3'/4'-bromophenyl)adamantane (shown in FIG. 1A); dimer is 1,3/4-bis[1',3',5'-tris(3"/4"-bromophenyl)adamant-7'-yl]benzene (shown in FIG. 1C); and trimer is 1,3-bis{3'/4'-[1",3",5"-tris(3'"/4'"-bromophenyl)adamant-7"-yl]phenyl}-5,7-bis(3""/4""-bromophenyl)adamantane (shown in FIG. 1C).

TABLE 4

| Peak Ratio [monomer to (dimer + trimer)] before PPT | Solvent For PPT | Peak Ratio [monomer to (dimer + trimer)] after PPT |
| --- | --- | --- |
| 75.0:25.0 | Petroleum Ether | 52.5:47.4 |
| 75.0:25.0 | Ligroine | 64.0:36.0 |
| 75.0:25.0 | Heptane | 66.2:33.8 |
| 75.0:25.0 | Methanol | 75.0:25.0 |

To summarize these results, the peak ratio of monomer to (dimer+trimer) in the reaction mixture was about 3:1. The product lost in hydrocarbons precipitation filtrates was mostly (>90%) monomer while losses in washing filtrates were negligible. There is no product in methanol precipitation filtrates. The monomer to (dimer+trimer) ratio after precipitation increases (1:1→3:1), and monomer losses in the filtrates decrease (56→0%) in the sequence: petroleum ether, ligroine, heptane, and methanol.

Preparation 4

Preparation of Thermosetting Component

The 1,3/4-bis{1',3',5'-tris[3"/4"-(phenylethynyl)phenyl] adamant-7'-yl} benzene (shown in FIG. 1F) in the Preparation 1 product mixture is separated using preparative liquid chromatography (PLC). PLC is similar to the HPLC method described above but uses larger columns to separate larger quantities of the mixture (from several grams to several hundred grams).

Preparation 5

Preparation of Thermosetting Component

The 1,3-bis{3'/4'-[1",3",5"-tris[3'"/4'"-(phenylethynyl) phenyl]adamant-7"-yl]phenyl}-5,7-bis[3""/4""-(phenylethynyl) phenyl]adamantane (shown in FIG. 1F) in the Preparation 1 product mixture is separated using preparative liquid chromatography (PLC).

Preparation 6

Preparation of Thermosetting Component

Figure 2:
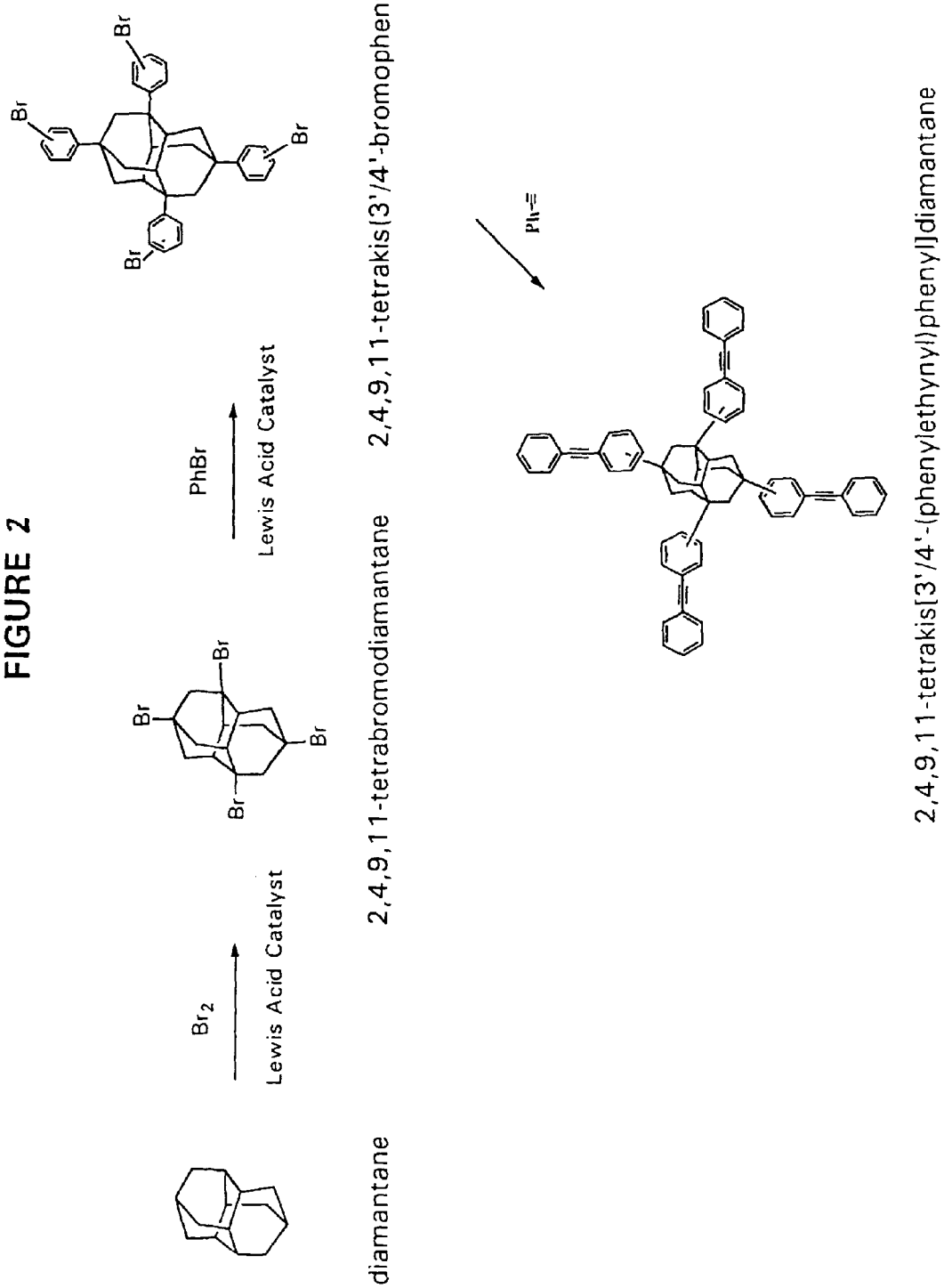
FIG. 2 illustrates one method for making diamantane based compositions useful as the thermosetting component in the present compositions.
Figure 3A:
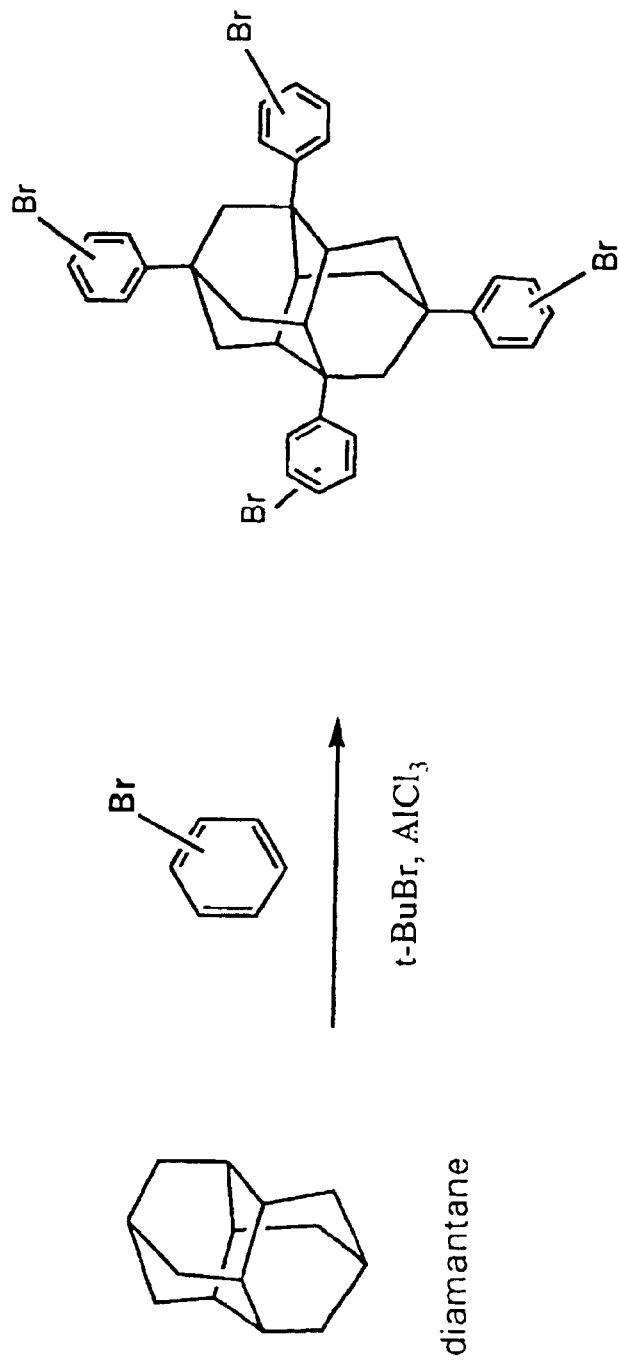
FIGS. 3A through 3F illustrate another method for making diamantane based compositions useful as the thermosetting component in the present compositions.
Figure 3B:
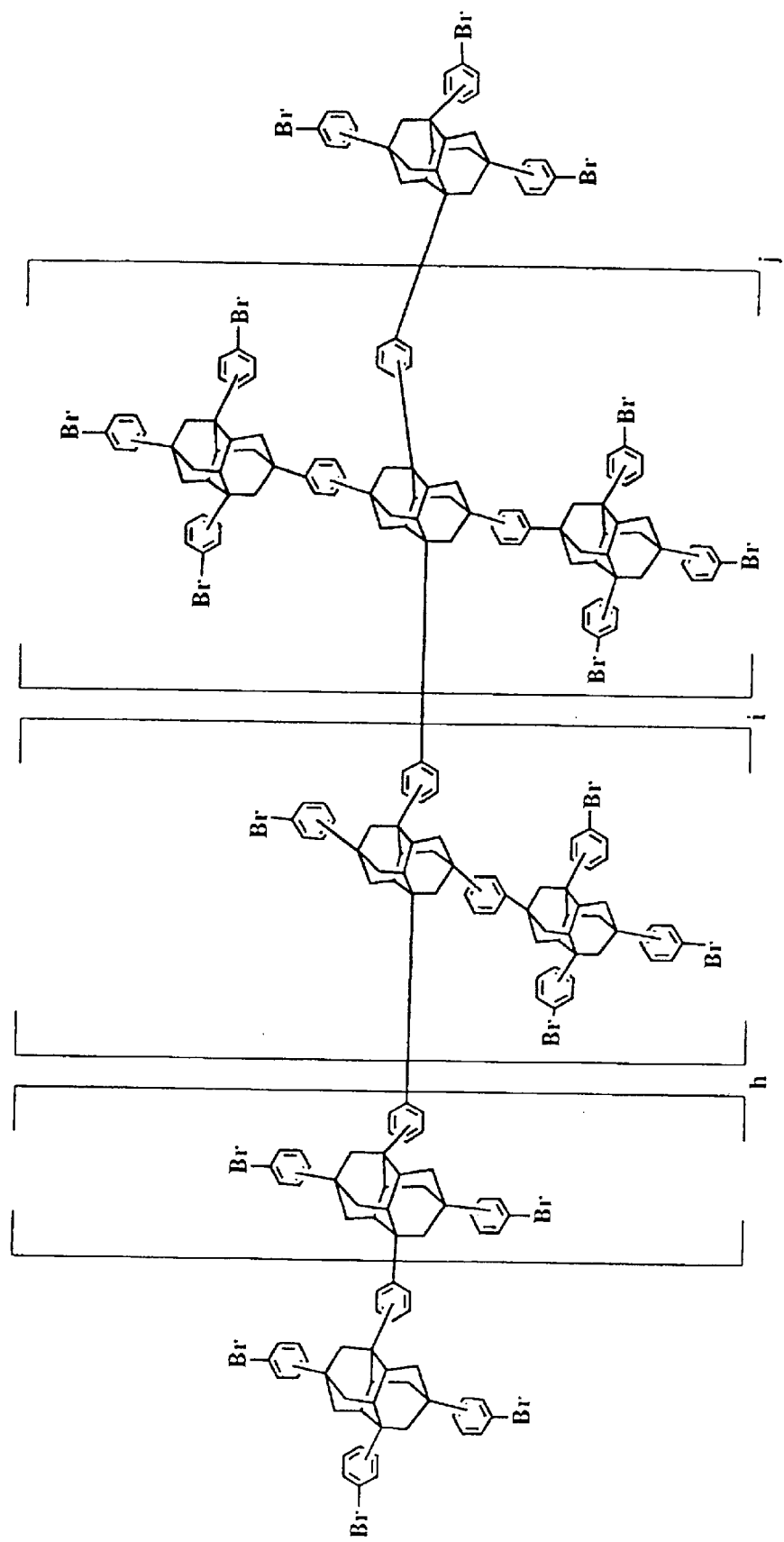
Figure 3C:
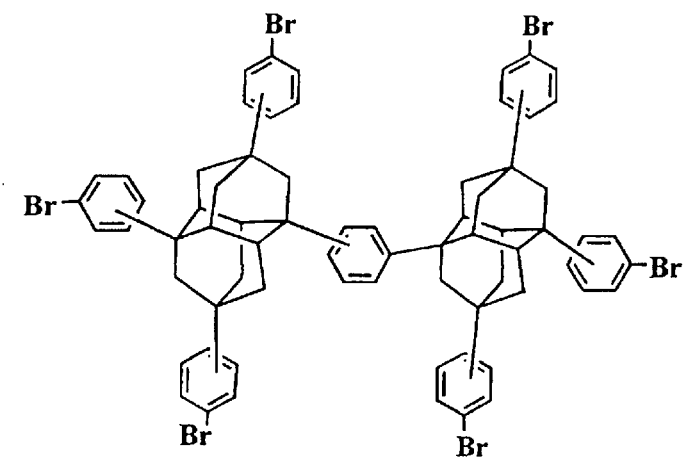
Figure 3C:
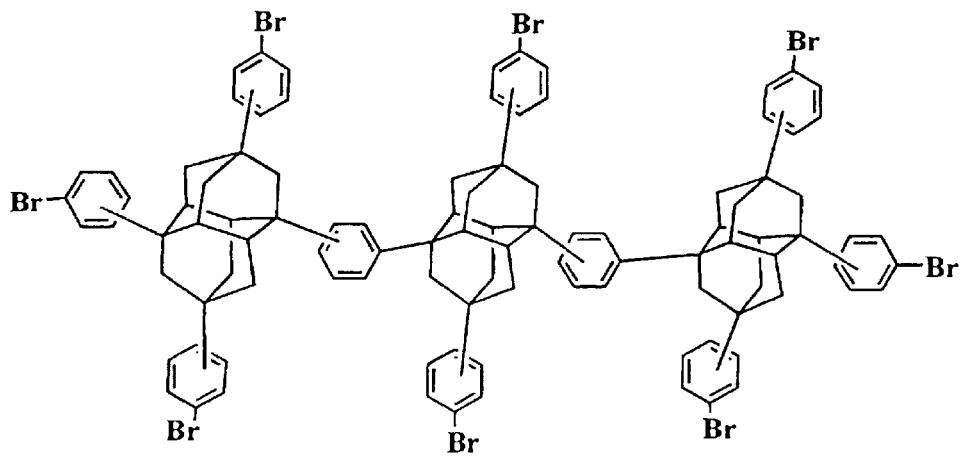
Figure 3D:
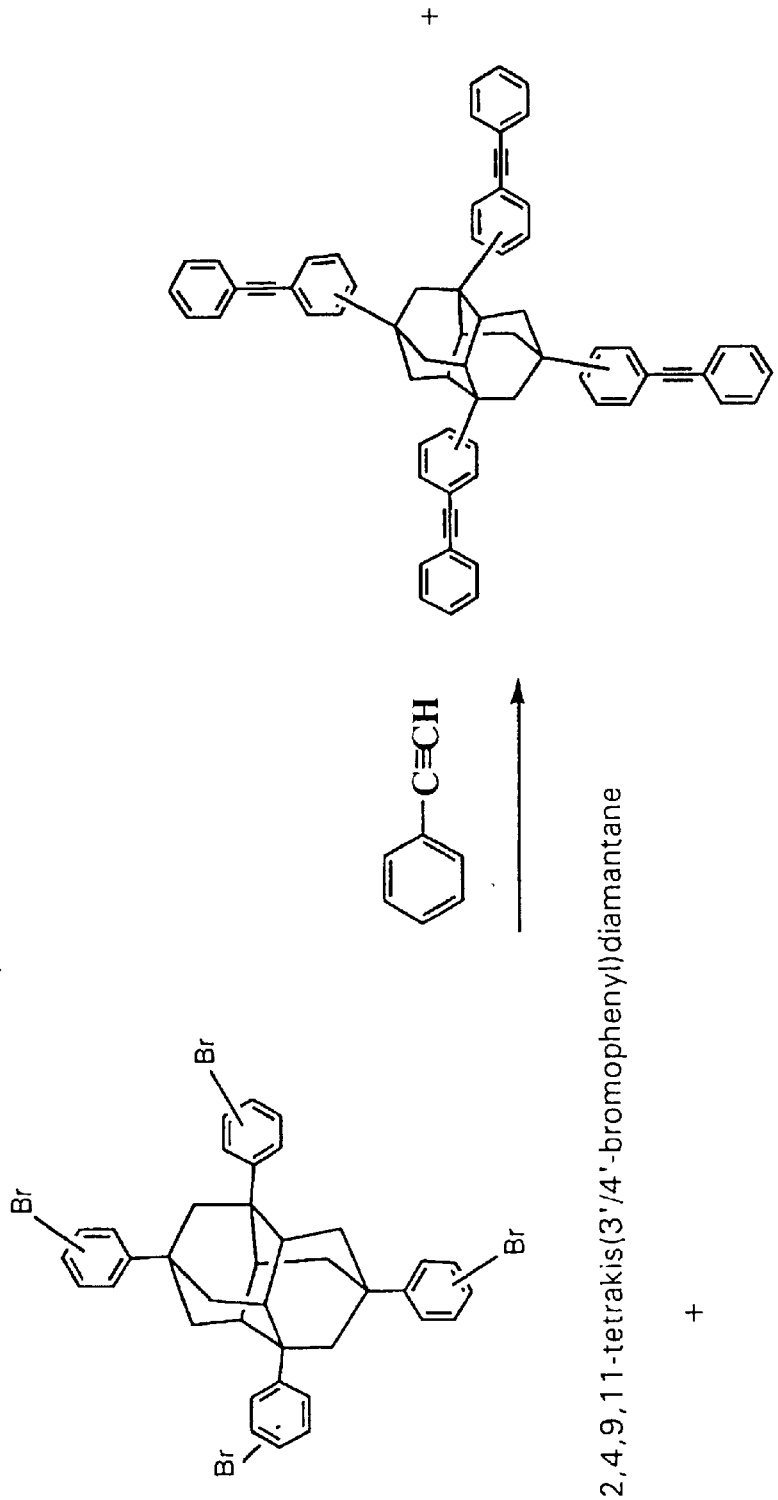
Figure 3E:
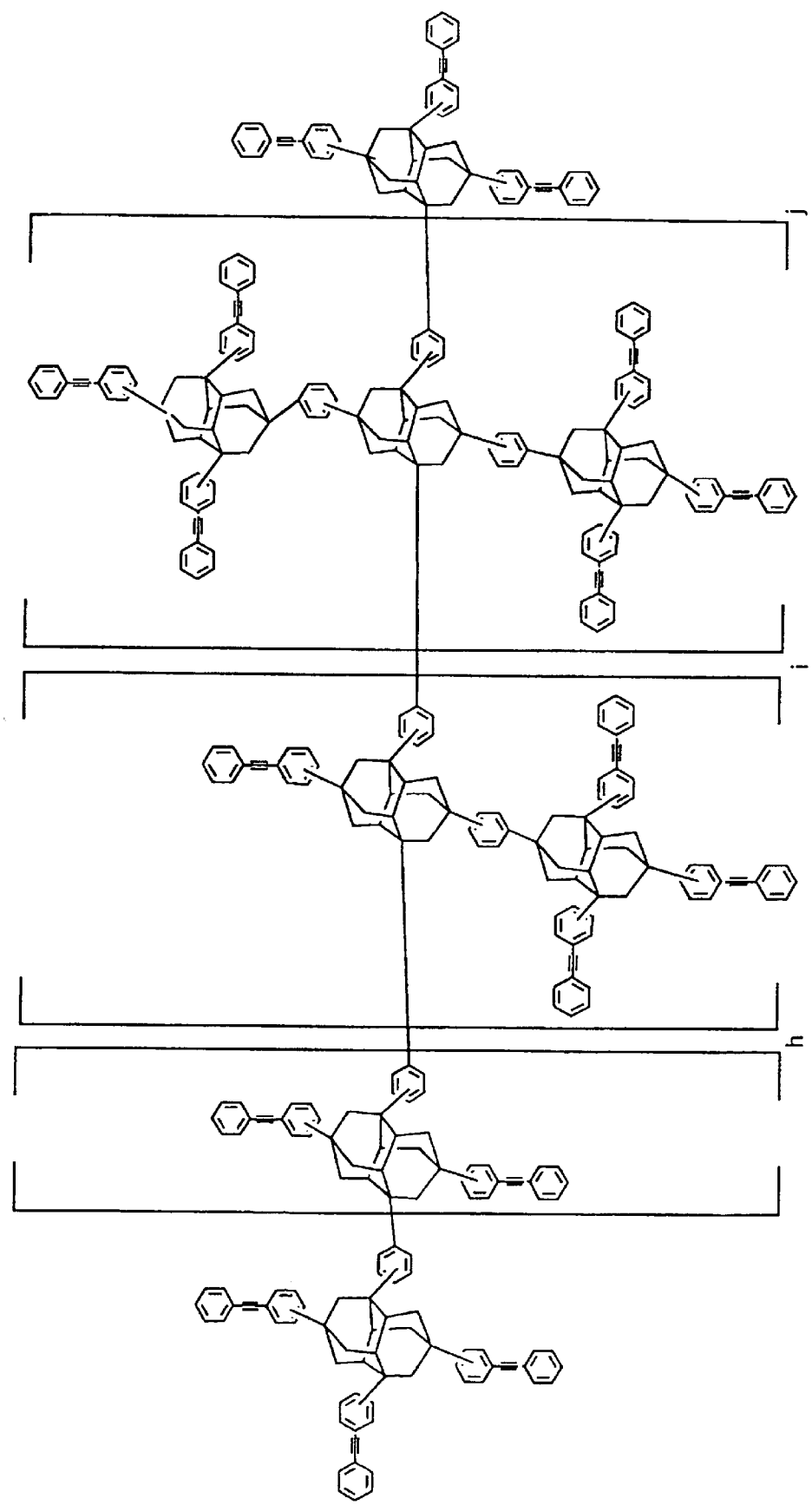
Figure 3F:
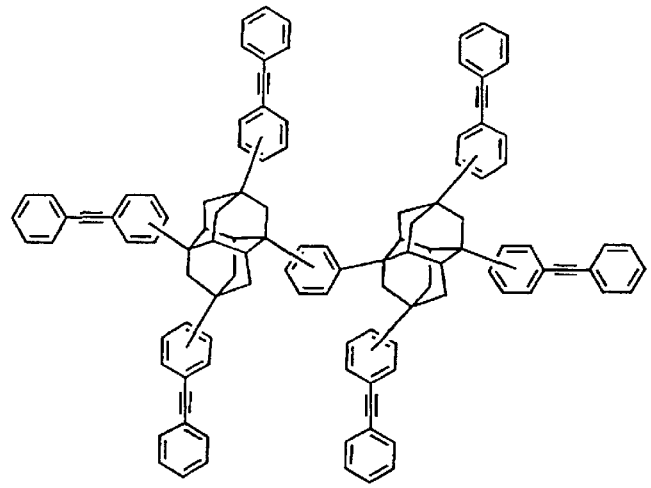
Figure 3F:
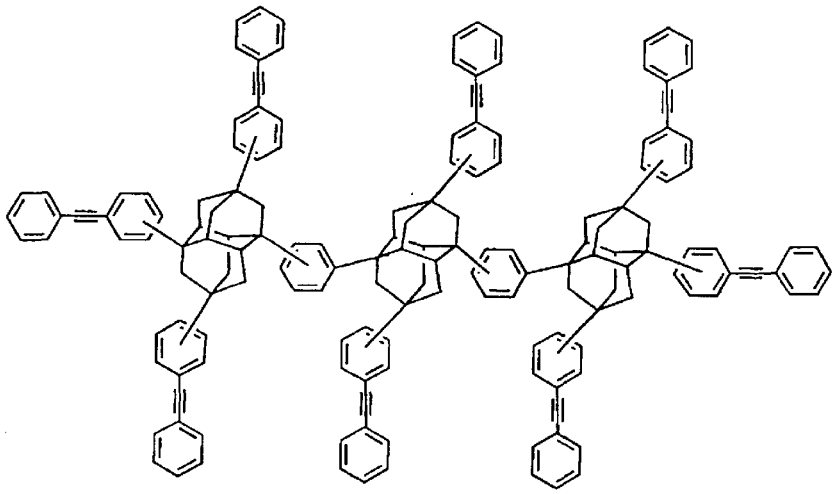

The diamantane monomer of Formula V and oligomer or polymer of diamantane monomer of Formulae VI, VII, X, XII, XV, XVI, and XVIII are prepared using the following method. As shown in FIG. 2, diamantane is converted using bromine and a Lewis Acid catalyst to brominated diamantane product. The brominated diamantane product is then reacted with bromobenzene in the presence of a Lewis Acid catalyst to form bromophenylated diamantane. The bromophenylated diamantane is then reacted with a terminal alkyne in the presence of a catalyst system as used in the so-called Sonogashira coupling reaction. The product at each step is worked up as described in our pending patent application PCT/US01/22204 filed Oct. 17, 2001.

Preparation 7

Preparation of Thermosetting Component (a)

The diamantane monomer of Formula V and oligomer or polymer of diamantane monomer of Formulae VI, VII, X, XII, XV, XVI, and XVIII are prepared using the following method. As shown in FIGS. 1A through 1F, diamantane is converted to the bromophenylated compositions of diamantane using similar synthetic procedures as described in Preparations 1 and 2. In FIGS. 1A through 1C, diamantane is reacted with a substituted halogen phenyl compound in the presence of a Lewis Acid catalyst as described in Preparations 1 and 2, and/or a second catalyst component as described in Preparation 2. A mixture of monomers, dimers, trimers, and higher oligomers is obtained after work-up of the reaction mixtures. In FIGS. 1D through 1F, the bromophenylated diamantane mixture is then reacted with a terminal alkyne in the presence of catalyst to produce the alkyne-substituted diamantane compositions of the present invention.

Inventive Example 1

In this example, the ethynyl containing group is first reacted with the thermosetting component.

To a 500-mL, 3 neck flask equipped with a condenser, a mechanical stirrer and a nitrogen inlet-outlet were added thermosetting component similar to Preparation 1 or 2 above (amount=20.00 grams (20.19 millimoles)); dichlorobis(triphenylphosphine)palladium(II)(amount=1.134 grams (1.62 millimoles)); triphenylphosphine (amount=0.848 gram (3.23 millimoles)); copper(I) iodide (amount=0.308 gram (1.62 millimoles)); triethylamine (amount=70 milliliters); and toluene (amount=80 milliliters). The mixture was heated to 80° C. and 4-ethynylaniline (amount=0.63 gram (5.2 millimoles)) in 20 milliliters of triethylamine were added to the reaction mixture dropwise. The reaction mixture was heated at 80° C. for 8 hours and then phenylacetylene (amount=16.50 grams (161.6 millimoles)) and triethylamine (amount=20 milliliters) were added to the reaction mixture dropwise. The solution was heated at 80° C. for 8 hours.

The reaction mixture was cooled to room temperature and transferred to a 1 liter, 3 neck flask equipped with a condenser, a mechanical stirrer and a nitrogen inlet-outlet and toluene (100 milliliters) was added. The solution was then neutralized with 6N HCl. The resulting water was removed. The toluene solution was then stirred with 100 mL of 6N HCl at 60° C. for 30 minutes. The mixture was filtered through celite® naturally occurring inorganic material. The aqueous solution was then removed. The HCl extraction was repeated for two more times. The toluene solution was then washed with 100 mL of deionized water twice. The solution was stirred with 100 mL of 0.1 M of N-acetyl-cysteine in ammonia solution at 60° C. for 30 min. The aqueous solution was then removed. The ammonia extraction was repeated for five more times. The toluene was then removed by rotary evaporator and the resulting solid was dried under vacuum overnight to yield 17.10 grams (85.05%) of reddish solid (called Solid A).

Figure 12:
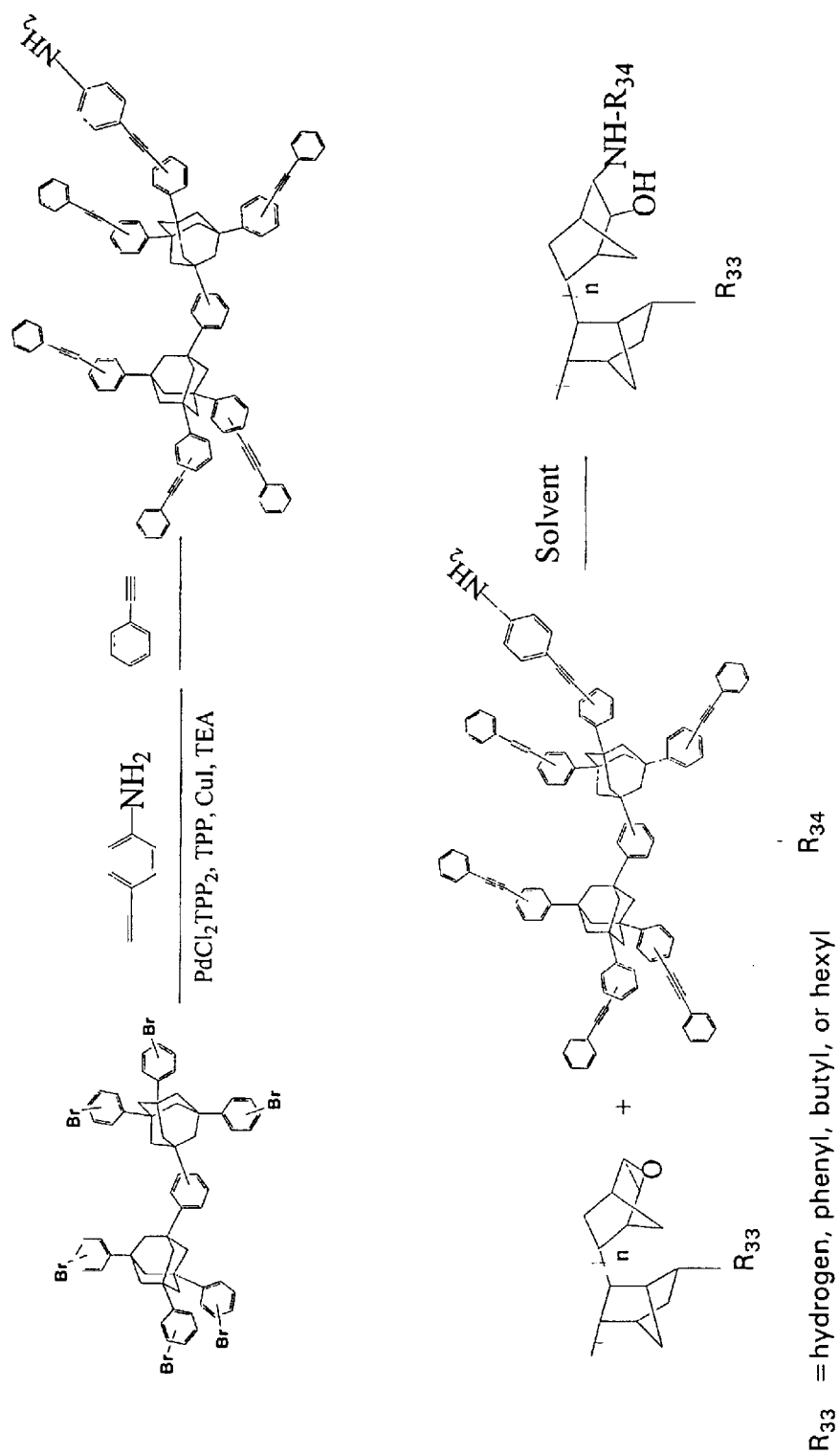
FIG. 12 illustrates the reaction scheme of Inventive Example 1.

To a 100-mL, 3 neck flask equipped with a condenser, a magnetic stirrer and a nitrogen inlet-outlet were added 20.70 mg (60% dispersion in mineral oil, which corresponds to 0.5176 mmol) of sodium hydride, and 20 ml of hexane. The mixture was stirred at room temperature for 5 minutes and upper hexane layer was decanted. To the above mixture were added tetrahydrofuran (amount=20 millilters)(THF) and 1.00 g of the above Solid A. The mixture was stirred at room temperature for 30 minutes and then epoxy functionalized polynorbornene (amount=0.6540 gram) was added. The solution was then heated at 65° C. for 12 hours. THF was then removed by rotary evaporator and the resulting mixture was dissolve in 15 ml of xylene (called Solution B). This solution was washed by de-ionized water for 3 times. The preceding reaction scheme is shown in FIG. 12 where although only 1,3/4-bis[1',3',5'-tris(3"/4"-bromophenyl) adamant-7'-yl]benzene is shown, it is understood that similar reactions occur for 1,3,5,7-tetrakis(3'/4'-bromophenyl) adamantane and 1,3-bis{3'/4'-[1",3",5"-tris(3'"/4'"-bromophenyl)adamant-7"-yl]phenyl}-5,7-bis{3""/4""-bromophenyl)adamantane.

To a 65-mL plastic bottle was added the above Solution B and ortho-cresol novolac (amount=0.030 gram; molecular weight of 1760; supplied by Schenectady International Inc.). The solution was stirred at room temperature for 1 hour. The solution was then filtered through a 0.1 μm teflon filter.

Figure 13:
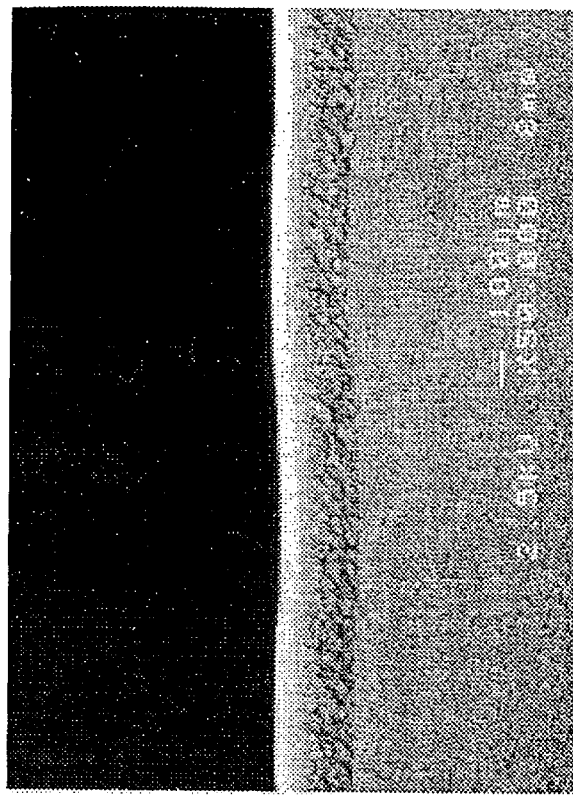
FIG. 13 shows scanning electron microscopy pictures for the cross section and surface of the film of Inventive Example 1.
Figure 13:
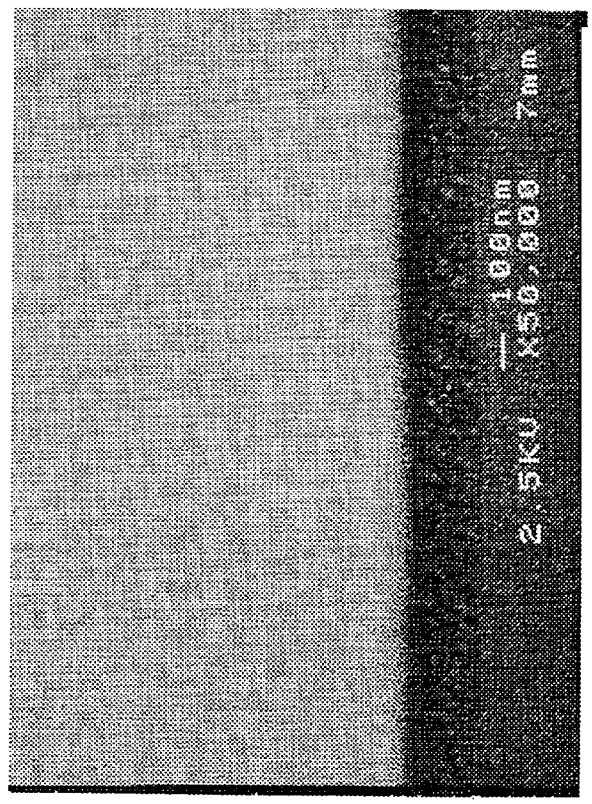

The composition was applied to a substrate using typical coating conditions known to those skilled in the art. The resulting spun-on composition was baked for one minute under $N_2$ (<50 ppm $O_2$) at each of the following temperatures: 125° C., 250° C., and 300° C. The furnace cure condition was 400° C. for 60 minutes in $N_2$ (26 liters/minute) with ramping up from 250° C. at 5° K per minute. The cure temperature range was from 350° C. to 450° C. In each composition, the porogen decomposed and the decomposed porogen volatilized whereby pores formed in the composition. The layer had a refractive index of 1.433 and a thickness of 2414 Angstroms. FIG. 13 shows the Scanning Electronic Microscope results.

Inventive Example 2

In this example, the ethynyl containing group is first reacted with the porogen.

To a 500-milliliter, 3 neck flask equipped with a condenser, a magnetic stirrer and a nitrogen inlet-outlet were added sodium hydride (amount=0.262 gram (60% dispersion in mineral oil, which corresponds to 6.54 millimoles)), and hexane (amount=60 milliliters). The mixture was stirred at room temperature for 5 minutes and the upper hexane layer was decanted. To the above mixture were added 4-ethynylaniline (amount=0.695 gram (5.93 millimoles)) and tetrahydrofuran (THF, amount=144 grams). The solution was stirred at room temperature for 1 hour and epoxy functionalized polynorbornene (amount=15 grams) was added. The reaction mixture was heated at 60° C. for 12 hours. THF was then removed by rotary evaporator and the resulting mixture was dissolve in 50 ml of toluene to form a solution (referred to below as Solution A).

To a 500-milliliter, 3 neck flask equipped with a condenser, a mechanical stirrer and a nitrogen inlet-outlet were added thermosetting component similar to Preparation 1 or 2 above (amount=25.75 grams (26.00 millimoles)), dichlorobis(triphenylphosphine)palladium(II) (amount=1.461 grams(2.081 millimoles)), triphenylphosphine (amount=1.092 gram(4.162 millimoles)), copper(I) iodide (amount=0.3963 gram(2.081 millimoles)), triethylamine (amount=160 milliliters), and toluene (amount=80 milliliters). The mixture was heated to 80° C. and the above Solution A was added to the reaction mixture dropwise. The reaction mixture was heated at 80° C. for 12 hours and then phenylacetylene (amount=21.3 grams (208.1 millimoles)) and toluene (amount=30 milliliters) were added to the reaction mixture dropwise. The solution was heated at 80° C. for 4 hours.

Figure 14:
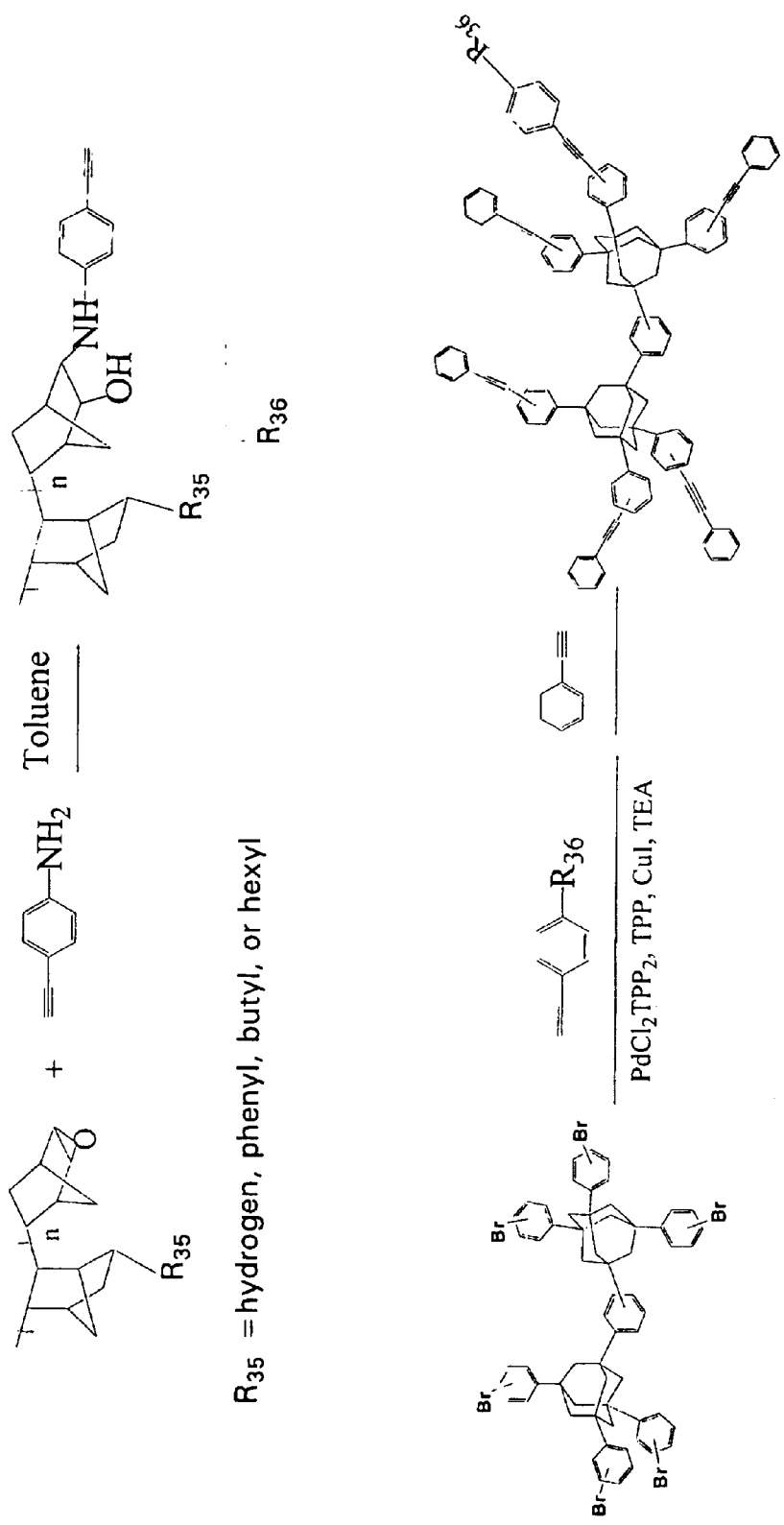
FIG. 14 illustrates the reaction scheme of Inventive Example 2.

The reaction mixture was cooled to room temperature and transferred to a 1 liter, 3 neck flask equipped with a condenser, a mechanical stirrer and a nitrogen inlet-outlet and toluene (amount=100 milliliters) was added. The solution was then neutralized with 6N HCl. The resulting water was removed. The toluene solution was then stirred with 100 mL of 6N HCl at 60° C. for 30 min. The mixture was filtered through celite ® naturally occurring inorganic material. The aqueous solution was then removed. The HCl extraction was repeated for two more times. The toluene solution was then washed with 100 mL of deionized water twice. The solution was stirred with 100 mL of 0.1 M of N-acetyl-cysteine in ammonia solution at 60° C. for 30 min. The aqueous solution was then removed. The ammonia extraction was repeated for five more times. The toluene was then removed by rotary evaporator and the resulting solid was dried under vacuum overnight. The preceding reaction scheme is shown in FIG. 14 where although only 1,3/4-bis[1',3',5'-tris(3"/4"-bromophenyl)adamant-7'-yl]benzene is shown, it is understood that similar reactions occur for 1,3,5,7-tetrakis(3'/4'-bromophenyl)adamantane and 1,3-bis {3'/4'-[1",3",5"-tris (3'''/4'''-bromophenyl)adamant-7"-yl]phenyl}-5,7-bis{3''''/4''''-bromophenyl)adamantane.

To a 125-milliliter plastic bottle were added 4.48 g of the above solid, 0.047 g of ortho-cresol novolac (amount=0.047 gram; molecular weight of 1760; supplied by Schenectady International Inc.) and xylenes (40.74 grams). The solution was stirred at room temperature for 1 hour. The solution was then filtered through a 0.1 μm teflon filter.

Figure 15:
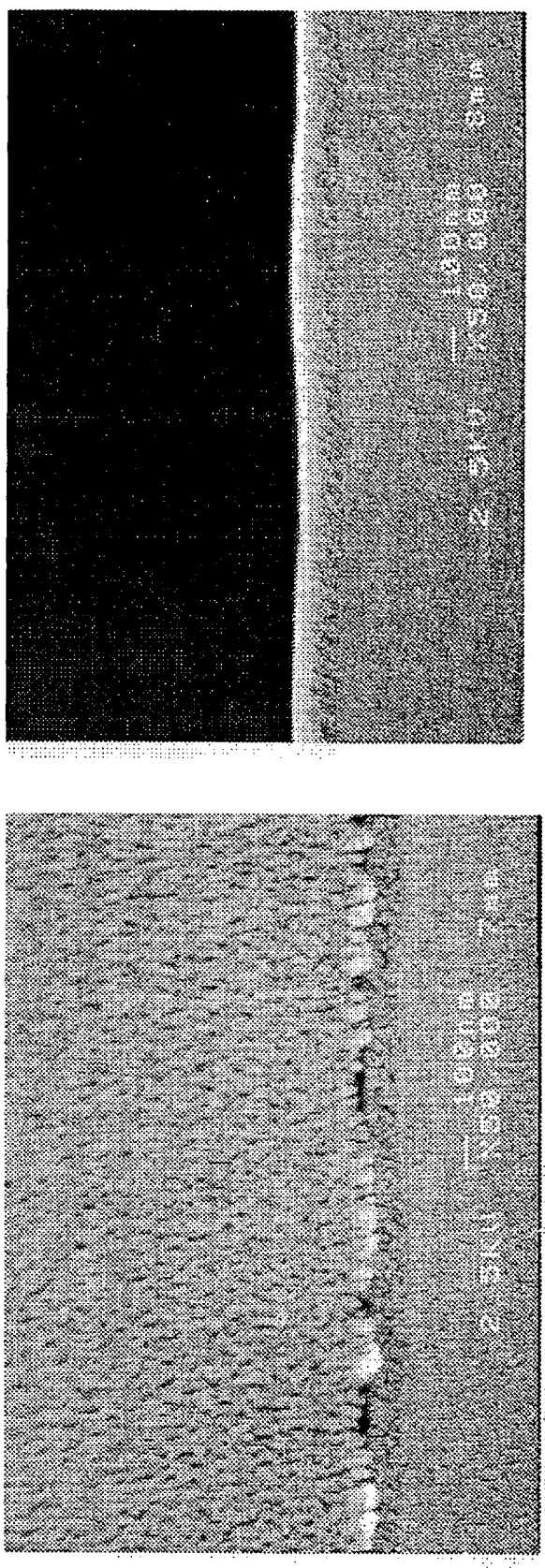
FIG. 15 shows scanning electron microscopy pictures for the cross section and surface of the film of Inventive Example 2.

The composition was applied to a substrate using typical coating conditions known to those skilled in the art The resulting spun-on composition was baked for one minute under $N_2$ (<50 ppm $O_2$) at each of the following temperatures: 125° C., 250° C., and 300° C. The furnace cure condition was 400° C. for 60 minutes in $N_2$ (26 liters/minute) with ramping up from 250° C. at 5° K per minute. The cure temperature range was from 350° C. to 450° C. In each composition, the porogen decomposed and the decomposed porogen volatilized whereby pores formed in the composition. After bake, the layer had a refractive index of 1.636 and a thickness of 1255 Angstroms. After cure, the layer had a refractive index of 1.398 and a thickness of 1056 Angstroms. FIG. 15 shows Scanning Electron Microscope results.

Inventive Example 3

In this example, the ethynyl containing group is first reacted with the porogen.

To a 300-milliliter, 3 neck flask equipped with a condenser, a magnetic stirrer and a nitrogen inlet-outlet were added triphenylphosphine (amount=9.76 grams (37.2 millimoles)), diethyl azodicarboxylate (amount=6.49 grams (37.2 millimoles)), 3-hydroxyphenylacetylene (amount=4.00 grams (33.9 millimoles)), and tetrahydrofuran (THF; amount=90 milliliters). A clear solution was obtained after the mixture was stirred at room temperature for 5 minutes. To this solution was then added 10.76 g of polycaprolactone in 40 ml of THF solution dropwise at room temperature. The solution was stirred at room temperature for 12 hours. THF was then partially removed by rotary evaporator to make a 40 ml viscous solution and ethyl ether (amount=50 milliliters) was added to the mixture and put into refrigerator for 30 min. The precipitate that formed was removed by filtration. Ethyl ether in the filtrate was then removed by rotary evaporator. To this viscous solution was added methylene chloride (50 milliliters) and put into refrigerator overnight. The precipitation that formed was removed by filtration. The solvent was then removed by rotary evaporator to yield a viscous liquid (referred to belows as Liquid A).

To a 500-mL, 3 neck flask equipped with a condenser, a mechanical stirrer and a nitrogen inlet-outlet were added thermosetting component similar to Preparation 1 or 2 above (amount=13.34 grams (13.47 millimoles)), dichlorobis (triphenylphosphine)palladium(II) (amount=0.7566 gram (1.078 millimoles)), triphenylphosphine (amount=0.5655 gram(2.156 millimoles), copper(I) iodide (amount=0.2053 gram(1.078 millimoles), triethylamine (amount=110 milliliters). The mixture was heated to 80° C. and 12.30 g of the above Liquid A with toluene (amount=40 milliliters) was added to the reaction mixture dropwise. The reaction mixture was heated at 80° C. for 12 hours and then 10.32 g (101.1 mmol) of phenylacetylene and toluene (amount=30 milliliters) were added to the reaction mixture dropwise. The solution was heated at 80° C. for 4 hours.

Figure 16:
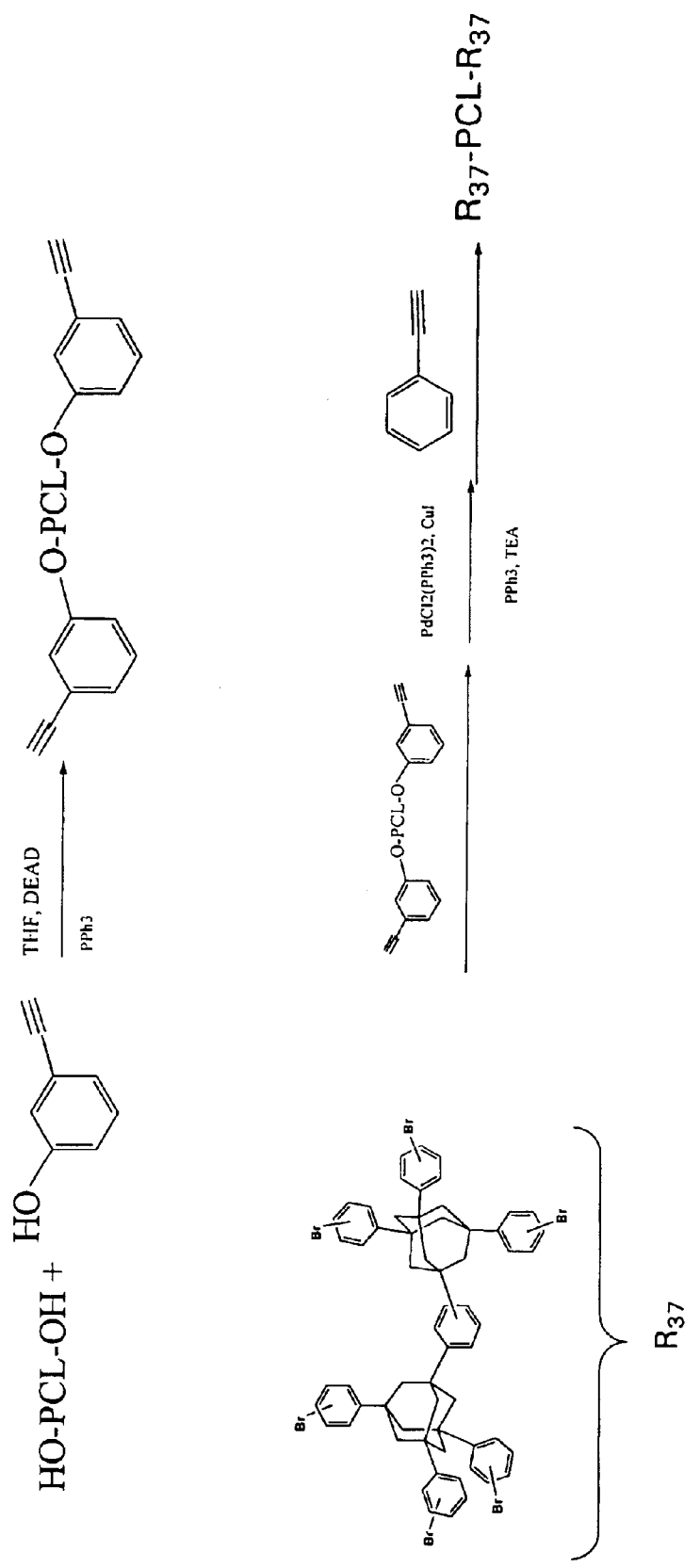
FIG. 16 illustrates the reaction scheme of Inventive Example 3.

The reaction mixture was cooled to room temperature and transferred to a 1 liter, 3 neck flask equipped with a condenser, a mechanical stirrer and a nitrogen inlet-outlet and toluene (amount=100 milliliters) was added. The solution was then neutralized with 6N HCl. The resulting water was removed. The toluene solution was then stirred with 100 mL of 6N HCl at 60° C. for 30 min. The mixture was filtered through celite®. The aqueous solution was then removed. The HCl extraction was repeated for two more times. The toluene solution was then washed with 100 mL of deionized water twice. The solution was stirred with 100 mL of 0.1 M of N-acetyl-cysteine in ammonia solution at 60° C. for 30 min. The aqueous solution was then removed. The ammonia extraction was repeated for five more times. The toluene was then removed by rotary evaporator and the resulting solid was dried under vacuum overnight. The preceding reaction scheme is shown in FIG. 16 where although only 1,3/4-bis[1',3',5'-tris(3"/4"-bromophenyl)adamant-7'-yl]benzene is shown, it is understood that similar reactions occur for 1,3,5,7-tetrakis(3'/4'-bromophenyl)adamantane and 1,3-bis{3'/4'-[1",3",5"-tris(3'''/4'''-bromophenyl)adamant-7"-yl]phenyl}-5,7-bis{3'''/4'''-bromophenyl)adamantane.

To a 125-milliliter plastic bottle were added 2 grams of the above solid, polycarbosilane $(CH_2SiH_2)_q$ where q is 20–30 (amount=0.1334 gram; supplied by Starfire Systems, Inc.) and 20 g of xylenes (amount=20 grams). The solution was heated at 145° C. for 15.5 hours. The solution was then filtered through a 0.1 µm teflon filter.

The composition was applied to a substrate using typical coating conditions known to those skilled in the art. The resulting spun-on composition was baked for one minute under $N_2$ (<50 ppm $O_2$) at each of the following temperatures: 125° C., 250° C., and 300° C. The furnace cure condition was 400° C. for 60 minutes in $N_2$ (26 liters/minute) with ramping up from 250° C. at 5° K per minute. The cure temperature range was from 350° C. to 450° C. In each composition, the porogen decomposed and the decomposed porogen volatilized whereby pores formed in the composition. After bake, the layer had a refractive index of 1.617 and a thickness of 5640 Angstroms. After cure, the layer had a refractive index of 1.593 and a thickness of 3784 Angstroms. The above formulation without the adhesion promoter had an after base refractive index of 1.639, an after bake thickness of 1369 Angstroms, an after cure refractive index of 1.584, an after cure thickness of 993 Angstroms, a degassed dielectric constant of 2.66, and an additional cure refractive index of 1.562.

What is claimed is:

1. A composition comprising:

(a) thermosetting component comprising: (1) optionally monomer of Formula I

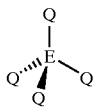

and (2) at least one oligomer or polymer of Formula II

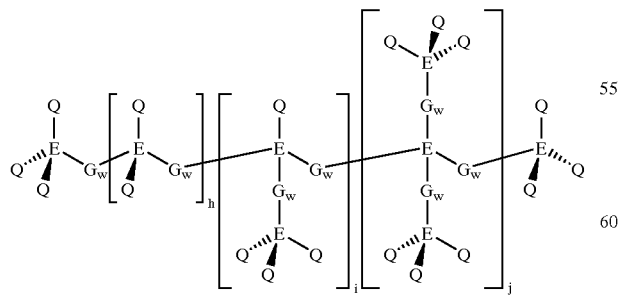

where said E is a cage compound; each of said Q is the same or different and selected from aryl, branched aryl, and substituted aryl wherein said substituents include hydrogen, halogen, alkyl, aryl, substituted aryl, heteroaryl, aryl ether, alkenyl, alkynyl, alkoxyl, hydroxyalkyl, hydroyaryl, hydroxyalkenyl, hydroxyalkynyl, hydroxyl, or carbonyl; said G is aryl or substituted aryl where substituents include halogen and alkyl; said h is from 0 to 10; said i is from 0 to 10; said j is from 0 to 10; and said w is 0 or 1;

(b) porogen that bonds to said thermosetting component (a).

2. The composition of claim 1 wherein said thermosetting component (a) is functionalized.

3. The composition of claim 2 wherein said functionality is selected from the group consisting of acetylene; 4-ethynylaniline; 3-hydroxyphenylacetylene; 4-fluorophenylacetylene; and 1-ethylcyclohexylamine.

4. The composition of claim 1 wherein said porogen comprises a material having a decomposition temperature less than the glass transition temperature of said thermosetting component (a) and greater than the curing temperature of said thermosetting component (a).

5. The composition of claim 4 wherein said porogen is selected from the group consisting of unsubstituted polynorbornene, substituted polynorbornene, polycaprolactone, unsubstituted polystyrene, substituted polystyrene, polyacenaphthylene homopolymer, and polyacenaphthylene copolymer.

6. The composition of claim 5 wherein said porogen is functionalized.

7. The composition of claim 6 wherein said functionality is selected from the group consisting of epoxy, hydroxy, carboxylic acid, amino, and ethynyl.

8. The composition of claim 1 wherein said porogen is covalently bonded to said thermosetting component (a).

9. The composition of claim 8 wherein said porogen is covalently bonded to said thermosetting component (a) through an ethynyl containing group.

10. The composition of claim 9 wherein said ethynyl containing group is acetylene.

11. The composition of claim 8 wherein said thermosetting component (a) comprises (1) adamantane monomer of Formula III

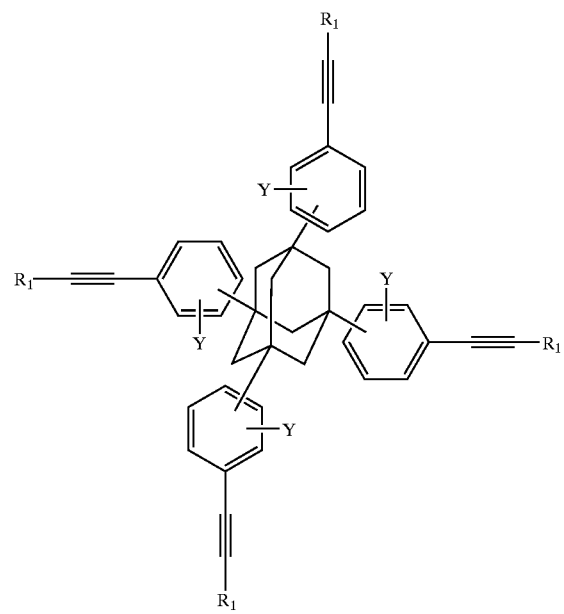

and (2) adamantane oligomer or polymer of Formula IV

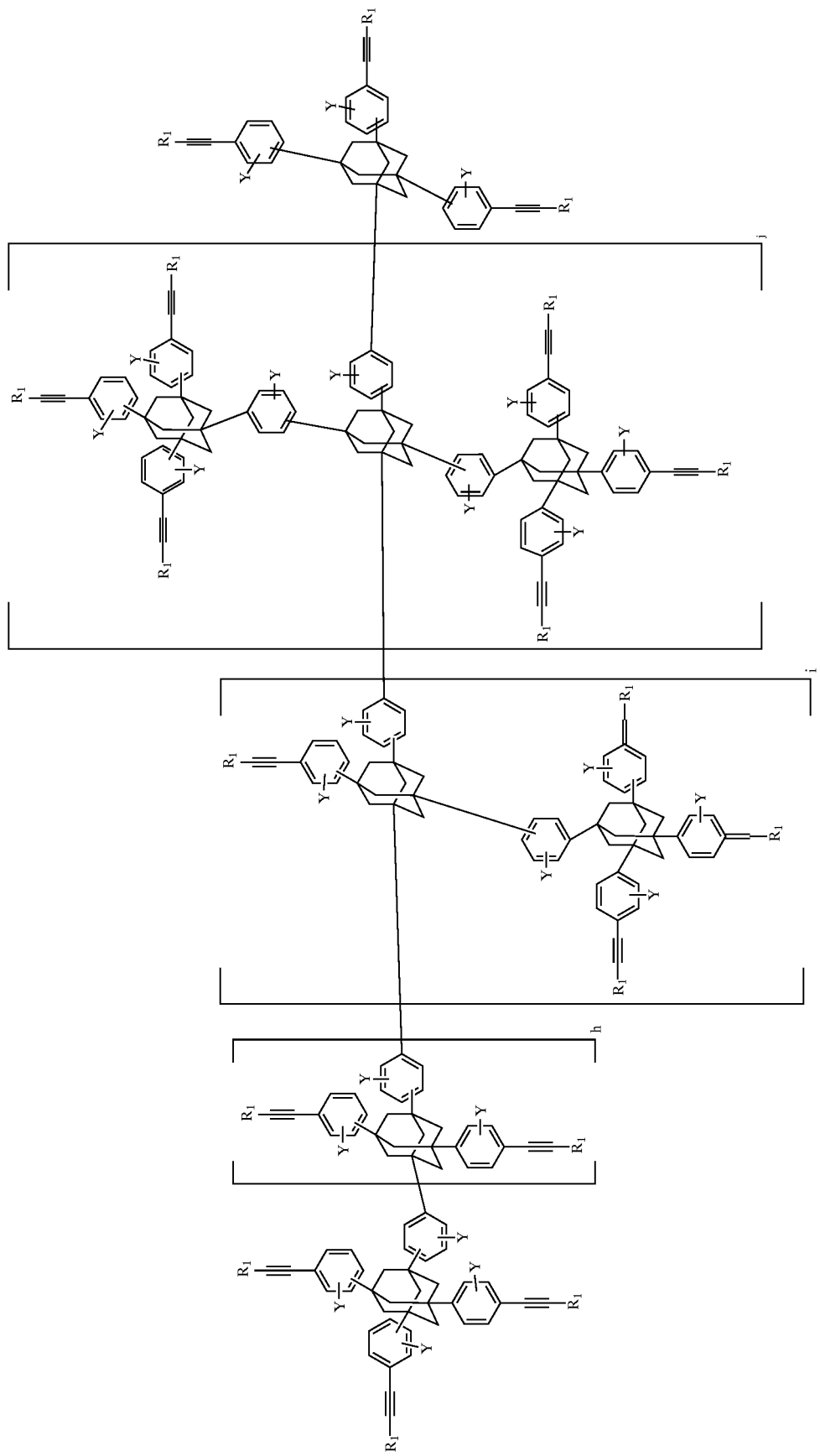

or (1) diamantane monomer of Formula V
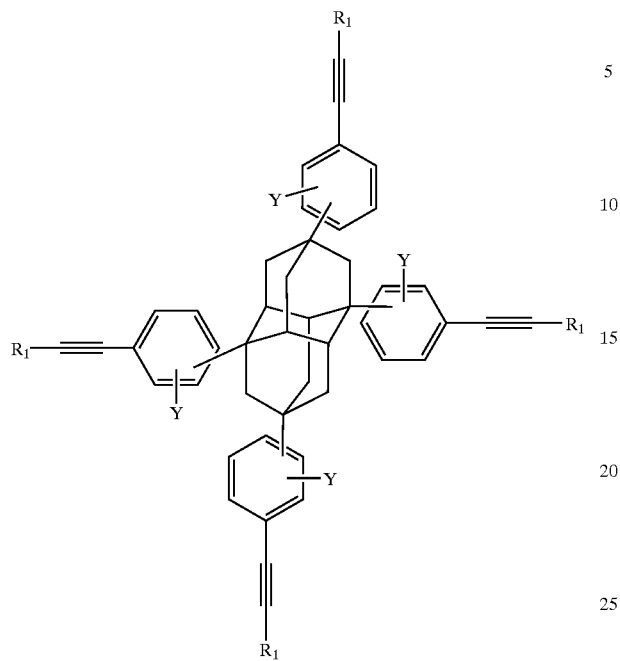
and (2) diamantane oligomer or polymer of Formula VI

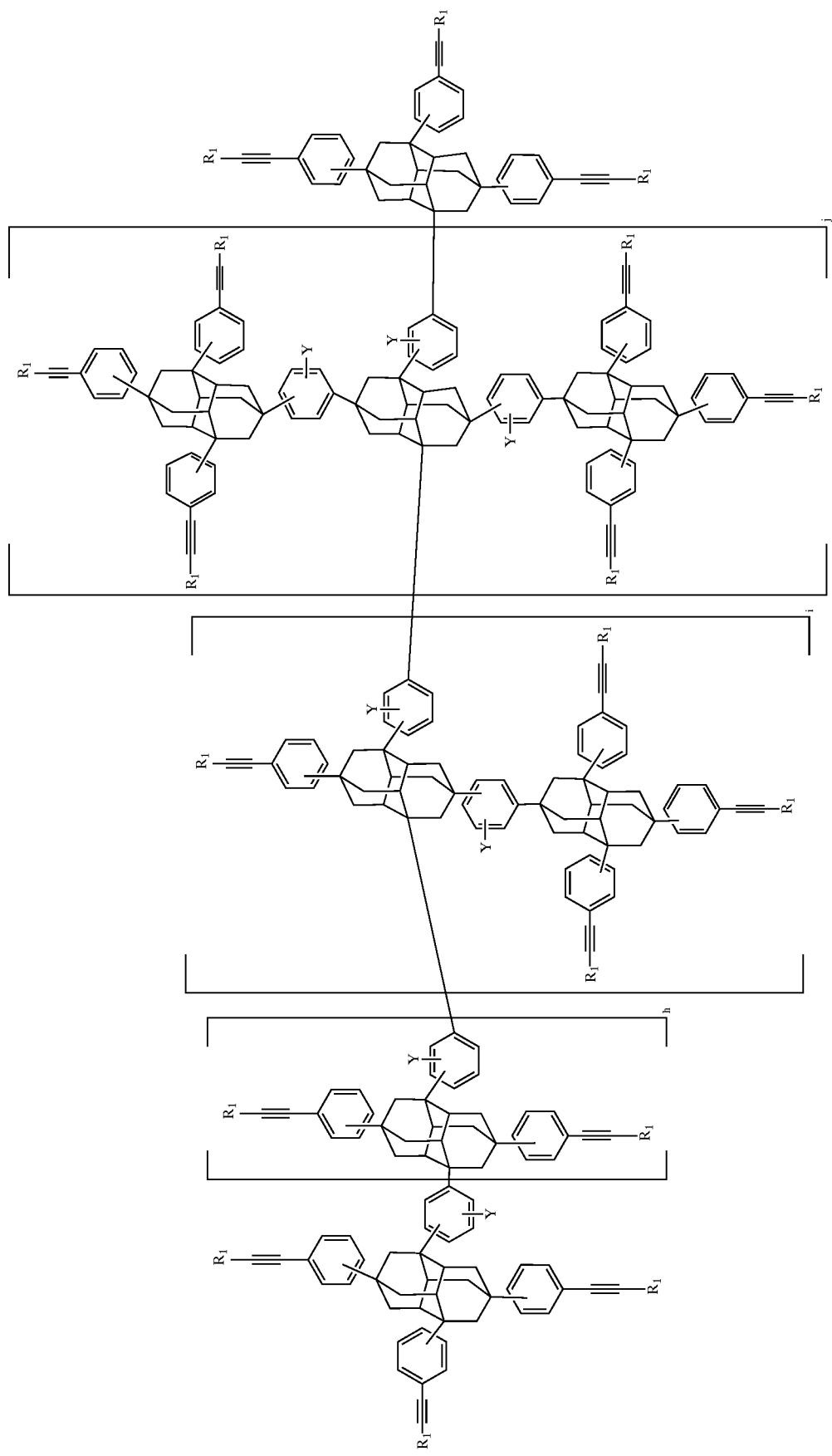

where said h is from 0 to 10; said i is from 0 to 10; said j is from 0 to 10; each of said $R_1$ is the same or different and selected from hydrogen, halogen, alkyl, aryl, substituted aryl, heteroaryl, aryl ether, alkenyl, alkynyl, alkoxyl, hydroxyalkyl, hydroxyaryl, hydroxyalkenyl, hydroxyalkynyl, hydroxyl, or carboxyl; and each of said Y is same or different and is selected from hydrogen, alkyl, aryl, substituted aryl, or halogen.

12. The composition of claim 11 wherein said monomer is present.

13. The composition of claim 11 or 12 wherein said $R_1$ is aryl or substituted aryl and said Y is hydrogen, phenyl, or biphenyl.

14. The composition of claim 13 wherein said (2) adamantane oligomer or polymer is dimer of Formula IX

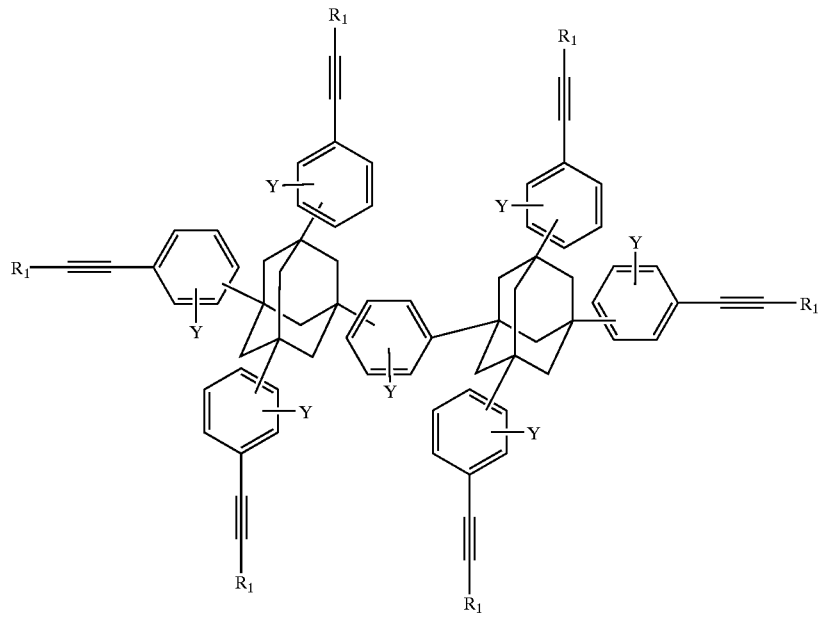

or said (2) diamantane oligomer or polymer is dimer of Formula X

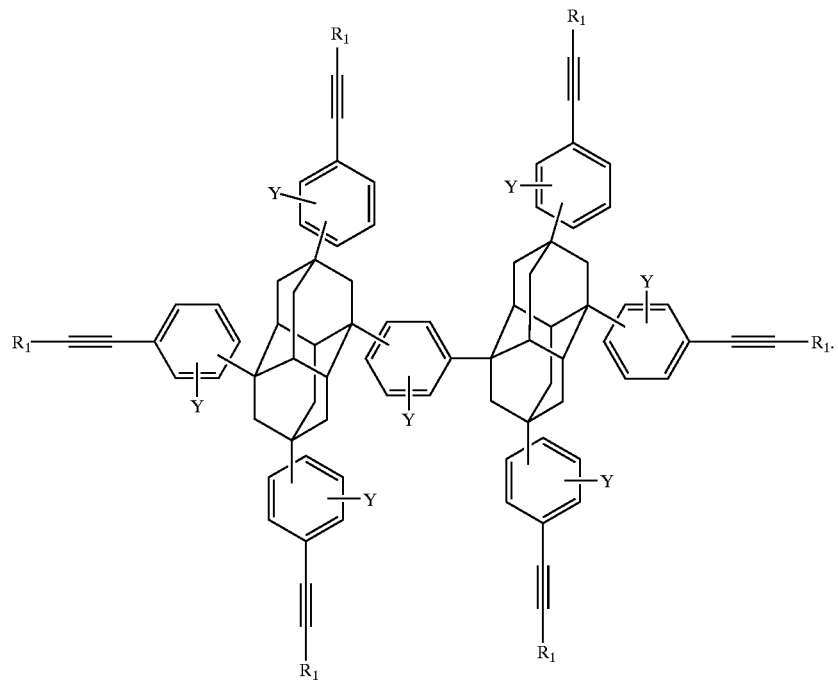

15. The composition of claim 13 wherein said (2) adamantane oligomer or polymer is trimer of Formula XI
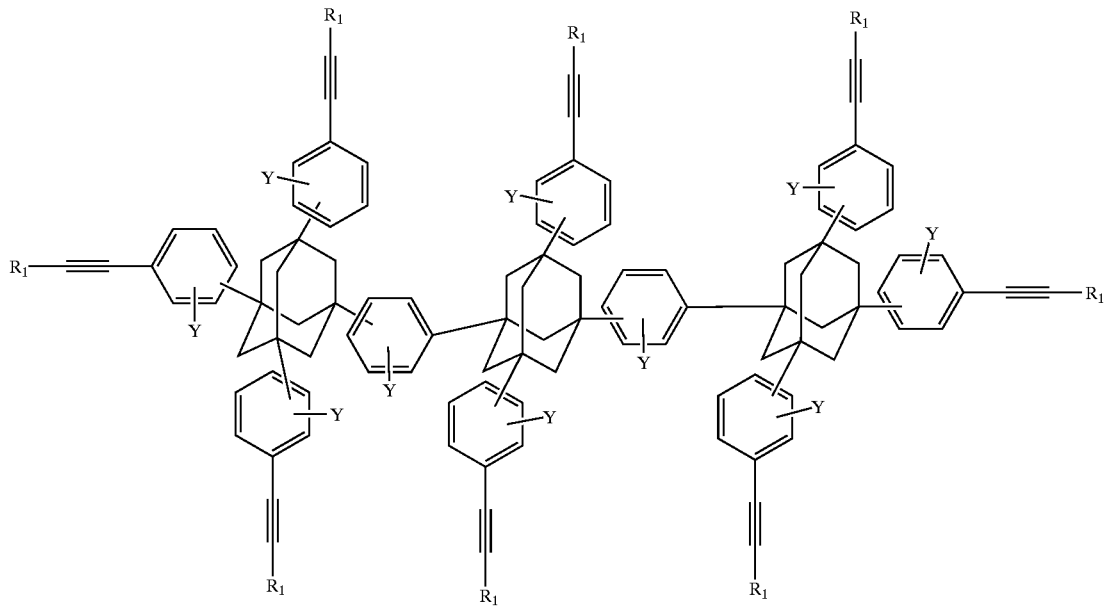
or said (2) diamantane oligomer or polymer is trimer of Formula XII
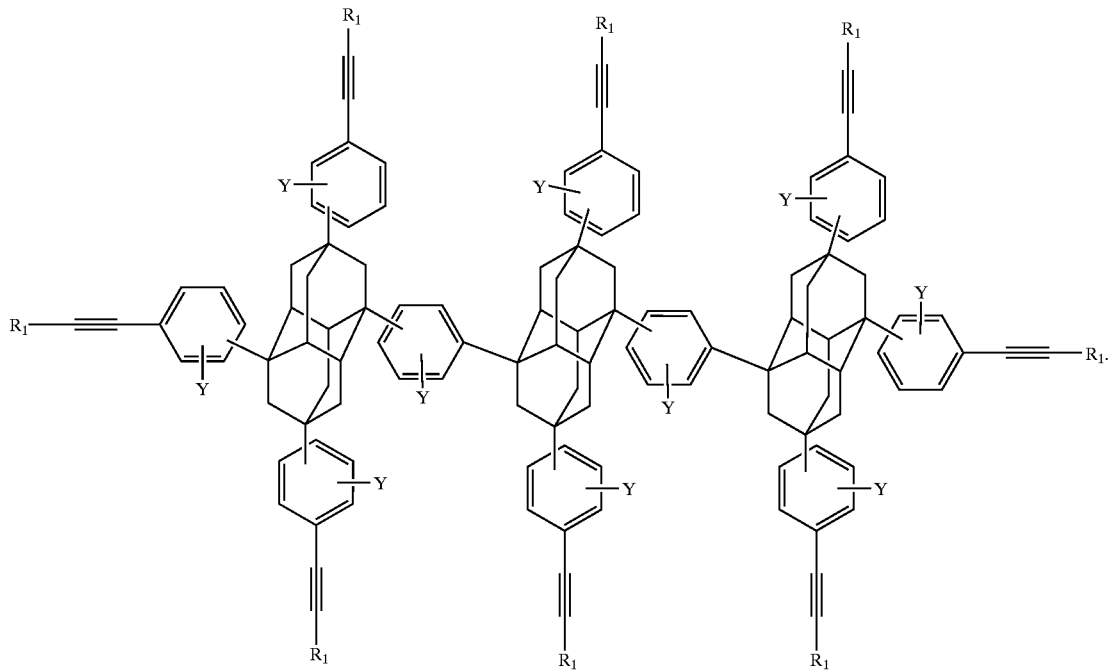

16. The composition of claim 13 where in said thermosetting component (a), said oligomer or polymer (2) comprises a mixture of adamantane dimer of Formula IX
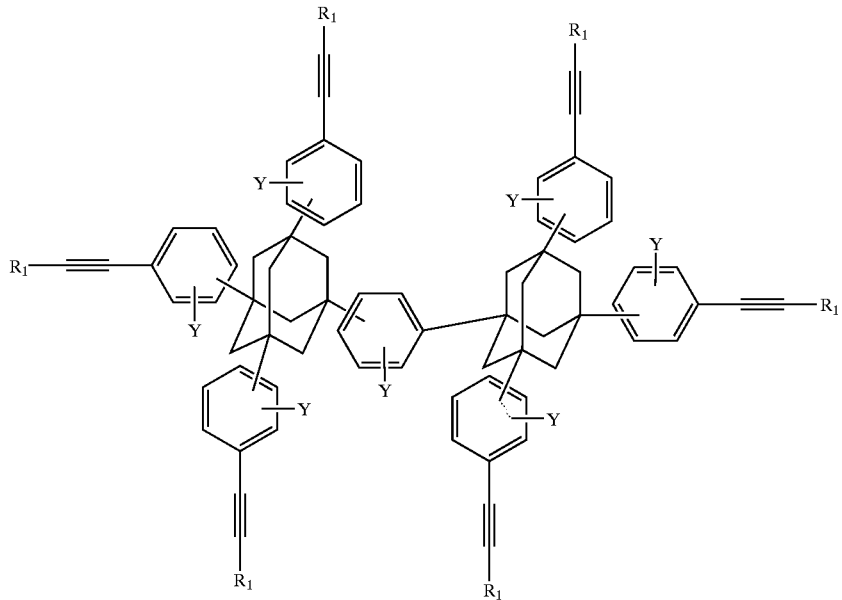
and adamantane trimer of Formula XI
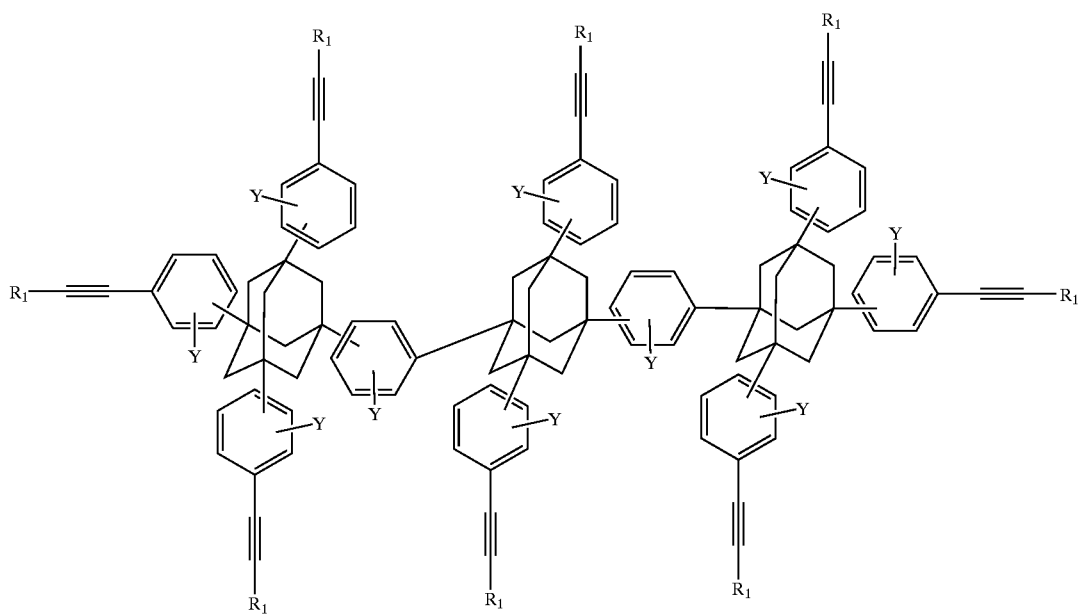

or diamantane dimer of Formula X

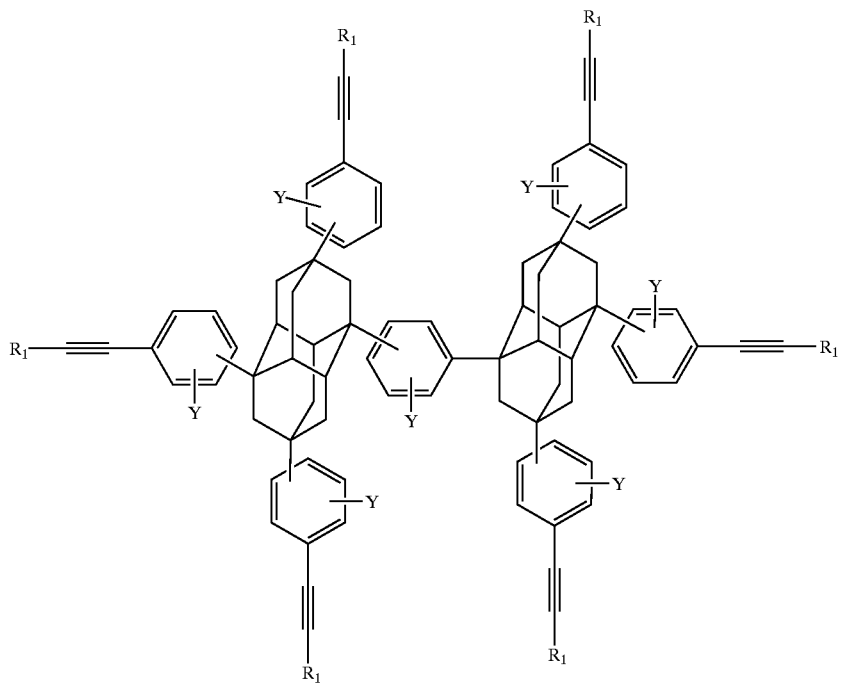

and diamantane trimer of Formula XII

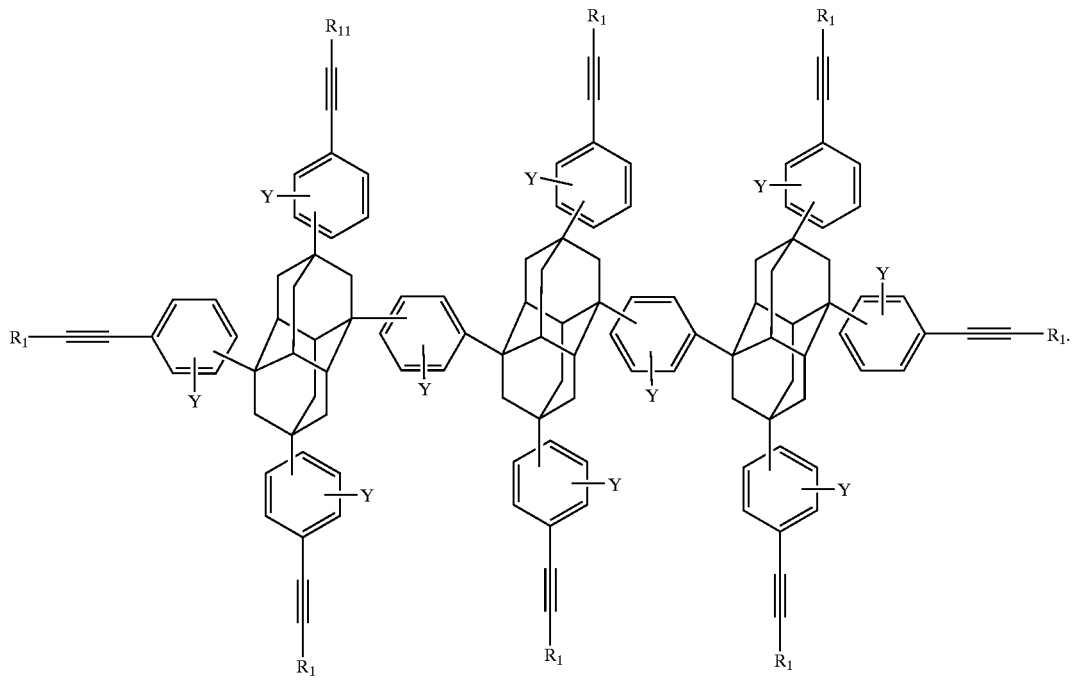

17. The composition of claim 16 where in said thermosetting component (a), said monomer (1) and said oligomer or polymer (2) are adamantane based monomers.

18. The composition of claim 17 wherein at least two of said $R_1C{\equiv}C$ groups on said phenyl groups are two different isomers and at least one of said phenyl groups between two bridgehead carbons of said adamantane monomers exists as two different isomers.

19. The composition of claim 18 wherein said at least two isomers are meta- and para-isomers.

20. The composition of claim 13 additionally comprising (c) adhesion promoter comprising compound having at least bifunctionality wherein the bifunctionality may be the same or different and at least one of said bifunctionality is capable of interacting with said thermosetting component (a).

21. The composition of claim 20 wherein said adhesion promoter is selected from the group consisting of:

silanes of the Formula XXIV: $(R_2)_k(R_3)_l Si(R_4)_m(R_5)_n$ wherein $R_2$, $R_3$, $R_4$, and $R_5$ each independently represents hydrogen, hydroxyl, unsaturated or saturated alkyl, substituted or unsubstituted alkyl where the substituent is amino or epoxy, unsaturated or saturated alkoxyl, unsaturated or saturated carboxylic acid radical, or aryl, at least two of said $R_2$, $R_3$, $R_4$, and $R_5$ represent hydrogen, hydroxyl, saturated or unsaturated alkoxyl, unsaturated alkyl, or unsaturated carboxylic acid radical, and $k+l+m+n \leq 4$;

polycarbosilane of the Formula XXV:

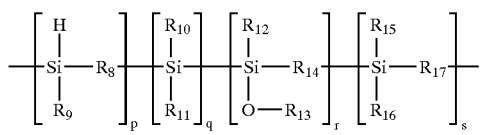

in which $R_8$, $R_{14}$, and $R_{17}$ each independently represents substituted or unsubstituted alkylene, cycloalkylene, vinylene, allylene, or arylene; $R_9$, $R_{10}$, $R_{11}$, $R_{12}$, $R_{15}$, and $R_{16}$ each independently represents hydrogen atom, alkyl, alkylene, vinyl, cycloalkyl, allyl, aryl, or arylene and may be linear or branched, $R_{13}$ represents organosilicon, silanyl, siloxyl, or organo group, and p, q, r, and s satisfy the conditions of $[4 \leq p+q+r+s \leq 100,000]$, and q and r and s may collectively or independently be zero;

glycidyl ethers, or esters of unsaturated carboxylic acids containing at least one carboxylic acid group;

vinyl cyclic oligomers or polymers where the cyclic group is vinyl, aromatic, or heteroaromatic; and phenol-formaldehyde resins or oligomers of the Formula XXVI: $-[R_{18}C_6H_2(OH)(R_{19})]_t-$ where $R_{18}$ is substituted or unsubstituted alkylene, cycloalkylene, vinyl, allyl, or aryl, $R_{19}$ is alkyl, alkylene, vinylene, cycloalkylene, allylene, or aryl, and t=3–100.

22. The composition of claim 21 wherein said adhesion promoter (c) is said phenol-formaldehyde resin or oligomer.

23. An oligomer comprising said composition of claim 20.

24. A spin-on precursor comprising said oligomer of claim 23 and solvent.

25. A thermosetting matrix made from said spin-on precursor of claim 24.

26. A layer comprising said thermosetting matrix of claim 25.

27. The layer of claim 26 wherein said thermosetting matrix is cured.

28. The layer of claim 26 wherein said layer has a dielectric constant of less than 2.7, preferably less than 2.5, preferably less than 2.2, and preferably less than 2.0.

29. The layer of claim 26 wherein said layer has an average pore size diameter of less than 20 nanometers.

30. A substrate having thereon at least one of said layer of claim 26.

31. A microchip comprising said substrate of claim 30.

32. A method of lowering the dielectric constant of a composition comprising (a) thermosetting component comprising: (1) optionally monomer of Formula I

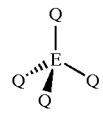

and (2) at least one oligomer or polymer of Formula II

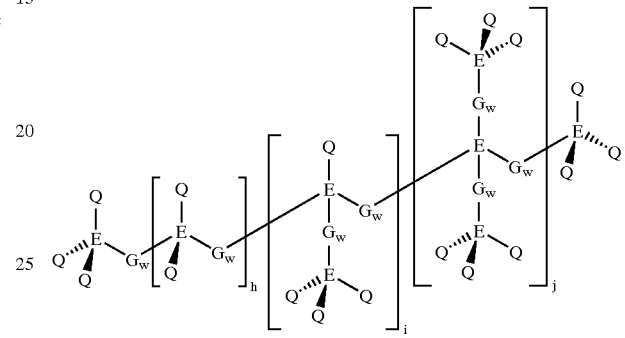

where said E is a cage compound; each of said Q is the same or different and selected from aryl, branched aryl, and substituted aryl wherein said substituents include hydrogen, halogen, alkyl, aryl, substituted aryl, heteroaryl, aryl ether, alkenyl, alkynyl, alkoxyl, hydroxyalkyl, hydroxyaryl, hydroxyalkenyl, hydroxyalkynyl, hydroxyl, or carboxyl; said G is aryl or substituted aryl where substituents include halogen and alkyl; said h is from 0 to 10; said i is from 0 to 10; said j is from 0 to 10; and said w is 0 or 1;

(b) adhesion promoter comprising compound having at least bifunctionality wherein the bifunctionality may be the same or different and the first functionality is capable of interacting with said thermosetting component (a) and the second functionality is capable of interacting with a substrate when said composition is applied to said substrate comprising the steps of:

bonding porogen to said thermosetting component;

decomposing said bonded porogen; and volatilizing said porogen whereby pores form in said composition.

33. The method of claim 32 wherein said thermosetting component (a) is functionalized.

34. The method of claim 33 wherein said thermosetting component functionality is selected from the group consisting of acetylene; 4-ethynylaniline; 3-hydroxyphenylacetylene; 4-fluorophenylacetylene; and 1-ethylcyclohexylamine.

35. The method of claim 32 wherein said porogen comprises a material having a decomposition temperature less than the glass transition temperature of said thermosetting component (a) and greater than the curing temperature of said thermosetting component (a).

36. The method of claim 35 wherein said porogen is selected from the group consisting of unsubstituted polynorbornene, substituted polynorbornene, polycaprolactone, unsubstituted polystyrene, substituted polystyrene, polyacenaphthylene homopolymer, and polyacenaphthylene copolymer.

37. The method of claim 36 wherein said porogen is functionalized.

38. The method of claim 37 wherein said porogen functionality is selected from the group consisting of epoxy, hydroxy, carboxylic acid, amino, and ethynyl.

39. The method of claim 32 wherein said porogen is covalently bonded to said thermosetting component (a).

40. The method of claim 39 wherein said porogen is covalently bonded to said thermosetting component (a) through an ethynyl containing group.

41. The method of claim 40 wherein said ethynyl containing group is acetylene.

42. The method of claim 39 wherein said thermosetting component (a) comprises (1) adamantane monomer of Formula III

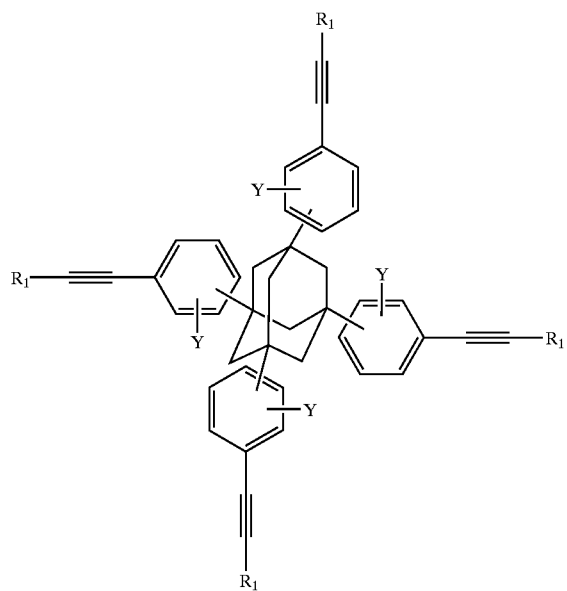

and (2) adamantane oligomer or polymer of Formula IV

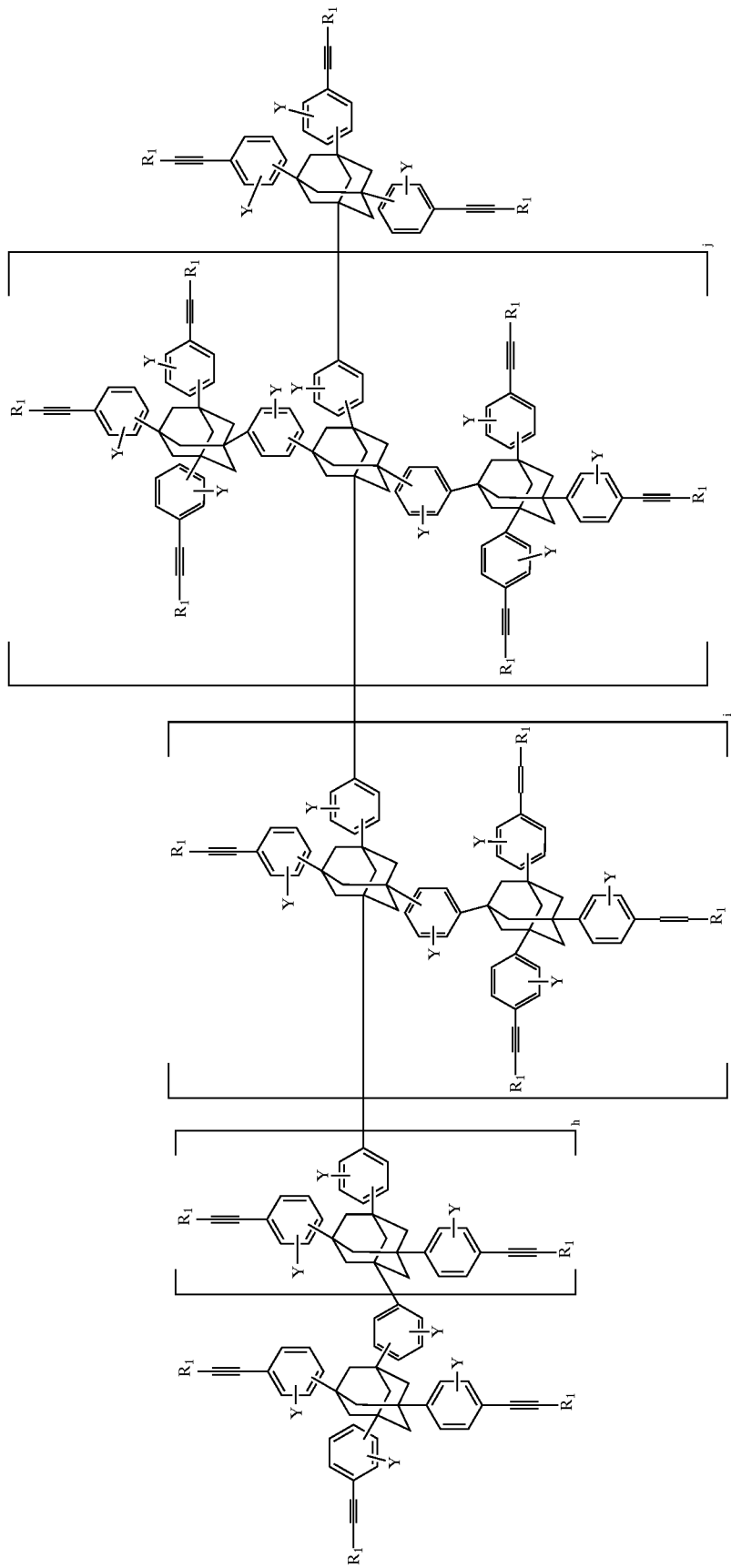

or (1) diamantane monomer of Formula V
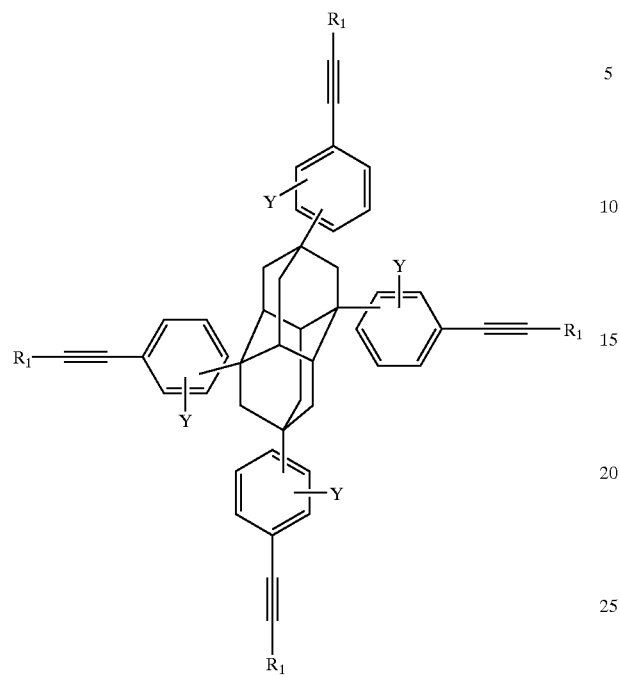
and (2) diamantane oligomer or polymer of Formula VI

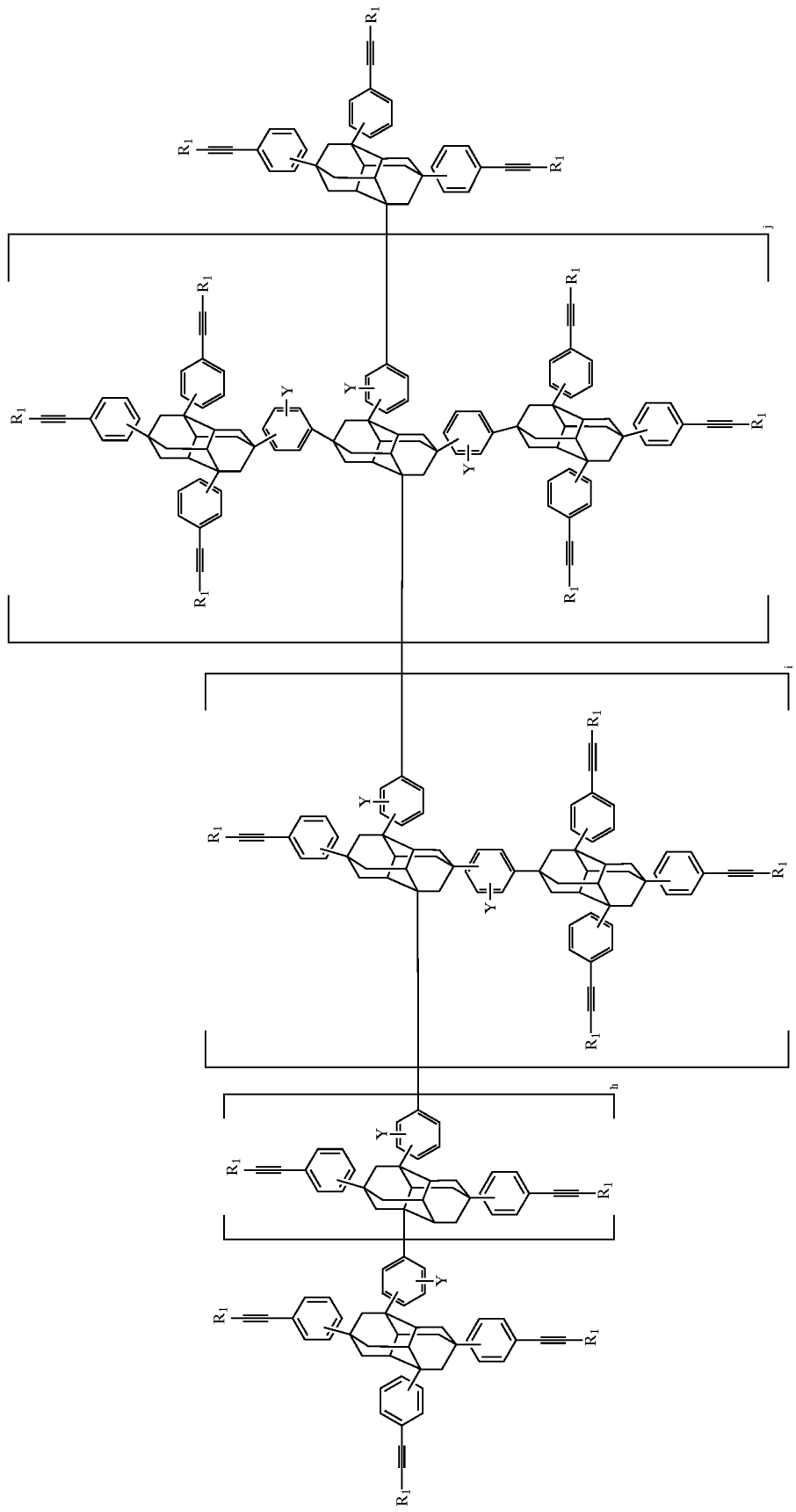

where said h is from 0 to 10; said i is from 0 to 10; said j is from 0 to 10; each of said $R_1$ is the same or different and selected from hydrogen, halogen, alkyl, aryl, substituted aryl, heteroaryl, aryl ether, alkenyl, alkynyl, alkoxyl, hydroxyalkyl, hydroxyaryl, hydroxyalkenyl, hydroxyalkynyl, hydroxyl, or carboxyl; and each of said Y is same or different and is selected from hydrogen, alkyl, aryl, substituted aryl, or halogen.

43. The method of claim 42 wherein said monomer is present.

44. The method of claim 42 or 43 wherein said decomposing said porogen step comprises curing by furnace, hot plate, electron beam radiation, microwave radiation, or ultraviolet radiation.

45. The method of claim 44 wherein said $R_1$ is aryl or substituted aryl and said Y is hydrogen, phenyl, or biphenyl.

46. The method of claim 45 wherein said (2) adamantane oligomer or polymer is dimer of Formula IX

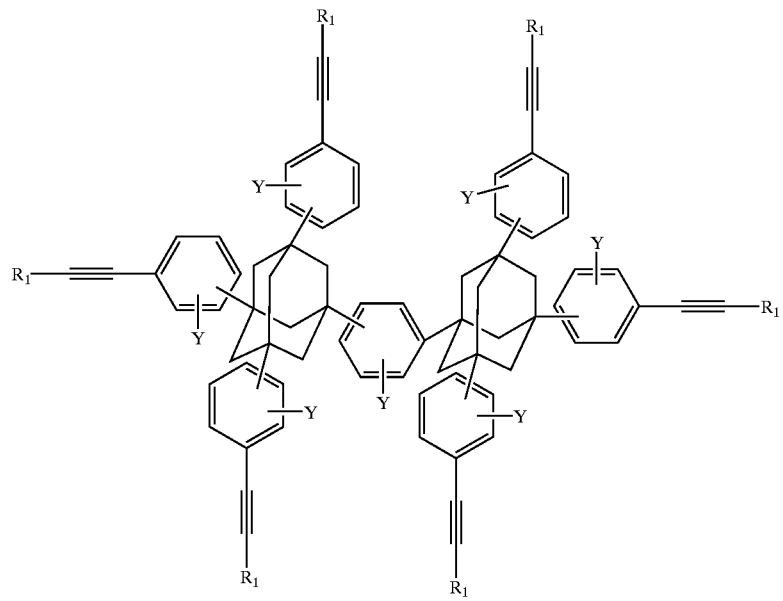

or said (2) diamantane oligomer or polymer is dimer of Formula X

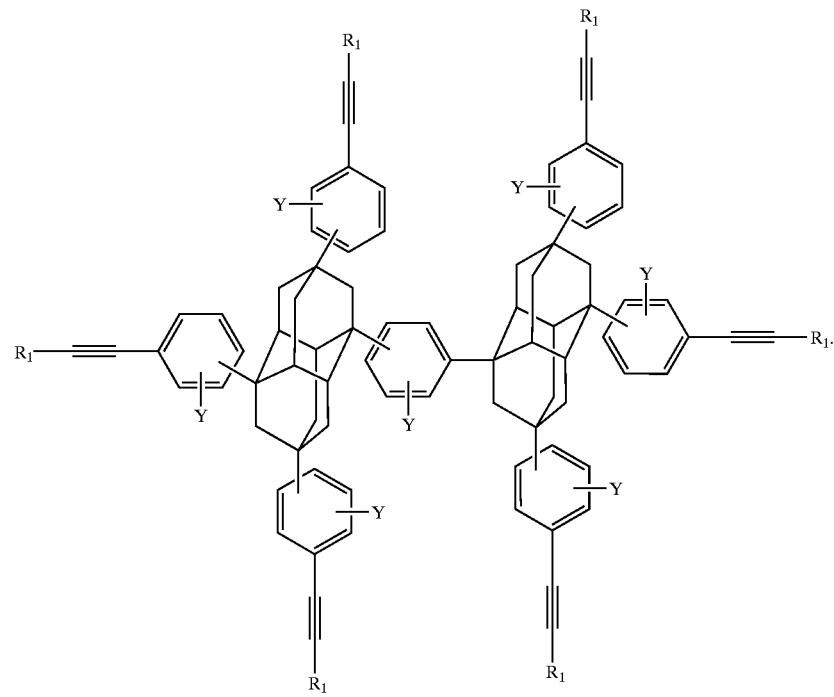

47. The method of claim 45 wherein said (2) adamantane oligomer or polymer is trimer of Formula XI
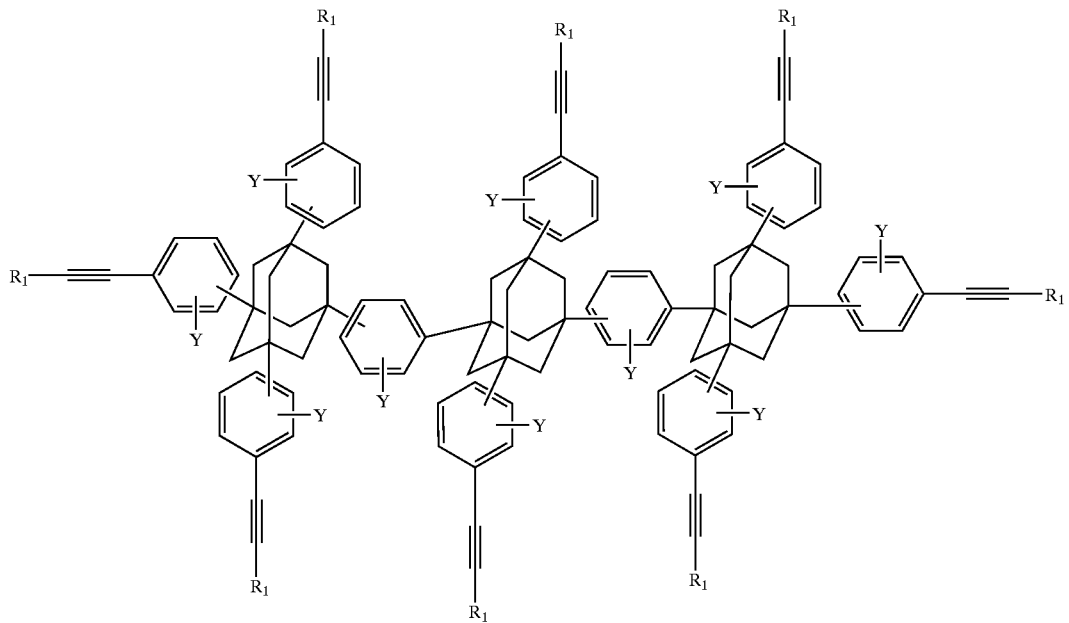
or said (2) diamantane oligomer or polymer is trimer of Formula XII
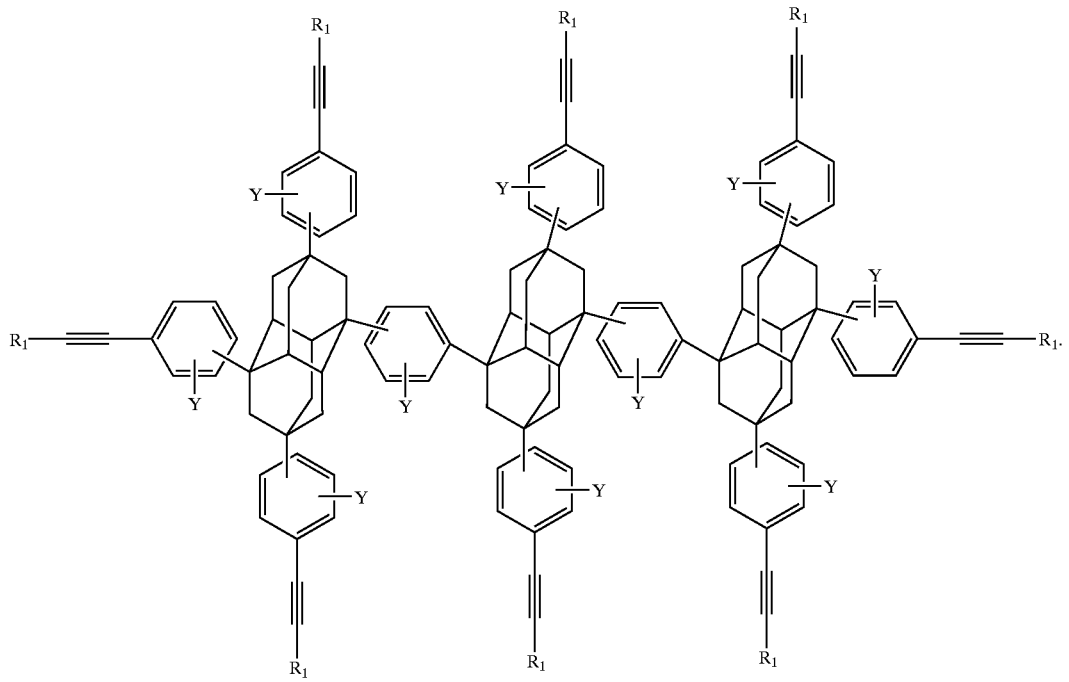

48. The method of claim 45 where in said thermosetting component (a), said oligomer or polymer (2) comprises a mixture of adamantane dimer of Formula IX
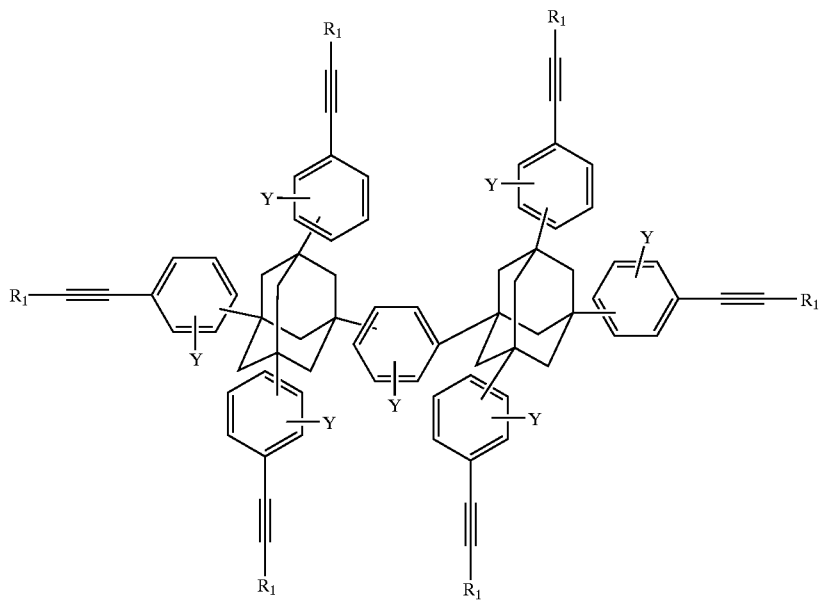
and adamantane trimer of Formula XI
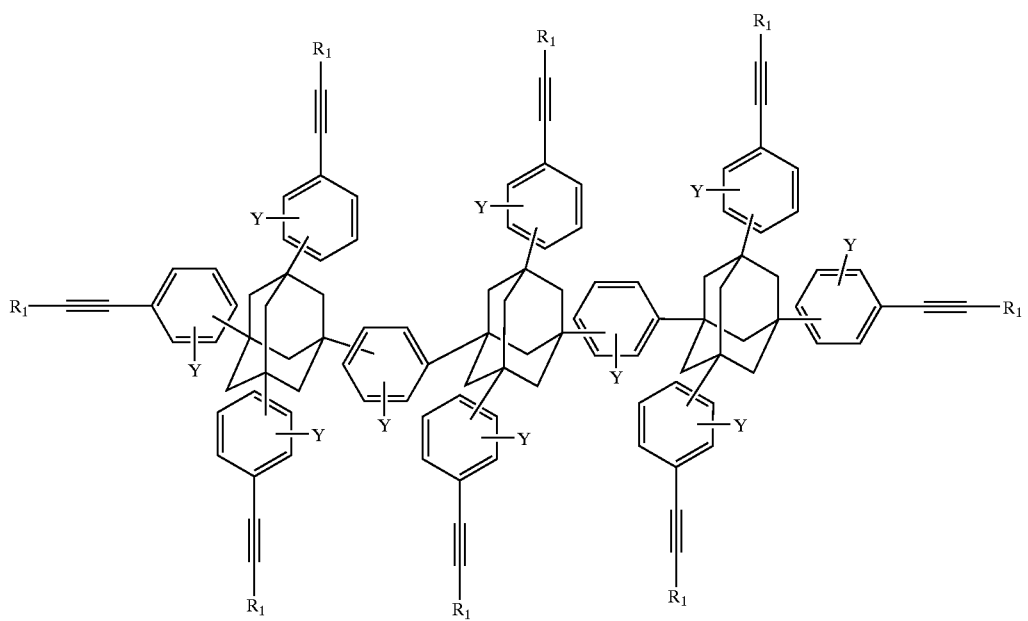

or diamantane dimer of Formula X

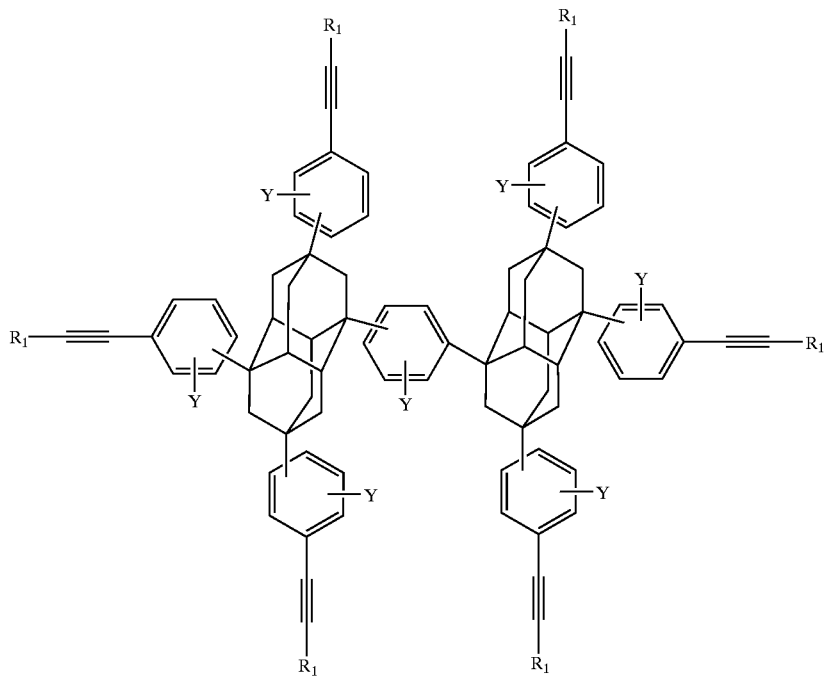

and diamantane trimer of Formula XII

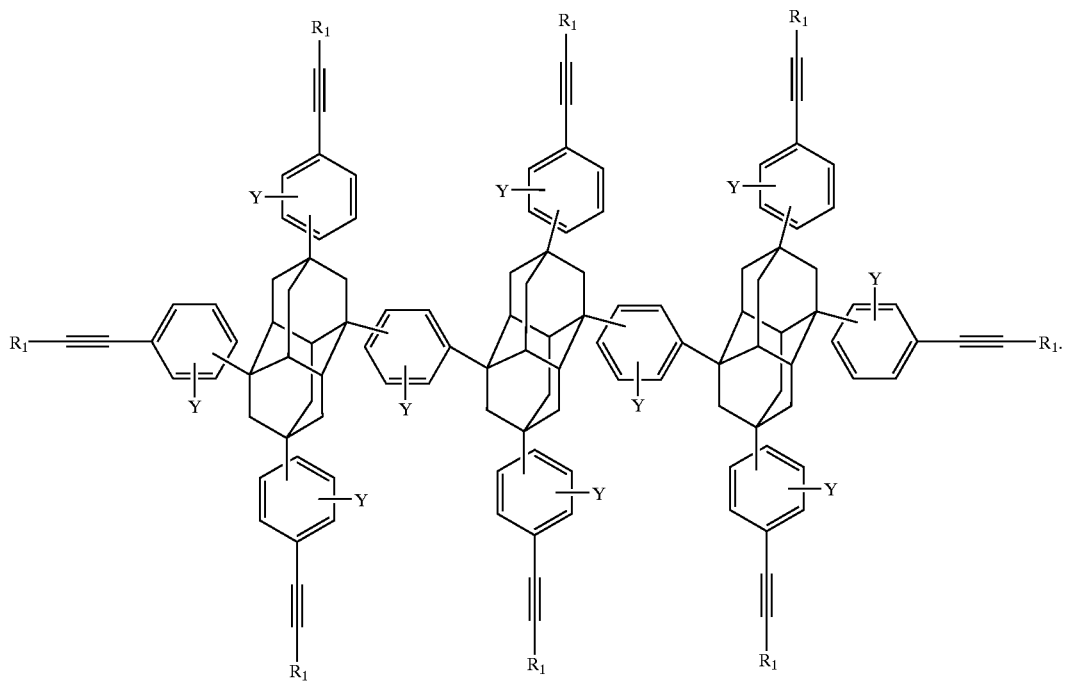

49. The method of claim 48 where in said thermosetting component (a), said monomer (1) and said oligomer or polymer (2) are adamantane based monomers.

50. The method of claim 49 wherein at least two of said $R_1C\equiv C$ groups on said phenyl groups are two different isomers and at least one of said phenyl groups between two bridgehead carbons of said adamantane monomers exists as two different isomers.

51. The method of claim 50 wherein said at least two isomers are meta- and para-isomers.

52. The method of claim 44 wherein at least one of said first functionality and said second functionality of said adhesion promoter (b) is selected from the group consisting of Si containing groups; N containing groups; C bonded to O containing groups; hydroxyl groups; and C double bonded to C containing groups.

53. The method of claim 52 wherein
said Si containing group is selected from silanes of the Formula XXIV: $(R_2)_k(R_3)_lSi(R_4)_m(R_5)_n$ wherein $R_2$, $R_3$, $R_4$, and $R_5$ each independently represents hydrogen, hydroxyl, unsaturated or saturated alkyl, substituted or unsubstituted alkyl where the substituent is amino or epoxy, unsaturated or saturated alkoxyl, unsaturated or saturated carboxylic acid radical, or aryl, at least two of said $R_2$, $R_3$, $R_4$, and $R_5$ represent hydrogen, hydroxyl, saturated or unsaturated alkoxyl, unsaturated alkyl, or unsaturated carboxylic acid radical, and $k+l+m+n \leq 4$; or polycarbosilane of the Formula XXV:

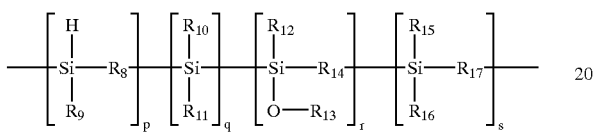

in which $R_8$, $R_{14}$, and $R_{17}$ each independently represents substituted or unsubstituted alkylene, cycloalkylene, vinylene, allylene, or arylene; $R_9$, $R_{10}$, $R_{11}$, $R_{12}$, $R_{15}$, and $R_{16}$ each independently represents hydrogen atom, alkyl, alkylene, vinyl, cycloalkyl, allyl, aryl, or arylene and may be linear or branched, $R_{13}$ represents organosilicon, silanyl, siloxyl, or organo group, and p, q, r, and s satisfy the conditions of $[4 \leq p+q+r+s \leq 100,000]$, and q and r and s may collectively or independently be zero;

said C bonded to O containing groups are selected from glycidyl ethers, or esters of unsaturated carboxylic acids containing at least one carboxylic acid group;

said C double bonded to C containing groups is vinyl cyclic oligomers or polymers where the cyclic group is vinyl, aromatic, or heteroaromatic; and said hydroxyl group is phenol-formaldehyde resins or oligomers of the Formula XXVI: $-[R_{18}C_6H_2(OH)(R_{19})]_t-$ where $R_{18}$ is substituted or unsubstituted alkylene, cycloalkylene, vinyl, allyl, or aryl, $R_{19}$ is alkyl, alkylene, vinylene, cycloalkylene, allylene, or aryl, and $t=3-100$.

54. The method of claim 53 wherein said adhesion promoter (c) is said phenol-formaldehyde resin or oligomer.

* * * * *